US011879003B2

(12) United States Patent
Lee et al.

(10) Patent No.: US 11,879,003 B2
(45) Date of Patent: Jan. 23, 2024

(54) METHODS FOR INCREASING T-CELL FUNCTION

(71) Applicant: Kyverna Therapeutics, Inc., Emeryville, CA (US)

(72) Inventors: John Lee, Alameda, CA (US); Erin O'Brien, Acton, MA (US); Jordan Tsai, Emeryville, CA (US); Lih-Yun Hsu, San Francisco, CA (US); Faye Wu, Emeryville, CA (US)

(73) Assignee: Kyverna Therapeutics, Inc., Emeryville, CA (US)

( * ) Notice: Subject to any disclaimer, the term of this patent is extended or adjusted under 35 U.S.C. 154(b) by 0 days.

(21) Appl. No.: 18/048,621

(22) Filed: Oct. 21, 2022

(65) Prior Publication Data

US 2023/0174615 A1    Jun. 8, 2023

Related U.S. Application Data

(63) Continuation of application No. PCT/US2022/014735, filed on Feb. 1, 2022.

(60) Provisional application No. 63/144,298, filed on Feb. 1, 2021.

(51) Int. Cl.
| | | |
|---|---|---|
| C07K 16/28 | (2006.01) | |
| C07K 14/725 | (2006.01) | |
| A61K 35/17 | (2015.01) | |
| C07K 14/715 | (2006.01) | |

(52) U.S. Cl.
CPC .......... *C07K 14/7051* (2013.01); *A61K 35/17* (2013.01); *C07K 14/7158* (2013.01); *C07K 16/2803* (2013.01); *C07K 16/2866* (2013.01); *C07K 2317/24* (2013.01); *C07K 2317/565* (2013.01); *C07K 2317/622* (2013.01)

(58) Field of Classification Search
None
See application file for complete search history.

(56) References Cited

U.S. PATENT DOCUMENTS

| | | | |
|---|---|---|---|
| 5,795,965 | A | 8/1998 | Tsuchiya et al. |
| 6,521,230 | B1 | 2/2003 | Amlot et al. |
| 8,562,991 | B2 | 10/2013 | Igawa et al. |
| 10,287,350 | B2 | 11/2019 | Kochenderfer |
| 11,446,357 | B2 | 9/2022 | Mahne et al. |
| 2010/0104509 | A1 | 4/2010 | King et al. |
| 2010/0135974 | A1 | 6/2010 | Eshhar et al. |
| 2014/0271635 | A1 | 9/2014 | Brogdon et al. |
| 2015/0283178 | A1 | 10/2015 | June et al. |
| 2016/0145337 | A1 | 5/2016 | Galetto et al. |
| 2016/0362472 | A1 | 12/2016 | Bitter et al. |
| 2017/0107286 | A1 | 4/2017 | Kochenderfer |
| 2018/0044417 | A1 | 2/2018 | Pule et al. |
| 2018/0153977 | A1 | 6/2018 | Wu et al. |
| 2019/0135940 | A1 | 5/2019 | Brogdon et al. |
| 2019/0209616 | A1 | 7/2019 | Galetto et al. |
| 2019/0247443 | A1 | 8/2019 | Scharenberg et al. |
| 2019/0290691 | A1 | 9/2019 | Jackel et al. |
| 2019/0292238 | A1 | 9/2019 | Bitter et al. |
| 2019/0388471 | A1 | 12/2019 | June et al. |
| 2020/0030424 | A1 | 1/2020 | Wu et al. |
| 2020/0140544 | A1 | 5/2020 | Pule et al. |
| 2020/0360431 | A1 | 11/2020 | Garfall et al. |
| 2020/0392248 | A1 | 12/2020 | Zhang |
| 2021/0000869 | A9 | 1/2021 | Galetto et al. |
| 2021/0002366 | A1 | 1/2021 | Purwar et al. |
| 2021/0008111 | A1 | 1/2021 | Seng et al. |
| 2021/0060079 | A1 | 3/2021 | Galetto et al. |
| 2021/0060080 | A1 | 3/2021 | Galetto et al. |
| 2021/0079425 | A1 | 3/2021 | Stauss et al. |
| 2022/0031671 | A1 | 2/2022 | Quarmyne et al. |
| 2022/0110975 | A1 | 4/2022 | Levinson et al. |
| 2022/0143134 | A1 | 5/2022 | Mahne |
| 2022/0169687 | A1 | 6/2022 | Mahne et al. |
| 2023/0056336 | A1 | 2/2023 | Hsu et al. |
| 2023/0104151 | A1 | 4/2023 | Mahne et al. |

FOREIGN PATENT DOCUMENTS

| | | |
|---|---|---|
| WO | WO 2010/115863 | 10/2010 |
| WO | WO 2017/124001 | 7/2017 |
| WO | WO 2018/024894 | 2/2018 |
| WO | WO 2018/115865 | 6/2018 |
| WO | WO 2019/079034 | 4/2019 |
| WO | WO 2019/094847 | 5/2019 |
| WO | WO 2019/113221 | 6/2019 |
| WO | WO 2019/202323 | 10/2019 |
| WO | WO 2019/241549 | 12/2019 |
| WO | WO 2020/128006 | 6/2020 |
| WO | WO 2020/247805 | 12/2020 |
| WO | WO 2021/079149 | 4/2021 |
| WO | WO 2021/092581 | 5/2021 |
| WO | WO 2021/119516 | 6/2021 |
| WO | WO 2021/142302 | 7/2021 |
| WO | WO 2022/043483 | 3/2022 |

OTHER PUBLICATIONS

International Preliminary Report on Patentability in International Appln. PCT/US2021/054504, dated Apr. 27, 2023, 10 pages.
Gao et al., "Cytotoxic T lymphocyte antigen-4 regulates development of xenogenic graft versus host disease in mice via modulation of host immune responses induced by changes in human T cell engraftment and gene expression" *Clinical & Experimental Immunology*, 206(3):422-438, Dec. 2021.
Imura et al., "CD19-targeted CAR regulatory T cells suppress B cell pathology without GvHD" *JCI insight*, 5(14): 16 pages, Jul. 7, 2020.
Zhu et al., "Patients with systemic lupus erythematosus show increased proportions of CD19+ CD20− B cells and secretion of related autoantibodies" Clinical Rheumatology, 40: Abstract 2 pages, Jan. 2021.
International Preliminary Report on Patentability in International Appln. PCT/US2021/044172, dated Feb. 16, 2023, 11 pages.

(Continued)

*Primary Examiner* — Zachary S Skelding
(74) *Attorney, Agent, or Firm* — Fish & Richardson P.C.

(57) ABSTRACT

Provided herein are methods of increasing T-cell function and T-cells produced by these methods. Also provided herein are methods of treating a subject using T-cells produced by these methods.

24 Claims, 6 Drawing Sheets

Specification includes a Sequence Listing.

(56) References Cited

OTHER PUBLICATIONS

Akimova et al., "Human lung tumor FOXP3+ Tregs upregulate four "Treg-locking" transcription factors" *JCI insight*, 2(16): 21 pages, Aug. 17, 2017.
Ando et al., "Inflammatory cytokines induce MAdCAM-1 in murine hepatic endothelial cells and mediate alpha-4 beta-7 integrin dependent lymphocyte endothelial adhesion in vitro" *BMC physiolog*, 7(1):1-9, Dec. 2007.
Bettelli et al.," Foxp3 interacts with nuclear factor of activated T cells and NF-KB to repress cytokine gene expression and effector functions of T helper cells" *Proc Natl Acad Sci USA*, 102(14):5138-43, Mar. 24, 2005.
Brown et al., "Improvements to parallel plate flow chambers to reduce reagent and cellular requirements" *BMC immunology*, 2(9): 1-7, Dec. 2001.
Cedar et al., "Linking DNA methylation and histone modification: patterns and paradigms" *Nat Rev Genet*, 10(5):295-304, May 2009.
Chai et al., "Regulatory T cells, derived from naiive CD4+CD25– T cells by in vitro Foxp3 gene transfer, can induce transplantation tolerance" *Transplantation*, 79(1):1310-1316, May 1, 2005.
Chao et al., "MiR-155 controls follicular Treg cell-mediated humeral autoimmune intestinal injury by inhibiting CTLA-4 expression" *International Immunopharmacology*, 71:10 pp. 2019.
Chen et al., "Conversion of Peripheral CD4CD25 Naive T Cells to CD4CD25 Regulatory T Cells by TGF-Induction of Transcription Factor Foxp3" *The Journal of Experimental Medicine*, 198(12):1875-1886, Dec. 15, 2003.
Chicaybann et al., "An efficient low cost method for gene transfer to T lymphocytes" *PLos One*, 8(3): 11 pages, Mar. 26, 2013.
Cooper et al., "T-cell clones can be rendered specific for CD19: Toward the selective augmentation of the graft-versus-B-lineage leukemia effect" *Blood, The Journal of the American Society of Hematology*, 101(4):1637-1644, 2003.
Cortez et al., "CRISPR screen in regulatory T cells reveals modulators of Foxp3" Nature, 582(7812): 28 pages, Jun. 2020.
Cuadrado et al., "Proteomic analyses of human regulatory T cells reveal adaptations in signaling pathways that protect cellular identity" *Immunity*, 48(5):1046-1059, May 15, 2018.
Dees et al., "Regulatory T cell targeting in cancer: emerging strategies in immunotherapy" *Eur J Immunology*, 51: 280-291, Dec. 10, 2020.
Dustin et al., "Lymphocyte function-associated antigen-1 (LFA-1) interaction with intercellular adhesion molecule-1 (ICAM-1) is one of at least three mechanisms for lymphocyte adhesion to cultured endothelial cells" *The Journal of cell biology*, 107(1):321-331, Jul. 1988.
Eshhar et al., "Specific activation and targeting of cytotoxic lymphocytes through chimeric single chains consisting of antibody-binding domains and the gamma or zeta subunits of the immunoglobulin and T-cell receptors" *Proceedings of the National Academy of Sciences*, 90(2):720-724, 1993.
Feng et al., "Control of the Inheritance of Regulatory T Cell Identity by a cis Element in the Foxp3 Locus" *Cell*, 158: 749-763, 2014.
Ferreira et al., "Next-generation regulatory T cell therapy" *Nature Immunology*, 18:749-769, Apr. 2003.
Floess et al., "Epigenetic control of the foxp3 locus in regulatory T cells" *PLOS biology*, 5(2):e38, 10 pages, Feb. 2007.
Fontenot et al., "Foxp3 programs the development and function of CD4+CD25+ regulatory T cells" *Nature Immunology*, 7 pages, Mar. 3, 2003.
Fransson et al., "CAR/FoxP3-engineered T regulatory cells target the CNS and suppress EAE upon intranasal delivery" *Journal of neuroinflammation*, 9(1):1-12, Dec. 2012.
Frith et al., "The FOXP3A2 isoform supports Treg cell development and protects against severe IPEX syndrome" *Journal of Allergy and Clinical Immunology*, 144(1):317-320, Jul. 1, 2019.
Fu et al., "A multiple redundant genetic switch locks in the transcriptional signature of regulatory T cells" *Nature immunology*, 13(10): 28 pages, Oct. 2012.
Fussenegger, "The impact of mammalian gene regulation concepts on functional genomic research, metabolic engineering, and advanced gene therapies" *Biotechnology Progress*, 17(1):1-51, 2001.
Garg et al., "Blimp1 prevents methylation of Foxp3 and loss of regulatory T cell identity at sites of inflammation" Cell reports, 26(7): Feb. 12, 2019, 21 pages.
GenBank Accession No. NP 000408.1, "interleukin-2 receptor subunit alpha isoform 1 precursor [*Homo sapiens*]" Feb. 20, 2021, 4 pages.
GenBank Accession No. NP 001295171.1, "interleukin-2 receptor subunit alpha isoform 2 precursor [*Homo sapiens*]" Feb. 19, 2021, 3 pages.
GenBank Accession No. NP_001295172.1, "interleukin-2 receptor subunit alpha isoform 3 precursor [*Homo sapiens*]" 3 pages, Feb. 19, 2021.
GenBank Accession No. NP_054728.2, "forkhead box protein P3 isoform a [*Homo sapiens*]" Mar. 7, 2021, 4 pages.
Gondek et al., "Cutting edge: contact-mediated suppression by CD4+ CD25+ regulatory cells involves a granzyme B-dependent, perforin-independent mechanism" *The journal of immunology*, 174(4): 5 pages, Feb. 15, 2005.
Gong et al., "Cytokine-dependent Blimp-1 expression in activated T cells inhibits IL-2 production" *The Journal of Immunology*, 178(1): 12 pages, Jan. 1, 2007.
Grzanka et al., "FoxP3, Helios, and SATB1 : Roles and relationships in regulatory T cells" *International Immunopharmacology*, 13(3):343-347, Feb. 18, 2013.
Guo et al., "CD28 Controls Differentiation of Regulatory T Cells from Naive CD4 T Cells" *The Journal of Immunology*, 181(4):2285-2291, Aug. 6, 2008.
Hippen et al., "Effects of microRNA on regulatory T cells and implications for adoptive cellular therapy to ameliorate graft-versus-host diseases," Frontiers in Immunology, Jan. 2018, 7 pages.
Hori et al., "Control of regulatory T cell development by the transcription factor Foxp3" *Science*, 299(5609): 6 pages, Feb. 14, 2003.
Hosokawa et al., "How transcription factors drive choice of the T cell fate" *Nature*, 21(3):162-176, Mar. 2021.
Huang et al., "miR-142-3p restricts cAMP production in CD4(+)CD25(–) T cells and CD4(+)CD25(+) T-Reg cells by targeting AC9 mRNA" *EMBO Reports*, 6 pages, Feb. 1, 2009.
Hwang et al., "Inflammation-induced Id2 promotes plasticity in regulatory T cells" Nature Comm, 9(1): 13 pages, Nov. 9, 2018.
International Search Report and Written Opinion in International Application No. PCT/US2021/044172, dated Jan. 24, 2022, 21 pages.
International Search Report and Written Opinion in International Application No. PCT/US2021/054504, dated Feb. 2, 2022, -- pages.
International Search Report and Written Opinion in International Application No. PCT/US2021/058711, dated Mar. 11, 2022, 19 pages.
International Search Report and Written Opinion in International Application. No. PCT/US2022/025033, dated Sep. 12, 2022, 23 pages.
International Search Report and Written Opinion in International Application No. PCT/US2022/014735, dated May 12, 2022, 15 pages.
Invitation to Pay Additional Fees and, Where Applicable, Protest Fee in International Application No. PCT/US2022/025033, dated Jul. 19, 2022, 17 pages.
Invitation to Pay Additional Fees, International Application No. PCT/US2021/044172, dated Nov. 26, 2021, 16 pages.
Jaeckel et al., "Antigen-specific FoxP3-transduced T-cells can control established type 1 diabetes" *American Diabetes Association*, 54(2): 306-310, Feb. 1, 2005.
Joly et al., "Foxp3 lacking exons 2 and 7 is unable to confer suppressive ability to regulatory T cells in vivo" *Journal of autoimmunity*, 63:23-30, Sep. 1, 2015.
Khattri et al., "An essential role for Scurfin in CD4+CD25+ T regulatory cells," *Nature Immunology*, Mar. 3, 2003, 6 pages.
Koizunni et al., "Transcriptional regulation of differentiation and functions of effector T regulatory cells" *Cells*, 17 pages, Aug. 20, 2019.

(56) References Cited

OTHER PUBLICATIONS

Kwon et al., "FoxP3 scanning mutagenesis reveals functional variegation and mild mutations with atypical autoimmune phenotypes" *Proc Natl Acad Sci USA*, 115(2):E253-E262, 10 pages, Dec. 21, 2017.

Lefranc et al., "IMGT unique numbering for immunoglobulin and T cell receptor variable domains and Ig superfamily V-like domains" *Developmental & Comparative Immunology*, 27(1): 24 pages, Jan. 1, 2003.

Li et al., "ICOS+ Tregs: a functional subset of Tregs in immune diseases" *Front Innnnunol*, 11:17 pages, Aug. 28, 2020.

Li et al., "DNA-binding properties of FOXP3 transcription factor" *Acta biochimica et biophysica Sinica*, 49(9):792-799, Sep. 1, 2017.

Loser et al., "In vitro-generated regulatory T cells induced by Foxp3-retrovirus infection control murine contact allergy and systemic autoimmunity" *Gene Therapy, Nature Publishing Group*, 12(17):1294-1304, Sep. 1, 2005.

Magg et al., "Subcellular localization of FOXP 3 in human regulatory and nonregulatory T cells" *European journal of immunology*, 42(6):1627-1638, Jun. 2012.

Mansouri et al., "Strategies for multigene expression in eukaryotic cells" *Plasmid*, 75:12-17, Sep. 2014.

Mikami et al., "Epigenetic conversion of conventional T cells into regulatory T cells by CD28 signal deprivation" *Proceedings of the National Academy of Sciences*, 117(22):12258-12268, Jun. 2, 2020.

Miltenyi et al., "High gradient magnetic cell separation with MACS" *Cytometry: The Journal of the International Society for Analytical Cytology*, 11(2):231-238, 1990.

Miyazaki et al., "Id2 and Id3 maintain the regulatory T cell pool to suppress inflammatory disease" *Nature immunology*, 15(8):767-776, Aug. 2014.

Morawski et al., "Foxp3 protein stability is regulated by cyclin-dependent kinase 2" *Journal of Biological Chemistry*, 288(34):24494-24502, Aug. 23, 2003.

Muller et al., "Assays of transendothelial migration in vitro" *Methods in enzymology*, 443:155-176, Abstract, Jan. 1, 2008.

O'Sullivan et al., "Natural killer cell memory" *Immunity*, 43(4):634-645, Oct. 20, 2015.

Ohkura et al., "T cell receptor stimulation-induced epigenetic changes and Foxp3 expression are independent and complementary events required for Treg cell development" *Immunity*, 37(5):785-799, Nov. 16, 2012.

Oshima et al., "Regulation and distribution of MAdCAM-1 in endothelial cells in vitro" *American Journal of Physiology-Cell Physiology*, 281(4):C1096-C1105, Oct. 1, 2001.

Pandiyan et al., "Origin and functions of pro-inflammatory cytokine producing Foxp3+ regulatory T cells" *Cytokine*, 76(1):13-24, Nov. 1, 2015.

Raffin et al., "Treg cell-based therapies: challenges and perspectives" *Nature Reviews Immunology*, 20(3):158-172, Mar. 2020.

Rauch et al., "Id3 maintains Foxp3 expression in regulatory T cells by controlling a transcriptional network of E47, Spi-B, and SOCS3" *Cell reports*, 17(11):2827-2836, Dec. 13, 2016.

Román et al., "Antibody-dependent cellular cytotoxicity (ADCC)" *Antibody Fc, Academic Press*, 1-27, Jan. 1, 2014.

Romano et al., "Past, present, and future of regulatory T cell therapy in transplantation and autoimmunit" *Front. Immunol.*, 10(43): 5 pages, 2019.

Rudra et al., "Transcription factor Foxp3 and its protein partners form a complex regulatory network" *Nature Immunology*, 13(10): 1010-1019, Oct. 1, 2012.

Sadelain et al., "The promise and potential pitfalls of chimeric antigen receptors" *Current opinion in immunology*, 21(2): Abstract 1 page, 2009.

Sakaguchi et al., "Regulatory T cells: how do they suppress immune responses?" *International immunology*, 21(10):1105-1111, 2009.

Schumann et al., "Functional CRISPR dissection of gene networks controlling human regulatory T cell identity" *Nature immunology*, 21(11):1456-1466, Nov. 2020.

Seng et al., "Coexpression of FOXP3 and a helios isofornn enhances the effectiveness of human engineered regulatory T cells" *Blood Adv*, 4(7):1325-1339, Apr. 7, 2020.

Smith et al., "Splice variants of human FOXP3 are functional inhibitors of human CD4+ T-cell activation" *Immunology*, 119(2):203-211, Oct. 2011.

Sousa et al., "Gene expression profile of human T cells following a single stimulation of peripheral blood mononuclear cells with anti-CD3 antibodies" BMC Genomics, *Biomed Central Ltd*, 14 pages, Jul. 19, 2019.

Sullivan et al., "Cutting edge: dynamic expression of Id3 defines the stepwise differentiation of tissue-resident regulatory T cells" *The Journal of Immunology*, 202(1):31-36, Jan. 1, 2019.

Sundrud et al., "Genetic reprogramming of primary human T cells reveals functional plasticity in Th cell differentiation" *The Journal of Immunology*, 171(7): 9 pages, Oct. 1, 2003.

Tai et al., "CD28 costimulation of developing thymocytes induces Foxp3 expression and regulatory T cell differentiation independently of interleukin 2" *Nature Immunology*, 6:152-162, Jan. 2005.

Tao et al., "Foxp3, regulatory T cell, and autoimmune diseases" *Immunology*, 40(1): 328-333, Feb. 2017.

Trzonkowski et al., "CD4+ CD25+ T regulatory cells inhibit cytotoxic activity of T CD8+ and NK lymphocytes in the direct cell-to-cell interaction" *Clinical immunology*, 112(3):258-267, Sep. 1, 2004.

Wang et al., "Transcriptional regulation of Treg homeostasis and functional specification" *Cell Molec Life Sci*, 77: 4269-4287, Nov. 2020.

Wohlfert et al., "GATA3 controls Foxp3+ regulatory T cell fate during inflammation in mice" *The Journal of clinical investigation*, 121(11):4503-4515, Nov. 1, 2011.

Woof et al., "Human antibody-Fc receptor interactions illuminated by crystal structures" *Nature Reviews Immunology* 4(2):89-99, 2004.

Xu et al., "The correlation between proinflammatory cytokines, MAdCAM-1 and cellular infiltration in the inflamed colon from TNF-α gene knockout mice" *Immunology and cell biology*. 85(8): 7 pages, Nov. 2007.

Yagi et al., "Crucial role of FOXP3 in the development and function of human CD25+CD4+ regulatory T cells" *Int Immunology*, 16(11):1643-1656, Oct. 4, 2004.

Zhang et al., "An obligate cell-intrinsic function for CD28 in Tregs" *The Journal of Clinical Investigation*, 123:580-93, Jan. 2, 2013.

Zhang et al., "Clinical significance of miRNAs in autoimmunity" *Journal of Autoimmunity*, 15 pages, Mar. 14, 2020.

Zhang et al., "Humanization of rabbit monoclonal antibodies via grafting combined Kabat/IMGT/Paratome complementarity-determining regions: Rationale and examples" *InMAbs*, 9(3): 12 pages, Apr. 3, 2017.

Zhao et al., "Tregs: Where we are and what comes next?" *Front Immunology*, 8: 14 pages, Nov. 24, 2017.

Feng et al., "Safety and Efficacy of CD19 CAR-T Cells for Refractory Systemic Sclerosis: A Phase I Clinical Trial" *Blood*, 140(Supplement 1): Abstract 2 pages, Nov. 15, 2022.

International Search Report in International Appln. No. PCT/US2023/010034, dated Apr. 18, 2023, 17 pages.

Jin et al., "Therapeutic efficacy of anti-CD19 CAR-T cells in a mouse model of systemic lupus erythematosus" *Cellular & molecular immunology*, 18(8):1896-1903, Aug. 2021.

Kansal et al., "Sustained B cell depletion by CD19-targeted Car T cells is a highly effective treatment for murine lupus" *Science translational medicine*, 11(482): 28 pages Mar. 6, 2019.

Kretschmann et al., "Successful Generation of CD19 Chimeric Antigen Receptor T Cells from Patients with Advanced Systemic Lupus Erythematosus" *Transplantation and Cellular Therapy*, 29(1):27-33, Jan. 1, 2023.

Mackensen et al., "Anti-CD19 CAR T cell therapy for refractory systemic lupus erythematosus" *Nature medicine*, 28(10):2124-2132, 17 pages, Oct. 2022.

Mougiakakos et al., "CD19-targeted Car T cells in refractory systemic lupus erythematosus" *New England Journal of Medicine*, 385(6):567-569, Aug. 5, 2021.

(56) References Cited

OTHER PUBLICATIONS

Schett et al., "CAR-T Cell Treatment of Refractory Systemic Lupus ErythrematosusSafety and Preliminary Efficacy Data from the First Four Patients" *Annals Of The Rheumatic Diseases*, 81(OP0279): 185, May 23, 2022.

Sole-Marce et al., "Reengineering Chimeric Antigen Receptor T Cells for Targeted Therapy of Lupus Nephritis" *Annals Of The Rheumatic Diseases*, 81(POS0463): 2 pages, May 23, 2022.

METHODS FOR INCREASING T-CELL FUNCTION

CROSS-REFERENCE TO RELATED APPLICATION

Pursuant to 35 U.S.C. § 119(e), this application is a continuation of International Application PCT/US2022/014735, with an international filing date of Feb. 1, 2022, which claims priority to U.S. Provisional Patent Application Ser. No. 63/144,298, filed Feb. 1, 2021; the entire contents of which are herein incorporated by reference.

TECHNICAL FIELD

This application is related to the fields of immunology and cell therapy.

SEQUENCE LISTING

This application contains a Sequence Listing that has been submitted electronically as an XML file named 47902-0038001_SL_ST26.xml. The XML file, created on Oct. 20, 2022, is 108,162 bytes in size. The material in the XML file is hereby incorporated by reference in its entirety.

BACKGROUND

Autoimmune diseases are common in the United States, with more than 20 million people suffering from one of 81 known autoimmune diseases. Regulatory T-cells (Tregs) are a subpopulation of T-cells that modulate the immune system and maintain tolerance to self-antigens. Tregs play a role in preventing or treating autoimmune disease (Sakaguchi et al., *Int'l Immun.* 21(10):1105-1111, 2009). FOXP3, a transcription factor expressed in Tregs, has been implicated in maintaining Treg immunosuppressive functions (Hort et al., *Science* 299:1057-1061, 2003). The immunosuppressive mechanisms utilized by Tregs include (i) modulation of antigen-presenting cells (e.g., through CTLA-4 expression by Tregs), (ii) depriving effector T-cells of IL-2 by CD25-mediated IL-2 consumption by Tregs, (iii) cytokine production (e.g., Treg production of immunomodulatory cytokines such as IL-10 and IL-35), and generation of extracellular adenosine through the action of Treg ecto-enzymes CD39 and CD73.

SUMMARY

Provided herein are methods and materials that can be used to treat mammals identified as having an autoimmune disease. Provided herein are methods for increasing T-cell function that include introducing into a T-cell a first nucleic acid sequence encoding a FOXP3 polypeptide and a second nucleic acid sequence encoding a binding agent. Also provided are T-cells produced by any of the methods described herein. Also provided herein are T-cells that include: a first nucleic acid sequence encoding a FOXP3 polypeptide and a second nucleic acid sequence encoding a binding agent. Also provided herein are vectors that include a first nucleic acid sequence encoding a FOXP3 polypeptide and a second nucleic acid sequence encoding a binding agent. Also provided herein are methods and materials for treating a mammal having an autoimmune disease, where the methods include administering to the mammal an effective amount of a T-cell (e.g., any of the T-cells described herein). The methods and materials provided herein can provide a way to enhance and/or stabilize the immunosuppressive effects of a T-cell in order to treat the autoimmune disease.

Provided herein are methods for increasing T-cell function, where the method includes introducing into a T-cell: (i) a first nucleic acid sequence encoding a FOXP3 polypeptide; and (ii) a second nucleic acid sequence encoding a binding agent. In some embodiments, the first nucleic acid sequence encoding a FOXP3 polypeptide includes a mutation in exon 2, where the FOXP3 polypeptide including a mutation in exon 2 results in increased nuclear localization of the FOXP3 polypeptide as compared to a FOXP3 polypeptide including an exon 2 that does not include a mutation. In some embodiments, the mutation includes deletion of exon 2.

In some embodiments, the introducing step further includes introducing a nucleic acid construct, where the nucleic acid construct includes the first nucleic acid sequence and the second nucleic acid sequence, where the first nucleic acid sequence or the second nucleic acid sequence are operably linked to a promoter, and where the first nucleic acid sequence and the second nucleic acid sequence are operably linked, into the T-cell. In some embodiments, the introducing step further includes introducing a third nucleic acid sequence encoding a receptor polypeptide into the T-cell. In some embodiments, the nucleic acid construct further includes the third nucleic acid sequence, where the third nucleic acid sequence is operably linked to a promoter. In some embodiments, third nucleic acid sequence is operably linked to the first nucleic acid sequence and/or the second nucleic acid sequence.

In some embodiments, the receptor polypeptide is a chemokine receptor polypeptide. In some embodiments, the chemokine receptor polypeptide is CCR6, CCR9, and GPR15.

In some embodiments, the binding agent is an antibody or antigen-binding fragment. In some embodiments, the antigen-binding domain is an antigen-binding fragment selected from the group consisting of a Fab, a F(ab')$_2$ fragment, a scFv, a scAb, a dAb, a single domain heavy chain antibody, and a single domain light chain antibody. In some embodiments, the antigen-binding fragment is a scFv that is capable of binding to a cell adhesion molecule. In some embodiments, the cell adhesion molecule is MADCAM-1. In some embodiments, the antigen-binding fragment includes an amino acid sequence at least 80% identical to a sequence selected from the group of SEQ ID NOs: 6-29. In some embodiments, the antigen-binding fragment includes: (i) the three heavy chain CDR sequences present in SEQ ID NO: 30 and the three light chain CDR sequences present in SEQ ID NO: 31; (ii) the three heavy chain CDR sequences present in SEQ ID NO: 32 and the three light chain CDR sequences present in SEQ ID NO: 33; (iii) the three heavy chain CDR sequences present in SEQ ID NO: 34 and the three light chain CDR sequences present in SEQ ID NO: 35; (iv) the three heavy chain CDR sequences present in SEQ ID NO: 36 and the three light chain CDR sequences present in SEQ ID NO: 37; (v) the three heavy chain CDR sequences present in SEQ ID NO: 38 and the three light chain CDR sequences present in SEQ ID NO: 39; (vi) the three heavy chain CDR sequences present in SEQ ID NO: 40 and the three light chain CDR sequences present in SEQ ID NO: 41; (vii) the three heavy chain CDR sequences present in SEQ ID NO: 42 and the three light chain CDR sequences present in SEQ ID NO: 43; (viii) the three heavy chain CDR sequences present in SEQ ID NO: 44 and the three light chain CDR sequences present in SEQ ID NO: 45; (ix) the three heavy chain CDR sequences present in SEQ ID NO: 46 and the three light chain CDR sequences present in SEQ ID NO: 47; (x) the three heavy chain CDR sequences present in SEQ ID NO: 48 and the three light chain CDR sequences present in SEQ ID NO: 49; (xi) the three heavy chain CDR sequences present in SEQ ID NO: 50 and the three light chain CDR sequences present in SEQ ID NO: 51; (xii) the three heavy chain CDR sequences present in SEQ ID NO: 52 and the three light chain CDR sequences present in SEQ ID NO: 53; (xiii) the three heavy chain CDR sequences present in SEQ ID NO: 54 and the three light chain CDR sequences present in SEQ ID NO: 55; (xiv) the three heavy chain CDR sequences present in SEQ ID NO: 56 and the three light chain CDR sequences present in SEQ ID NO: 57; (xv) the three heavy chain CDR sequences present in SEQ ID NO: 58 and the three light chain CDR sequences present in SEQ ID NO: 59; (xvi) the three heavy chain CDR sequences present in SEQ ID NO: 60 and the three light chain CDR sequences present in SEQ ID NO: 61; (xvii) the three heavy chain CDR sequences present in SEQ ID NO: 62 and the three light chain CDR sequences present in SEQ ID NO: 63; (xviii) the three heavy chain CDR sequences present in SEQ ID NO: 64 and the three light chain CDR sequences present in SEQ ID NO: 65; (xix) the three heavy chain CDR sequences present in SEQ ID NO: 66 and the three light chain CDR sequences present in SEQ ID NO: 67; (xx) the three heavy chain CDR sequences present in SEQ ID NO: 68 and the three light chain CDR sequences present in SEQ ID NO: 69; (xxi) the three heavy chain CDR sequences present in SEQ ID NO: 70 and the three light chain CDR sequences present in SEQ ID NO: 71; (xxii) the three heavy chain CDR sequences present in SEQ ID NO: 72 and the three light chain CDR sequences present in SEQ ID NO: 73; (xxiii) the three heavy chain CDR sequences present in SEQ ID NO: 74 and the three light chain CDR sequences present in SEQ ID NO: 75; or (xxiv) the three heavy chain CDR sequences present in SEQ ID NO: 76 and the three light chain CDR sequences present in SEQ ID NO: 77.

In some embodiments, the binding agent is a chimeric antigen receptor, where the chimeric antigen receptor includes an extracellular domain, a transmembrane domain, and an intracellular domain, where the extracellular domain includes an antibody or an antigen-binding domain capable of binding to an antigen on an autoimmune cell, and where the intracellular domain includes a cytoplasmic signaling domain and one or more co-stimulatory domains.

In some embodiments, the antigen-binding domain is an antigen-binding fragment selected from the group consisting of a Fab, a F(ab')$_2$ fragment, a scFv, a scAb, a dAb, a single domain heavy chain antibody, and a single domain light chain antibody. In some embodiments, the antigen-binding fragment is a scFv that is capable of binding to a cell adhesion molecule. In some embodiments, the cell adhesion molecule is MADCAM-1. In some embodiments, the antigen-binding fragment includes an amino acid sequence at least 80% identical to a sequence selected from the group of SEQ ID NOs: 6-37.

In some embodiments, the cytoplasmic signaling domain is a CD3 zeta domain. In some embodiments, the co-stimulatory domain includes at least one of a CD48, 4-1BB, ICOS, X-40, or CD27 domain.

In some embodiments, the introducing step further includes introducing an additional nucleic acid sequence encoding a therapeutic gene product into the T-cell. In some embodiments, the nucleic acid construct further includes an additional sequence encoding the therapeutic gene product. In some embodiments, the additional nucleic acid sequence is operably linked a promoter or is operably linked to the first nucleic acid sequence, the second nucleic acid sequence, and/or the third nucleic acid sequence.

In some embodiments, the nucleic acid construct includes a viral vector selected from the group of a lentiviral vector, a retroviral vector, an adenoviral vector, or an adeno-associated viral (AAV) vector. In some embodiments, viral vector is a lentiviral vector. In some embodiments, the introducing step includes viral transduction.

In some embodiments, the T-cell is a CD4$^+$ T-cell or a CD4$^+$/CD45RA$^+$ T-cell. In some embodiments, the method further includes: obtaining a T-cell from a patient or obtaining T-cells allogenic to the patient.

In some embodiments, the method further includes: treating the obtained T-cells to isolate a population of cells enriched for CD4$^+$ T-cells or CD4$^+$/CD45RA$^+$ T-cells. Also provided herein are T-cells produced by any of the methods described herein.

Also provided herein are compositions including any of the T-cells or populations of T-cells described herein.

Also provided herein are T-cells that include a first nucleic acid sequence encoding a FOXP3 polypeptide; and a second nucleic acid sequence encoding a binding agent. In some embodiments, the first nucleic acid sequence encoding a FOXP3 polypeptide includes a mutation in exon 2, where the FOXP3 polypeptide including a mutation in exon 2 results in increased nuclear localization of the FOXP3 polypeptide as compared to a FOXP3 polypeptide including an exon 2 that does not include a mutation. In some embodiments, the mutation includes deletion of exon 2. In some embodiments, the first nucleic acid sequence is operably linked to a promoter. In some embodiments, the second nucleic acid sequence is operably linked to a promoter.

In some embodiments, the T-cell further includes a third nucleic acid sequence encoding a receptor polypeptide. In some embodiments, the third nucleic acid sequence is operably linked to a promoter. In some embodiments, the receptor polypeptide is a chemokine receptor polypeptide. In some embodiments, the chemokine receptor polypeptide is CCR6, CCR9, or GPR15.

In some embodiments, the binding agent is an antibody or antigen-binding domain. In some embodiments, the antigen-binding domain is an antigen-binding fragment selected from the group consisting of a Fab, a F(ab')$_2$ fragment, a scFv, a scAb, a dAb, a single domain heavy chain antibody, and a single domain light chain antibody. In some embodiments, the antigen-binding fragment is a scFv that is capable of binding to a cell adhesion molecule. In some embodiments, the cell adhesion molecule is MADCAM-1. In some embodiments, the antigen-binding fragment includes an amino acid sequence at least 80% identical to a sequence selected from the group consisting of SEQ ID NOs: 6-29. In some embodiments, the antigen-binding fragment includes: (i) the three heavy chain CDR sequences present in SEQ ID NO: 30 and the three light chain CDR sequences present in SEQ ID NO: 31; (ii) the three heavy chain CDR sequences present in SEQ ID NO: 32 and the three light chain CDR sequences present in SEQ ID NO: 33; (iii) the three heavy chain CDR sequences present in SEQ ID NO: 34 and the three light chain CDR sequences present in SEQ ID NO: 35; (iv) the three heavy chain CDR sequences present in SEQ ID NO: 36 and the three light chain CDR sequences present in SEQ ID NO: 37; (v) the three heavy chain CDR sequences present in SEQ ID NO: 38 and the three light chain CDR sequences present in SEQ ID NO: 39; (vi) the three heavy chain CDR sequences present in SEQ ID NO: 40 and the three light chain CDR sequences present in SEQ ID NO: 41; (vii) the three heavy chain CDR sequences present in SEQ ID NO: 42 and the three light chain CDR sequences present in SEQ ID NO: 43; (viii) the three heavy chain CDR sequences present in SEQ ID NO: 44 and the three light chain CDR sequences present in SEQ ID NO: 45; (ix) the three heavy chain CDR sequences present in SEQ ID NO: 46 and the three light chain CDR sequences present in SEQ ID NO: 47; (x) the three heavy chain CDR sequences present in SEQ ID NO: 48 and the three light chain CDR sequences present in SEQ ID NO: 49; (xi) the three heavy chain CDR sequences present in SEQ ID NO: 50 and the three light chain CDR sequences present in SEQ ID NO: 51; (xii) the three heavy chain CDR sequences present in SEQ ID NO: 52 and the three light chain CDR sequences present in SEQ ID NO: 53; (xiii) the three heavy chain CDR sequences present in SEQ ID NO: 54 and the three light chain CDR sequences present in SEQ ID NO: 55; (xiv) the three heavy chain CDR sequences present in SEQ ID NO: 56 and the three light chain CDR sequences present in SEQ ID NO: 57; (xv) the three heavy chain CDR sequences present in SEQ ID NO: 58 and the three light chain CDR sequences present in SEQ ID NO: 59; (xvi) the three heavy chain CDR sequences present in SEQ ID NO: 60 and the three light chain CDR sequences present in SEQ ID NO: 61; (xvii) the three heavy chain CDR sequences present in SEQ ID NO: 62 and the three light chain CDR sequences present in SEQ ID NO: 63; (xviii) the three heavy chain CDR sequences present in SEQ ID NO: 64 and the three light chain CDR sequences present in SEQ ID NO: 65; (xix) the three heavy chain CDR sequences present in SEQ ID NO: 66 and the three light chain CDR sequences present in SEQ ID NO: 67; (xx) the three heavy chain CDR sequences present in SEQ ID NO: 68 and the three light chain CDR sequences present in SEQ ID NO: 69; (xxi) the three heavy chain CDR sequences present in SEQ ID NO: 70 and the three light chain CDR sequences present in SEQ ID NO: 71; (xxii) the three heavy chain CDR sequences present in SEQ ID NO: 72 and the three light chain CDR sequences present in SEQ ID NO: 73; (xxiii) the three heavy chain CDR sequences present in SEQ ID NO: 74 and the three light chain CDR sequences present in SEQ ID NO: 75; or (xxiv) the three heavy chain CDR sequences present in SEQ ID NO: 76 and the three light chain CDR sequences present in SEQ ID NO: 77.

In some embodiments, the binding agent is a chimeric antigen receptor, where the chimeric antigen receptor includes an extracellular domain, a transmembrane domain, and an intracellular domain, where the extracellular domain includes an antibody or antigen-binding domain capable of binding to an antigen on an autoimmune cell, and where the intracellular domain includes a cytoplasmic signaling domain and one or more co-stimulatory domains. In some embodiments, the antigen-binding domain is an antigen-binding fragment selected from the group consisting of a Fab, a F(ab')$_2$ fragment, a scFv, a scAb, a dAb, a single domain heavy chain antibody, and a single domain light chain antibody. In some embodiments, the antigen-binding fragment is a scFv that is capable of binding to a cell adhesion molecule. In some embodiments, the cell adhesion molecule is preferably MADCAM-1. In some embodiments, the antigen-binding fragment includes an amino acid sequence at least 80% identical to a sequence selected from the group consisting of SEQ ID NOs: 6-29. In some embodiments, the cytoplasmic signaling domain is a CD3 zeta domain. In some embodiments, the co-stimulatory domain includes at least one of a CD48, 4-1BB, ICOS, X-40, or CD27 domain.

In some embodiments, the T-cell further includes an additional nucleic acid sequence encoding a therapeutic gene product, where the additional nucleic acid sequence is operably linked to a promoter.

Also provided herein are compositions including a T-cell or population of T-cells produced by any of the methods described herein, or any of the T-cells or populations of T-cells described herein.

Also provided herein are methods of producing a T-cell population expressing an exogenous FOXP3 polypeptide and a receptor polypeptide that include culturing any of the T-cells described herein in growth media under conditions sufficient to expand the population of T-cells.

Also provided herein are populations of T-cells prepared using any of the methods described herein.

Also provided herein are vectors that include a first nucleic acid sequence encoding a FOXP3 polypeptide and a second nucleic acid sequence encoding a binding agent. In some embodiments, the first nucleic acid sequence includes a mutation that results in nuclear localization of the FOXP3 polypeptide. In some embodiments, the first nucleic acid sequence encoding a FOXP3 polypeptide includes a mutation in exon 2, where the FOXP3 polypeptide including a mutation in exon 2 results in increased nuclear localization of the FOXP3 polypeptide as compared to a FOXP3 polypeptide including an exon 2 that does not include a mutation. In some embodiments, the mutation includes deletion of exon 2.

In some embodiments, the first nucleic acid sequence is 5' positioned relative to the second nucleic acid in the vector. In some embodiments, the first nucleic acid sequence is operably linked to a promoter.

In some embodiments, the vector further includes an additional nucleic acid sequence between the first nucleic acid sequence and the second nucleic acid sequence, where the additional nucleic acid sequence operably links the second nucleic acid sequence to the first nucleic acid sequence. In some embodiments, the second nucleic acid sequence is 5' positioned relative to the first nucleic acid in the vector. In some embodiments, the second nucleic acid sequence is operably linked to a promoter.

In some embodiments, the vector further includes a third nucleic acid sequence encoding a receptor polypeptide. In some embodiments, the third sequence is operably linked to the first sequence and/or the second sequence. In some embodiments, the third sequence is operably linked to a promoter. In some embodiments, the receptor polypeptide is a chemokine receptor polypeptide. In some embodiments, the chemokine receptor polypeptide is CCR6, CCR9 or GPR15.

In some embodiments, the binding agent is an antibody or antigen-binding domain. In some embodiments, the antigen-binding domain is an antigen-binding fragment selected from the group consisting of a Fab, a F(ab')$_2$ fragment, a scFV, a scAb, a dAb, a single domain heavy chain antibody, and a single domain light chain antibody. In some embodiments, the antigen-binding fragment is a scFv that is capable of binding to an antigen on an autoimmune cell or a cell adhesion molecule. In some embodiments, the cell adhesion molecule is MADCAM-1. In some embodiments, the antigen-binding fragment includes an amino acid sequence at least 80% identical to a sequence selected from the group of SEQ ID NOs: 6-29. In some embodiments, the antigen-binding fragment includes: (i) the three heavy chain CDR sequences present in SEQ ID NO: 30 and the three light chain CDR sequences present in SEQ ID NO: 31; (ii) the three heavy chain CDR sequences present in SEQ ID NO: 32 and the three light chain CDR sequences present in SEQ ID NO: 33; (iii) the three heavy chain CDR sequences present in SEQ ID NO: 34 and the three light chain CDR sequences present in SEQ ID NO: 35; (iv) the three heavy chain CDR sequences present in SEQ ID NO: 36 and the three light chain CDR sequences present in SEQ ID NO: 37; (v) the three heavy chain CDR sequences present in SEQ ID NO: 38 and the three light chain CDR sequences present in SEQ ID NO: 39; (vi) the three heavy chain CDR sequences present in SEQ ID NO: 40 and the three light chain CDR sequences present in SEQ ID NO: 41; (vii) the three heavy chain CDR sequences present in SEQ ID NO: 42 and the three light chain CDR sequences present in SEQ ID NO: 43; (viii) the three heavy chain CDR sequences present in SEQ ID NO: 44 and the three light chain CDR sequences present in SEQ ID NO: 45; (ix) the three heavy chain CDR sequences present in SEQ ID NO: 46 and the three light chain CDR sequences present in SEQ ID NO: 47; (x) the three heavy chain CDR sequences present in SEQ ID NO: 48 and the three light chain CDR sequences present in SEQ ID NO: 49; (xi) the three heavy chain CDR sequences present in SEQ ID NO: 50 and the three light chain CDR sequences present in SEQ ID NO: 51; (xii) the three heavy chain CDR sequences present in SEQ ID NO: 52 and the three light chain CDR sequences present in SEQ ID NO: 53; (xiii) the three heavy chain CDR sequences present in SEQ ID NO: 54 and the three light chain CDR sequences present in SEQ ID NO: 55; (xiv) the three heavy chain CDR sequences present in SEQ ID NO: 56 and the three light chain CDR sequences present in SEQ ID NO: 57; (xv) the three heavy chain CDR sequences present in SEQ ID NO: 58 and the three light chain CDR sequences present in SEQ ID NO: 59; (xvi) the three heavy chain CDR sequences present in SEQ ID NO: 60 and the three light chain CDR sequences present in SEQ ID NO: 61; (xvii) the three heavy chain CDR sequences present in SEQ ID NO: 62 and the three light chain CDR sequences present in SEQ ID NO: 63; (xviii) the three heavy chain CDR sequences present in SEQ ID NO: 64 and the three light chain CDR sequences present in SEQ ID NO: 65; (xix) the three heavy chain CDR sequences present in SEQ ID NO: 66 and the three light chain CDR sequences present in SEQ ID NO: 67; (xx) the three heavy chain CDR sequences present in SEQ ID NO: 68 and the three light chain CDR sequences present in SEQ ID NO: 69; (xxi) the three heavy chain CDR sequences present in SEQ ID NO: 70 and the three light chain CDR sequences present in SEQ ID NO: 71; (xxii) the three heavy chain CDR sequences present in SEQ ID NO: 72 and the three light chain CDR sequences present in SEQ ID NO: 73; (xxiii) the three heavy chain CDR sequences present in SEQ ID NO: 74 and the three light chain CDR sequences present in SEQ ID NO: 75; or (xxiv) the three heavy chain CDR sequences present in SEQ ID NO: 76 and the three light chain CDR sequences present in SEQ ID NO: 77.

In some embodiments, the binding agent is a chimeric antigen receptor, where the chimeric antigen receptor includes an extracellular domain, a transmembrane domain, and an intracellular domain, where the extracellular domain includes an antibody or antigen-binding domain capable of binding to an antigen on an autoimmune cell, and where the intracellular domain includes a cytoplasmic signaling domain and one or more co-stimulatory domains. In some embodiments, the antigen-binding domain is an antigen-binding fragment selected from the group consisting of a Fab, a F(ab')$_2$ fragment, a scFV, a scAb, a dAb, a single domain heavy chain antibody, and a single domain light chain antibody. In some embodiments, the antigen-binding fragment is a scFv that is capable of binding to an antigen on an autoimmune cell or a cell adhesion molecule. In some embodiments, the cell adhesion molecule is MADCAM-1. In some embodiments, the antigen-binding fragment includes an amino acid sequence at least 80% identical to a sequence selected from the group of SEQ ID NOs: 6-29.

In some embodiments, the cytoplasmic signaling domain is a CD3 zeta domain. In some embodiments, the co-stimulatory domain includes at least one of a CD48, 4-1BB, ICOS, X-40, or CD27 domain.

In some embodiments, the vector further includes an additional nucleic acid sequence encoding a therapeutic gene product. In some embodiments, the additional nucleic sequence is operably linked a promoter. In some embodiments, the additional sequence is operably linked to the first nucleic acid sequence, or the second nucleic acid sequence. In some embodiments, the additional nucleic acid sequence is operably linked to the first nucleic acid sequence, the second nucleic acid sequence or the third nucleic acid sequence.

In some embodiments, the vector includes a viral vector selected from the group of a lentiviral vector, a retroviral vector, an adenoviral vector, or an adeno-associated viral (AAV) vector. In some embodiments, the viral vector is a lentiviral vector.

Also provided herein are compositions including any of the vectors described herein.

Also provided herein are methods of treating an autoimmune disease or disorder in a patient that include administering any of the T-cells described herein or any of the compositions described herein. In some embodiments, the subject is previously diagnosed or identified as having an autoimmune disease or disorder.

In some embodiments, the autoimmune disease or disorder is lupus, rheumatoid arthritis, multiple sclerosis, insulin dependent diabetes mellitus, myasthenia gravis, Graves disease, autoimmune hemolytic anemia, autoimmune thrombocytopenia purpura, Goodpasture's syndrome, pemphigus vulgaris, acute rheumatic fever, post-streptococcal glomerulonephritis, Crohn's disease, Celiac disease, or polyarteritis nodosa. In some embodiments, administering the autologous or allogenic T-cell population includes intravenous injection or intravenous infusion. In some embodiments, the administering results in amelioration of one or more symptoms of the autoimmune disease or disorder.

Also provided herein are polypeptides that include an antigen-binding domain that includes: an amino acid sequence at least 80% identical to a sequence selected from the group of SEQ ID NOs: 6-29. Also provided herein are polypeptides that include an antigen-binding domain that includes: (i) the three heavy chain CDR sequences present in SEQ ID NO: 30 and the three light chain CDR sequences present in SEQ ID NO: 31; (ii) the three heavy chain CDR sequences present in SEQ ID NO: 32 and the three light chain CDR sequences present in SEQ ID NO: 33; (iii) the three heavy chain CDR sequences present in SEQ ID NO: 34 and the three light chain CDR sequences present in SEQ ID NO: 35; (iv) the three heavy chain CDR sequences present in SEQ ID NO: 36 and the three light chain CDR sequences present in SEQ ID NO: 37; (v) the three heavy chain CDR sequences present in SEQ ID NO: 38 and the three light chain CDR sequences present in SEQ ID NO: 39; (vi) the three heavy chain CDR sequences present in SEQ ID NO: 40 and the three light chain CDR sequences present in SEQ ID NO: 41; (vii) the three heavy chain CDR sequences present in SEQ ID NO: 42 and the three light chain CDR sequences present in SEQ ID NO: 43; (viii) the three heavy chain CDR sequences present in SEQ ID NO: 44 and the three light chain CDR sequences present in SEQ ID NO: 45; (ix) the three heavy chain CDR sequences present in SEQ ID NO: 46 and the three light chain CDR sequences present in SEQ ID NO: 47; (x) the three heavy chain CDR sequences present in SEQ ID NO: 48 and the three light chain CDR sequences present in SEQ ID NO: 49; (xi) the three heavy chain CDR sequences present in SEQ ID NO: 50 and the three light chain CDR sequences present in SEQ ID NO: 51; (xii) the three heavy chain CDR sequences present in SEQ ID NO: 52 and the three light chain CDR sequences present in SEQ ID NO: 53; (xiii) the three heavy chain CDR sequences present in SEQ ID NO: 54 and the three light chain CDR sequences present in SEQ ID NO: 55; (xiv) the three heavy chain CDR sequences present in SEQ ID NO: 56 and the three light chain CDR sequences present in SEQ ID NO: 57; (xv) the three heavy chain CDR sequences present in SEQ ID NO: 58 and the three light chain CDR sequences present in SEQ ID NO: 59; (xvi) the three heavy chain CDR sequences present in SEQ ID NO: 60 and the three light chain CDR sequences present in SEQ ID NO: 61; (xvii) the three heavy chain CDR sequences present in SEQ ID NO: 62 and the three light chain CDR sequences present in SEQ ID NO: 63; (xviii) the three heavy chain CDR sequences present in SEQ ID NO: 64 and the three light chain CDR sequences present in SEQ ID NO: 65; (xix) the three heavy chain CDR sequences present in SEQ ID NO: 66 and the three light chain CDR sequences present in SEQ ID NO: 67; (xx) the three heavy chain CDR sequences present in SEQ ID NO: 68 and the three light chain CDR sequences present in SEQ ID NO: 69; (xxi) the three heavy chain CDR sequences present in SEQ ID NO: 70 and the three light chain CDR sequences present in SEQ ID NO: 71; (xxii) the three heavy chain CDR sequences present in SEQ ID NO: 72 and the three light chain CDR sequences present in SEQ ID NO: 73; (xxiii) the three heavy chain CDR sequences present in SEQ ID NO: 74 and the three light chain CDR sequences present in SEQ ID NO: 75; or (xxiv) the three heavy chain CDR sequences present in SEQ ID NO: 76 and the three light chain CDR sequences present in SEQ ID NO: 77.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
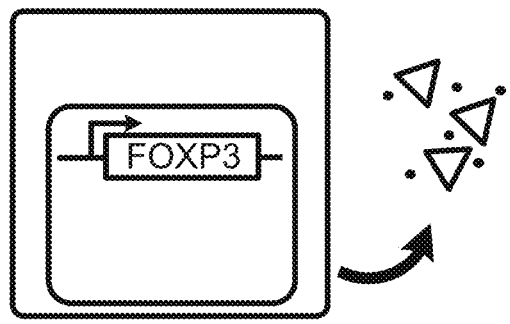
FIG. 1 is a diagram showing an exemplary T-cell with enforced expression of a FOXP3 polypeptide. Enforced expression of a FOXP3 polypeptide results in a core Treg suppressive program (e.g., IL-2 consumption and increase in CD25 expression, an increase in adenosine, an increase in CD39 expression, and expression of CTLA-4).

Provided herein are methods and materials that can be used to treat mammals identified as having an autoimmune disease. Provided herein are methods for increasing T-cell function that include introducing into a T-cell a first nucleic acid sequence encoding a FOXP3 polypeptide and a second nucleic acid sequence encoding a binding agent. Also provided are T-cells produced by any of the methods described herein. Also provided herein are T-cells that include: a first nucleic acid sequence encoding a FOXP3 polypeptide and a second nucleic acid sequence encoding a binding agent. Also provided herein are vectors that include a first nucleic acid sequence encoding a FOXP3 polypeptide and a second nucleic acid sequence encoding a binding agent. Also provided herein are methods and materials for treating a mammal having an autoimmune disease, where the methods include administering to the mammal an effective amount of a T-cell (e.g., any of the T-cells described herein).

FOXP3 Polypeptides

In some embodiments, a first nucleic acid sequence encoding a FOXP3 polypeptide having one or more mutations is introduced into a T-cell (e.g., CD4$^+$ T-cell, CD4$^+$ CD45RA$^+$ T-cell, CD4$^+$ CD62L$^+$ T-cell, or central memory T-cell). For example, a mutation in the first nucleic acid sequence encoding a FOXP3 polypeptide can include, without limitation, mutations that result in an amino acid substitution that changes the sub-cellular localization (e.g., increased nuclear localization) of the encoded FOXP3 polypeptide.

In some cases, a cell (e.g., a CD4$^+$ T-cell) with a FOXP3 polypeptide-dependent expression profile can have increased immunosuppressive function. For example, a cell transduced with a FOXP3 polypeptide having one or more amino acid substitutions, amino acid insertions, and/or amino acid substitutions as described herein can have increased expression of genes that are transcriptional targets of a FOXP3. Increased expression of these genes (e.g., 11-2, Ctla-4, and Tnfrsf18) can result in increased Treg cell function (e.g., inhibition of responder cell proliferation).

In some embodiments, a FOXP3 polypeptide can have one or more amino acid substitutions, amino acid insertions, and/or amino acid deletions within an amino acid sequence of exon 2. In some embodiments, the amino acid deletion includes deletion of all or part of the amino acid sequence corresponding to exon 2. In some embodiments, a FOXP3 polypeptide having the amino acid sequence corresponding to an exon 2-deleted from the FOXP3 polypeptide (FOXP3d2) can result in an increased nuclear localization of the FOXP3 polypeptide. FOXP3 polypeptides harboring any one or more amino acid deletions in the amino acid sequence exon 2 can sequestered to the nucleus (or show increased nuclear localization as compared to a FOXP3 polypeptide not including one or more amino acid deletions in the amino acid sequence of exon 2).

As used herein, "FOXP3" refers to the FOXP3 gene or protein that is a transcription factor in the Forkhead box (Fox) family of transcription factors (Sakaguchi et al., *Int'l Immun.* 21(10):1105-1111, 2009; Pandiyan, et al., *Cytokine* 76(1):13-24, 2015), or a variant thereof (e.g., a FOXP3 protein having one or more (e.g., one, two, three, four, five, six, seven, eight, nine, ten, eleven, twelve, thirteen, fourteen, fifteen, sixteen, seventeen, eighteen, nineteen, or twenty) amino acid substitutions, amino acid deletions, or amino acid insertions as compared to a wildtype FOXP3 protein). In some embodiments, when preparing a T-cell to be used in the treatment of a mammal having an autoimmune disease by administering to the mammal the T-cell, FOXP3 refers to human FOXP3 or a variant thereof. An example of a wildtype human FOXP3 polypeptide includes, without limitation, NCBI reference sequence: NP 001107849.1 or a functional fragment thereof.

In some embodiments referring to a FOXP3 polypeptide, the amino acid sequence of the FOXP3 polypeptide is at least 70% (e.g., at least 75%, at least 80%, at least 85%, at least 90%, at least 95%, at least 99%, or 100%) identical to:

```
                                        (SEQ ID NO: 1)
MPNPRPGKPSAPSLALGPSPGASPSWRAAPKASDL

LGARGPGGTFQGRDLRGGAHASSSSLNPMPPSQLQ

LPTLPLVMVAPSGARLGPLPHLQALLQDRPHFMHQ

LSTVDAHARTPVLQVHPLESPAMISLTPPTTATGV

FSLKARPGLPPGINVASLEWVSREPALLCTFPNPS

APRKDSTLSAVPQSSYPLLANGVCKWPGCEKVFEE

PEDFLKHCQADHLLDEKGRAQCLLQREMVQSLEQQ

LVLEKEKLSAMQAHLAGKMALTKASSVASSDKGSC

CIVAAGSQGPVVPAWSGPREAPDSLFAVRRHLWGS

HGNSTFPEFLHNMDYFKFHNMRPPFTYATLIRWAI

LEAPEKQRTLNEIYHWFTRMFAFFRNHPATWKNAI

RHNLSLHKCFVRVESEKGAVWTVDELEFRKKRSQR

PSRCSNPTPGP.
```

In some embodiments referring to a first nucleic acid sequence encoding a FOXP3 (e.g., full length FOXP3) polypeptide, the nucleic acid sequence is at least 70% (e.g., at least 75%, at least 80%, at least 85%, at least 90%, at least 95%, at least 99%, or 100%) identical to:

```
                                        (SEQ ID NO: 2)
ATGCCTAACCCCGCCCTGGAAAACCATCTGCCCC

TTCACTGGCCCTGGGACCTTCACCCGGAGCCTCAC

CATCTTGGAGAGCCGCCCCCAAGGCCAGCGACCTG

CTGGGAGCCAGAGGCCCCGGCGGCACCTTCCAGGG

CAGGGATCTGCGCGGCGGCGCCCACGCCAGCTCCT

CTAGCCTGAACCCCATGCCCCCTTCTCAGCTCCAG

CTGCCCACACTGCCCCTGGTCATGGTGGCACCTAG

CGGAGCAAGGCTGGGACCACTGCCACACCTCCAGG

CCCTGCTCCAGGACAGACCTCACTTTATGCACCAG

CTGTCCACCGTGGATGCACACGCAAGGACACCCGT

GCTCCAGGTGCACCCTCTGGAGTCTCCAGCCATGA

TCAGCCTGACCCCACCAACCACAGCAACAGGCGTG

TTCTCCCTGAAGGCCAGACCTGGCCTGCCTCCAGG

CATCAACGTGGCCTCCCTGGAGTGGGTGTCTAGGG

AGCCAGCCCTGCTGTGCACCTTTCCTAATCCATCT

GCCCCCCGCAAGGACTCCACACTGTCTGCCGTGCC

ACAGTCCTCTTACCCCCTGCTGGCCAACGGCGTGT

GCAAGTGGCCTGGCTGTGAGAAGGTGTTCGAGGAG

CCAGAGGATTTTCTGAAGCACTGCCAGGCCGACCA

CCTGCTGGATGAGAAGGGAAGGGCACAGTGTCTGC

TCCAGAGGGAGATGGTGCAGAGCCTGGAGCAGCAG

CTGGTGCTGGAGAAGGAGAAGCTGTCCGCCATGCA

GGCACACCTGGCAGGCAAGATGGCACTGACCAAGG

CCAGCTCCGTGGCCTCTAGCGACAAGGGCAGCTGC

TGTATCGTGGCCGCCGGCTCCCAGGGACCAGTGGT

GCCCGCCTGGTCTGGACCCAGGGAGGCACCTGACA

GCCTGTTCGCCGTGCGGAGACACCTGTGGGGCAGC

CACGGCAATTCCACCTTCCCCGAGTTTCTGCACAA

CATGGATTACTTCAAGTTTCACAATATGCGGCCCC

CTTTTACCTATGCCACACTGATCAGATGGGCCATC

CTGGAGGCCCCAGAGAAGCAGCGCACCCTGAACGA

AATCTACCACTGGTTCACACGGATGTTTGCCTTCT

TTAGAAATCACCCCGCCACCTGGAAGAACGCCATC

AGGCACAATCTGTCCCTGCACAAGTGTTTCGTGCG

CGTGGAGTCTGAGAAGGGCGCCGTGTGGACAGTGG

ATGAGCTGGAGTTCAGAAAGAAGAGAAGCCAGAGA

CCATCCAGGTGTTCAAACCCTACCCCAGGACCC.
```

In some embodiments, referring to a nucleic acid sequence encoding a FOXP3 polypeptide having a mutation in exon 2, the nucleic acid sequence corresponding to FOXP3 exon 2 is at least 80% (e.g., at least 85%, at least 90%, at least 95%, at least 99%, or 100%) identical to:

```
                                        (SEQ ID NO: 3)
CCTGCCCTTGGACAAGGACCCGATGCCCAACCCCA

GGCCTGGCAAGCCCTCGGCCCCTTCCTTGGCCCT

TGGCCCATCCCCAGGAGCCTCGCCCAGCTGGAGGG

CTGCACCCAAAGCCTCAGACCTGCTGGGGGCCCG

GGGCCCAGGGGGAACCTTCCAGGGCCGAGATCTT
```

```
-continued
CGAGGCGGGGCCCATGCCTCCTCTTCTTCCTTGAA

CCCCATGCCACCATCGCAGCTGCAG
```

In some embodiments referring to a nucleic acid sequence encoding a FOXP3 polypeptide having a deleted exon 2, the nucleic acid sequence that is deleted from full length FOXP3 polypeptide (SEQ ID NO: 2) is SEQ ID NO: 3 or a fragment of SEQ ID NO: 3.

Binding Agents

This document provides methods and materials for introducing into a T-cell (e.g., CD4+ T-cell, CD4+CD45RA+ T-cell, CD4+ CD62L+ T-cell, or central memory T-cell) a first nucleic acid sequence encoding a FOXP3 polypeptide (e.g., any of the exemplary FOXP3 polypeptides described herein) and a second nucleic acid sequence encoding a binding agent (e.g., any of the exemplary binding agents described herein). This document also provides methods and materials for introducing into a T-cell (e.g., CD4+ T-cell, CD4+CD45RA+ T-cell, CD4+ CD62L+ T-cell, or central memory T-cell) a first nucleic acid sequence encoding a FOXP3 polypeptide (e.g., any of the exemplary FOXP3 polypeptides described herein), a second nucleic acid sequence encoding a binding agent (e.g., any of the binding agents described herein), and a third nucleic acid sequence encoding a receptor polypeptide (e.g., any of the exemplary receptor polypeptides described herein). Also provided herein are methods and materials for introducing into a T-cell (e.g., CD4+ T-cells, CD4+CD45RA+ T-cells, CD4+ CD62L+ T-cell, or central memory T-cells) a first nucleic acid sequence encoding a FOXP3 polypeptide (e.g., any of the exemplary FOXP3 polypeptides described herein), a second nucleic acid sequence encoding a binding agent (e.g., any of the exemplary anti-MADCAM-1 antigen binding fragments), a third nucleic acid sequence encoding a receptor polypeptide (e.g., any of the exemplary polypeptides described herein), and a fourth nucleic acid sequence encoding a therapeutic gene product (e.g., any of the exemplary therapeutic gene products described herein).

In some embodiments, upon administering a T-cell that includes a binding agent (e.g., any of the binding agents described herein) to a subject, the binding agent enables the T-cell to home to a particular location or tissue in the subject. In some embodiments, upon administering a T-cell that includes a binding agent to a subject, the binding agent increases the ability of the T-cell to home to a particular location or tissue in the subject as compared to a T-cell that does not include the binding agent (i.e., a T-cell where the binding agent was not introduced into the cell). In some embodiments, the T-cell that includes the binding agent has increased (e.g., at least a 5% increase, at least a 10% increase, at least a 20% increase, at least a 30% increase, at least a 40% increase, at least a 50% increase, at least a 60% increase, at least a 70% increase, at least a 80% increase, at least a 90% increase, at least a 100% increase, at least a 120% increase, at least a 140% increase, at least a 160% increase, at least a 180% increase, or at least a 200% increase) homing to a particular location or tissue in the subject as compared to a T-cell that does not include the binding agent.

As used herein, "binding agent" refers to any of a variety of polypeptides that bind with specificity to its binding partner. In some embodiments, a T-cell (e.g., a CD4+ T-cell, a CD4+CD45RA+ T-cell, a CD4+ CD62L+ T-cell, or central memory T-cell) can be transduced with a nucleic acid sequence encoding a mutated FOXP3 polypeptide and a nucleic acid sequence encoding a binding agent as described herein and optionally, nucleic acid sequence(s) encoding a receptor polypeptide and/or a therapeutic gene product. In some embodiments, a binding agent can be any polypeptide that enhances the immunosuppressive effect of a T-cell (e.g., a CD4+ T-cell, a CD4+CD45RA+ T-cell, a CD4+ CD62L+ T-cell, or central memory T-cell).

In some embodiments, a binding agent can be a polypeptide that binds to molecules found specifically on autoimmune cells or tissues. In some embodiments, a binding agent can be a polypeptide that binds to molecules found specifically on endothelial cells. In some embodiments, a binding agent can be a polypeptide that binds to MADCAM-1. In some embodiments, MADCAM-1 is expressed on endothelial cells.

In some embodiments, a binding agent can be a chimeric antigen receptor (CAR) as described herein, where the CAR has an extracellular domain, a transmembrane domain, and an intracellular domain. In cases where the binding agent is a CAR, the extracellular domain includes a polypeptide capable of binding to a molecule found specifically on autoimmune cells or tissues, and the intracellular domain includes, e.g., a cytoplasmic signaling domain and one or more co-stimulatory domains. For example, the extracellular domain can include an scFv capable of binding to antigen on an autoimmune cell. In some embodiments, the scFv can bind to antigens found specifically on endothelial cells. In some embodiments, the scFv can bind to a polypeptide that binds to MADCAM-1.

As used herein, the term "chimeric antigen receptor" or "CAR" refers to a chimeric antigen receptor comprising an extraceullar domain, a transmembrane domain, and an intracellular domain. In some cases, the extracellular domain can comprise an antigen-binding domain as described herein. In some cases, the transmembrane domain can comprise a transmembrane domain derived from a natural polypeptide obtained from a membrane-binding or transmembrane protein. For example, a transmembrane domain can include, without limitation, a transmembrane domain from a T-cell receptor alpha or beta chain, a CD3 zeta chain, a CD28 polypeptide, or a CD8 polypeptide. In some cases, the intracellular domain can comprise a cytoplasmic signaling domain as described herein. In some cases, the intracellular domain can comprise a co-stimulatory domain as described herein.

In some embodiments, the CAR includes an extracellular domain having a scFv domain directed to MADCAM-1, a transmembrane domain, and an intracellular signaling domain. MADCAM-1 is expressed on endothelial cells and is responsive to numerous inflammatory mediators (see, e.g., Ando et al., *BMC Physiol.* 7:6331, 2007; Oshima et al., *Cell Physiol.* 281:C1096-C1105, 2001). MADCAM-1 can mediate both leukocyte adhesion and migration through the endothelium into tissues.

In some embodiments, the affinity of the anti-MADCAM-1 scFv is tuned to bind at high antigen density that exists in diseased tissues but avoid targeting healthy tissues with basal MADCAM-1 expression. In some embodiments, the MADCAM-1 scFv is coupled to a transmembrane domain which spans the membrane and is derived from a CD8 transmembrane domain (e.g., CD8a stalk and CD8a hinge). The intracellular signaling domain is comprised of the CD3zeta domain and an additional co-stimulatory domain such as CD28, 4-1BB, ICOS, OX-40, and/or CD27 to transmit a proliferative/survival signal upon antigen recognition.

In some embodiments, the antigen-binding domain is an antigen-binding fragment selected from the group consisting of a Fab, a F(ab')$_2$ fragment, a scFv, a scAb, a dAb, a single domain heavy chain antibody, and a single domain light chain antibody. In some embodiments, the antigen-binding fragment is a scFv that is capable of binding to an antigen on an autoimmune cell. In some embodiments, the scFv is capable of binding to a cell adhesion molecule. In some embodiments, the cell adhesion molecule is MADCAM-1. In some embodiments, the cytoplasmic signaling domain is a CD3 zeta domain. In some embodiments, the co-stimulatory domain comprises at least one of a CD28, 4-1BB, ICOS, X-40, or CD27 domain.

In some embodiments where the chimeric antigen receptor polypeptide includes a CD3 zeta cytoplasmic signaling domain, the CD3 zeta cytoplasmic signaling domain has an amino acid sequence that is at least 80% (e.g., at least 85%, at least 90%, at least 95%, at least 99%, or 100%) identical to:

```
                                        (SEQ ID NO: 4)
MKWKALFTAAILQAQLPITEAQSFGLLDPKLCYLL

DGILFIYGVILTALFLRVKFSRSADAPAYQQGQNQ

LYNELNLGRREEYDVLDKRRGRDPEMGGKPQRRKN

PQEGLYNELQKDKMAEAYSEIGMKGERRRGKGHDG

LYQGLSTATKDTYDALHMQALPPR
(NCBI Reference No.: NP_932170)
``` or a functional fragment thereof that has activating or stimulatory activity.

In some embodiments where the chimeric antigen receptor polypeptide includes a CD28 co-stimulatory domain, the CD28 co-stimulatory domain is at least 80% (e.g., at least 85%, at least 90%, at least 95%, at least 99%, or 100%) identical to:

```
                                        (SEQ ID NO: 5)
IEVMYPPPYLDNEKSNGTIIHVKGKHLCPSPLFPG

PSKPFWVLVVVGGVLACYSLLVTVAFIIFWVRSKR

SRLLHSDYMNMTPRRPGPTRKHYQPYAPPRDFAAY.
```

In some embodiments, a binding agent refers to an antibody, an antigen-binding domain, or an antigen-binding fragment thereof. As used herein, the term "antibody," "antigen-binding domain," or "antigen-binding fragment" refers to an intact immunoglobulin or to an antigen-binding portion thereof. In some embodiments, a binding agent refers to an intact immunoglobulin or to an antigen-binding portion thereof. Antigen-binding portions may be produced by recombinant DNA techniques or by enzymatic or chemical cleavage of intact antibodies. Examples of antigen-binding portions include Fab, Fab', F(ab')$_2$, Fv, domain antibodies (dAbs), and complementarity determining region (CDR) fragments, single-chain antibodies (scFv), chimeric antibodies, diabodies, triabodies, tetrabodies, and polypeptides that contain at least a portion of an immunoglobulin that is sufficient to confer specific antigen-binding to the polypeptide.

As used herein, the term "scFv" antibody fragments comprise the V$_H$ and V$_L$ domains of an antibody, wherein these domains are present in a single polypeptide chain. Included in the definition are single domain antibodies, including camelids. In some cases, the antibody or antigen-binding domain thereof is human or humanized.

As used herein, "T-cell function" refers to a T-cell's (e.g., any of the exemplary T-cells described herein) survival, stability, and/or ability to execute its intended function. For example, a CD4$^+$ T-cell can have an immunosuppressive function. A CD4$^+$ T-cell including a nucleic acid encoding a FOXP3 polypeptide can have a FOXP3-dependent expression profile that increases the immunosuppressive function of the T-cell. For example, a cell transduced with a mutated FOXP3 polypeptide as described herein can have increased expression of genes that are transcriptional targets of a FOXP3 that can result in increased Treg cell function.

As used herein, the term "activation" refers to induction of a signal on an immune cell (e.g., a B-cell or T-cell) that to results in initiation of the immune response (e.g., T-cell activation). In some cases, upon binding of an antigen to a T-cell receptor (TCR) or an exogenous chimeric antigen receptor (CAR), the immune cell can undergo changes in protein expression that result in the activation of the immune response. In some embodiments, upon activation of the CAR in T-cell (e.g., a T-cell that includes an exogenous FOXP3 polypeptide), the T-cell proliferates. In some cases, the proliferation of the T-cell following CAR activation is related to the signaling pathways activated CAR activation. In some cases, a TCR or CAR includes a cytoplasmic signaling sequence that can drive T-cell activation. For example, upon binding of the antigen, a chimeric antigen receptor comprising an intracellular domain that includes a cytoplasmic signaling sequence (e.g., an immune-receptor tyrosine-based inhibition motifs (ITAM)) that can be phosphorylated. A phosphorylated ITAM results in the induction of a T-cell activation pathway that ultimately results in a T-cell immune response. Examples of ITAMs include, without limitation, CD3 gamma, CD3 delta, CD3 epsilon, TCR zeta, FcR gamma, FcR beta, CD5, CD22, CD79a, and CD66d.

As used herein, the term "stimulation" refers to stage of TCR or CAR signaling where a co-stimulatory signal can be used to achieve a robust and sustained TCR or CAR signaling response. As described herein, a co-stimulatory domain can be referred to as a signaling domain. In some cases, a signaling domain (e.g., co-stimulatory domain) can be a CD27, CD28, OX40, CD30, CD40, B7-H3, NKG2C, LIGHT, CD7, CD2, 4-1BB, or PD-1.

As used herein, the terms "binding," "binds," or "specifically binds" in the context of the binding of an antibody or antigen binding fragment to a target antigen typically is a binding with an affinity corresponding to a K$_D$ of about $10^{-8}$ M or less (e.g., about $10^{-6}$ M or less, about $10^{-8}$ M or less, about $10^{-8}$ M or less, or about $10^{-9}$ M or less) when determined by surface plasmon resonance (SPR). As used herein, the term "K$_D$" (M) refers to the dissociation equilibrium constant of a particular antibody-antigen interaction.

In some embodiments, any of the "antigen-binding domains," "antibodies," or "binding agents" further include a secretion signal peptide. For example, a nucleic acid sequence encoding a binding agent further includes a nucleic acid sequence encoding a secretion signal peptide. In some embodiments, a binding agent includes, without limitation, an antibody or antigen-binding fragment (e.g., a scFv) capable of binding to a cell adhesion molecule (e.g., without limitation, MADCAM-1).

As used herein, MADCAM-1 refers to mucosal addressin cell adhesion molecule 1 polypeptide. When preparing the T-cell or treating a mammal with the T-cell, MADCAM-1 refers to human MADCAM-1. An example of a human MADCAM-1 polypeptide includes, without limitation, NCBI reference sequence: NP_570116.2, or NP_570118.1, or a fragment thereof. In some embodiments, an anti-MADCAM-1 antibody or antigen-binding domain or an antigen-binding fragment thereof exhibits a binding affinity to MADCAM-1 that enables binding to and extravasation of the T-cell from the circulation into a tissue. The affinity of the anti-MADCAM-1 antibody or antibody binding fragment scFv is selected to bind to cells that express at high MADCAM-1 density that exists in diseased tissues but avoid targeting healthy tissues with basal MADCAM-1 expression.

In some embodiments, the antigen-binding domain or antigen-binding fragment comprises an amino acid sequence at least 80% (e.g., at least 85%, at least 90%, at least 95%, at least 99%, or 100%) identical to a sequence selected from the group of SEQ ID NOs: 6-29. In some embodiments, the antigen-binding fragment comprising a sequence selected from the group SEQ ID NOs: 6-29 is altered to introduce one or more amino acid substitutions, insertions, or deletions. For example, the antigen-binding fragment selected from the group of SEQ ID NOs: 6-29 is mutated in such a manner as to enable increased binding affinity to a target antigen as compared to the binding affinity to an antigen that is not the target antigen. In another example, the antigen-binding fragment selected from the group of SEQ ID NOs: 6-29 is mutated in such a manner as to decrease binding affinity to a target antigen as compared to the binding affinity to an antigen that is not the target antigen. In some cases, the one or more amino acid substitutions, insertions, or deletions are located within a CDR region of the antigen-binding fragment. In some cases, one or more, two or more, three or more, four or more, five or more or six CDR regions include one or more amino acid substitutions, insertions, or deletions, as compared to the "non-altered" amino acid sequence (e.g., amino acid sequences as shown in SEQ ID NOs: 6-29).

As used herein, the term "variable region" or "variable domain" can refers to the domain of an antibody heavy or light chain that is involved in binding the antibody to antigen. The variable regions of the heavy chain and light chain of an antibody may be further subdivided into complementarity-determining regions (CDRs) and interspersed with regions that are more conserved, termed framework regions (FRs). The terms "complementarity determining regions" and "CDRs," are known in the art to refer to non-contiguous sequences of amino acids within antibody variable regions, which confer antigen specificity and/or binding affinity.

In some embodiments, the antigen-binding domain includes a heavy chain variable domain that includes an amino acid sequence at least 80% (e.g., at least 85%, at least 90%, at least 95%, at least 99%, or 100%) identical to SEQ ID NOs: 30, 32, 34, 36, 38, 40, 42, 44, 46, 48, 50, 52, 54, 56, 58, 60, 62, 64, 66, 68, 70, 72, 74, or 76. In some embodiments, the antigen-binding domain includes a light chain variable domain that includes an amino acid sequence at least 80% (e.g., at least 85%, at least 90%, at least 95%, at least 99%, or 100%) identical to SEQ ID NOs: 31, 33, 35, 37, 39, 41, 43, 45, 47, 49, 51, 53, 55, 57, 59, 61, 63, 65, 67, 69, 71, 73, 75, or 77.

In some embodiments, the antigen-binding domain or antigen-binding fragment includes:
a heavy chain variable domain comprising a sequence that is at least 80% (e.g., at least 85%, at least 90%, at least 95%, at least 99%, or 100%) identical to SEQ ID NO: 30 and a light chain variable domain comprising a sequence that is at least 80% (e.g., at least 85%, at least 90, at least 95%, at least 99%, or 100%) identical to SEQ ID NO: 31;
a heavy chain variable domain comprising a sequence that is at least 80% (e.g., at least 85%, at least 90%, at least 95%, at least 99%, or 100%) identical to SEQ ID NO: 32 and a light chain variable domain comprising a sequence that is at least 80% (e.g., at least 85%, at least 90, at least 95%, at least 99%, or 100%) identical to SEQ ID NO: 33;
a heavy chain variable domain comprising a sequence that is at least 80% (e.g., at least 85%, at least 90%, at least 95%, at least 99%, or 100%) identical to SEQ ID NO: 34 and a light chain variable domain comprising a sequence that is at least 80% (e.g., at least 85%, at least 90, at least 95%, at least 99%, or 100%) identical to SEQ ID NO: 35;
a heavy chain variable domain comprising a sequence that is at least 80% (e.g., at least 85%, at least 90%, at least 95%, at least 99%, or 100%) identical to SEQ ID NO: 36 and a light chain variable domain comprising a sequence that is at least 80% (e.g., at least 85%, at least 90, at least 95%, at least 99%, or 100%) identical to SEQ ID NO: 37;
a heavy chain variable domain comprising a sequence that is at least 80% (e.g., at least 85%, at least 90%, at least 95%, at least 99%, or 100%) identical to SEQ ID NO: 38 and a light chain variable domain comprising a sequence that is at least 80% (e.g., at least 85%, at least 90, at least 95%, at least 99%, or 100%) identical to SEQ ID NO: 39;
a heavy chain variable domain comprising a sequence that is at least 80% (e.g., at least 85%, at least 90%, at least 95%, at least 99%, or 100%) identical to SEQ ID NO: 40 and a light chain variable domain comprising a sequence that is at least 80% (e.g., at least 85%, at least 90, at least 95%, at least 99%, or 100%) identical to SEQ ID NO: 41;
a heavy chain variable domain comprising a sequence that is at least 80% (e.g., at least 85%, at least 90%, at least 95%, at least 99%, or 100%) identical to SEQ ID NO: 42 and a light chain variable domain comprising a sequence that is at least 80% (e.g., at least 85%, at least 90, at least 95%, at least 99%, or 100%) identical to SEQ ID NO: 43;
a heavy chain variable domain comprising a sequence that is at least 80% (e.g., at least 85%, at least 90%, at least 95%, at least 99%, or 100%) identical to SEQ ID NO: 44 and a light chain variable domain comprising a sequence that is at least 80% (e.g., at least 85%, at least 90, at least 95%, at least 99%, or 100%) identical to SEQ ID NO: 45;
a heavy chain variable domain comprising a sequence that is at least 80% (e.g., at least 85%, at least 90%, at least 95%, at least 99%, or 100%) identical to SEQ ID NO: 46 and a light chain variable domain comprising a sequence that is at least 80% (e.g., at least 85%, at least 90, at least 95%, at least 99%, or 100%) identical to SEQ ID NO: 47;
a heavy chain variable domain comprising a sequence that is at least 80% (e.g., at least 85%, at least 90%, at least 95%, at least 99%, or 100%) identical to SEQ ID NO: 48 and a light chain variable domain comprising a sequence that is at least 80% (e.g., at least 85%, at least 90, at least 95%, at least 99%, or 100%) identical to SEQ ID NO: 49;

a heavy chain variable domain comprising a sequence that is at least 80% (e.g., at least 85%, at least 90%, at least 95%, at least 99%, or 100%) identical to SEQ ID NO: 50 and a light chain variable domain comprising a sequence that is at least 80% (e.g., at least 85%, at least 90, at least 95%, at least 99%, or 100%) identical to SEQ ID NO: 51;

a heavy chain variable domain comprising a sequence that is at least 80% (e.g., at least 85%, at least 90%, at least 95%, at least 99%, or 100%) identical to SEQ ID NO: 52 and a light chain variable domain comprising a sequence that is at least 80% (e.g., at least 85%, at least 90, at least 95%, at least 99%, or 100%) identical to SEQ ID NO: 53;

a heavy chain variable domain comprising a sequence that is at least 80% (e.g., at least 85%, at least 90%, at least 95%, at least 99%, or 100%) identical to SEQ ID NO: 54 and a light chain variable domain comprising a sequence that is at least 80% (e.g., at least 85%, at least 90, at least 95%, at least 99%, or 100%) identical to SEQ ID NO: 55;

a heavy chain variable domain comprising a sequence that is at least 80% (e.g., at least 85%, at least 90%, at least 95%, at least 99%, or 100%) identical to SEQ ID NO: 56 and a light chain variable domain comprising a sequence that is at least 80% (e.g., at least 85%, at least 90, at least 95%, at least 99%, or 100%) identical to SEQ ID NO: 57;

a heavy chain variable domain comprising a sequence that is at least 80% (e.g., at least 85%, at least 90%, at least 95%, at least 99%, or 100%) identical to SEQ ID NO: 58 and a light chain variable domain comprising a sequence that is at least 80% (e.g., at least 85%, at least 90, at least 95%, at least 99%, or 100%) identical to SEQ ID NO: 59;

a heavy chain variable domain comprising a sequence that is at least 80% (e.g., at least 85%, at least 90%, at least 95%, at least 99%, or 100%) identical to SEQ ID NO: 60 and a light chain variable domain comprising a sequence that is at least 80% (e.g., at least 85%, at least 90, at least 95%, at least 99%, or 100%) identical to SEQ ID NO: 61;

a heavy chain variable domain comprising a sequence that is at least 80% (e.g., at least 85%, at least 90%, at least 95%, at least 99%, or 100%) identical to SEQ ID NO: 62 and a light chain variable domain comprising a sequence that is at least 80% (e.g., at least 85%, at least 90, at least 95%, at least 99%, or 100%) identical to SEQ ID NO: 63;

a heavy chain variable domain comprising a sequence that is at least 80% (e.g., at least 85%, at least 90%, at least 95%, at least 99%, or 100%) identical to SEQ ID NO: 64 and a light chain variable domain comprising a sequence that is at least 80% (e.g., at least 85%, at least 90, at least 95%, at least 99%, or 100%) identical to SEQ ID NO: 65;

a heavy chain variable domain comprising a sequence that is at least 80% (e.g., at least 85%, at least 90%, at least 95%, at least 99%, or 100%) identical to SEQ ID NO: 66 and a light chain variable domain comprising a sequence that is at least 80% (e.g., at least 85%, at least 90, at least 95%, at least 99%, or 100%) identical to SEQ ID NO: 67;

a heavy chain variable domain comprising a sequence that is at least 80% (e.g., at least 85%, at least 90%, at least 95%, at least 99%, or 100%) identical to SEQ ID NO: 68 and a light chain variable domain comprising a sequence that is at least 80% (e.g., at least 85%, at least 90, at least 95%, at least 99%, or 100%) identical to SEQ ID NO: 69;

a heavy chain variable domain comprising a sequence that is at least 80% (e.g., at least 85%, at least 90%, at least 95%, at least 99%, or 100%) identical to SEQ ID NO: 70 and a light chain variable domain comprising a sequence that is at least 80% (e.g., at least 85%, at least 90, at least 95%, at least 99%, or 100%) identical to SEQ ID NO: 71;

a heavy chain variable domain comprising a sequence that is at least 80% (e.g., at least 85%, at least 90%, at least 95%, at least 99%, or 100%) identical to SEQ ID NO: 72 and a light chain variable domain comprising a sequence that is at least 80% (e.g., at least 85%, at least 90, at least 95%, at least 99%, or 100%) identical to SEQ ID NO: 73;

a heavy chain variable domain comprising a sequence that is at least 80% (e.g., at least 85%, at least 90%, at least 95%, at least 99%, or 100%) identical to SEQ ID NO: 74 and a light chain variable domain comprising a sequence that is at least 80% (e.g., at least 85%, at least 90, at least 95%, at least 99%, or 100%) identical to SEQ ID NO: 75; or a heavy chain variable domain comprising a sequence that is at least 80% (e.g., at least 85%, at least 90%, at least 95%, at least 99%, or 100%) identical to SEQ ID NO: 76 and a light chain variable domain comprising a sequence that is at least 80% (e.g., at least 85%, at least 90, at least 95%, at least 99%, or 100%) identical to SEQ ID NO: 77.

In some embodiments, the antigen-binding domain or antigen-binding fragment includes an (i) the three heavy chain CDR sequences present in SEQ ID NO: 30 and the three light chain CDR sequences present in SEQ ID NO: 31; (ii) the three heavy chain CDR sequences present in SEQ ID NO: 32 and the three light chain CDR sequences present in SEQ ID NO: 33; (iii) the three heavy chain CDR sequences present in SEQ ID NO: 34 and the three light chain CDR sequences present in SEQ ID NO: 35; (iv) the three heavy chain CDR sequences present in SEQ ID NO: 36 and the three light chain CDR sequences present in SEQ ID NO: 37; (v) the three heavy chain CDR sequences present in SEQ ID NO: 38 and the three light chain CDR sequences present in SEQ ID NO: 39; (vi) the three heavy chain CDR sequences present in SEQ ID NO: 40 and the three light chain CDR sequences present in SEQ ID NO: 41; (vii) the three heavy chain CDR sequences present in SEQ ID NO: 42 and the three light chain CDR sequences present in SEQ ID NO: 43; (viii) the three heavy chain CDR sequences present in SEQ ID NO: 44 and the three light chain CDR sequences present in SEQ ID NO: 45; (ix) the three heavy chain CDR sequences present in SEQ ID NO: 46 and the three light chain CDR sequences present in SEQ ID NO: 47; (x) the three heavy chain CDR sequences present in SEQ ID NO: 48 and the three light chain CDR sequences present in SEQ ID NO: 49; (xi) the three heavy chain CDR sequences present in SEQ ID NO: 50 and the three light chain CDR sequences present in SEQ ID NO: 51; (xii) the three heavy chain CDR sequences present in SEQ ID NO: 52 and the three light chain CDR sequences present in SEQ ID NO: 53; (xiii) the three heavy chain CDR sequences present in SEQ ID NO: 54 and the three light chain CDR sequences present in SEQ ID NO: 55; (xiv) the three heavy chain CDR sequences present in SEQ ID NO: 56 and the three light chain CDR sequences present in SEQ ID NO: 57; (xv) the three heavy chain CDR sequences present in SEQ ID NO: 58 and the three light chain CDR sequences present in SEQ ID NO: 59; (xvi) the three heavy chain CDR sequences present in SEQ ID NO: 60 and the three light chain CDR sequences present in SEQ ID NO: 61; (xvii) the three heavy chain CDR sequences present in SEQ ID NO: 62 and the three light chain CDR sequences present in SEQ ID NO: 63; (xviii) the three heavy chain CDR sequences present in SEQ ID NO: 64 and the three light chain CDR sequences present in SEQ ID NO: 65; (xix) the three heavy chain CDR sequences present in SEQ ID NO: 66 and the three light chain CDR sequences present in SEQ ID NO: 67; (xx) the three heavy chain CDR sequences present in SEQ ID NO: 68 and the three light chain CDR sequences present in SEQ ID NO: 69; (xxi) the three heavy chain CDR sequences present in SEQ ID NO: 70 and the three light chain CDR sequences present in SEQ ID NO: 71; (xxii) the three heavy chain CDR sequences present in SEQ ID NO: 72 and the three light chain CDR sequences present in SEQ ID NO: 73; (xxiii) the three heavy chain CDR sequences present in SEQ ID NO: 74 and the three light chain CDR sequences present in SEQ ID NO: 75; or (xxiv) the three heavy chain CDR sequences present in SEQ ID NO: 76 and the three light chain CDR sequences present in SEQ ID NO: 77.

In some embodiments, an anti-MADCAM-1 antibody or antigen-binding domain or antigen-binding fragment thereof may also be described or specified in terms of their binding affinity to MADCAM-1 (e.g., human MADCAM-1). In some embodiments, preferred binding affinities to MAD-CAM-1 include those with a dissociation constant or $K_D$ of no greater than 1 nM, 2 nM, 3 nM, 4 nM, 5 nM, 6 nM, 7 nM, 8 nM, 9 nM, 10 nM, 15 nM, 20 nM, 25 nM, 30 nM, 40 nM, 50 nM, 60 nM, 70 nM, 80 nM, 90 nM, 100 nM, 110 nM, 120 nM, 130 nM, 140 nM, 150 nM, 200 nM, 250 nM, 300 nM, 400 nM, 500 nM, 600 nM, 700 nM, 800 nM, 900 nM, 1000 nM, 1100 nM, 1200 nM, 1300 nM, 1400 nM, 1500 nM, 1600 nM, 1700 nM, 1800 nM, 1900 nM, or 2000 nM. In some embodiments, an anti-MADCAM-1 antibody or antigen-binding domain or antigen-binding fragment thereof exhibits a binding affinity ($K_D$) to MADCAM-1 that is between about 10 nM to about 1000 nM (e.g., about 10 nM to about 950 nM, about 10 nM to about 900 nM, about 10 nM to about 850 nM, about 10 nM to about 800 nM, about 10 nM to about 750 nM, about 10 nM to about 700 nM, about 10 nM to about 650 nM, about 10 nM to about 600 nM, about 10 nM to about 550 nM, about 10 nM to about 500 nM, about 10 nM to about 450 nM, about 10 nM to about 400 nM, about 10 nM to about 350 nM, about 10 nM to about 300 nM, about 10 nM to about 250 nM, about 10 nM to about 200 nM, about 10 nM to about 200 nM, about 10 nM to about 150 nM, about 10 nm to about 100 nM, about 10 nM to about 50 nm, about 50 nM to about 950 nM, about 50 nM to about 900 nM, about 50 nM to about 850 nM, about 50 nM to about 800 nM, about 50 nM to about 750 nM, about 50 nM to about 700 nM, about 50 nM to about 650 nM, about 50 nM to about 600 nM, about 50 nM to about 550 nM, about 50 nM to about 500 nM, about 50 nM to about 450 nM, about 50 nM to about 400 nM, about 50 nM to about 350 nM, about 50 nM to about 300 nM, about 50 nM to about 250 nM, about 50 nM to about 200 nM, about 50 nM to about 200 nM, about 50 nM to about 150 nM, about 50 nm to about 100 nM, about 100 nM to about 1000 nM, about 100 nM to about 950 nM, about 100 nM to about 900 nM, about 100 nM to about 850 nM, about 100 nM to about 800 nM, about 100 nM to about 750 nM, about 100 nM to about 700 nM, about 100 nM to about 650 nM, about 100 nM to about 600 nM, about 100 nM to about 550 nM, about 100 nM to about 500 nM, about 100 nM to about 450 nM, about 100 nM to about 400 nM, about 100 nM to about 350 nM, about 100 nM to about 300 nM, about 100 nM to about 250 nM, about 100 nM to about 200 nM, about 100 nM to about 200 nM, about 100 nM to about 150 nM, about 150 nM to about 1000 nM, about 150 nM to about 950 nM, about 150 nM to about 900 nM, about 150 nM to about 850 nM, about 150 nM to about 800 nM, about 150 nM to about 750 nM, about 150 nM to about 700 nM, about 150 nM to about 650 nM, about 150 nM to about 600 nM, about 150 nM to about 550 nM, about 150 nM to about 500 nM, about 150 nM to about 450 nM, about 150 nM to about 400 nM, about 150 nM to about 350 nM, about 150 nM to about 300 nM, about 150 nM to about 250 nM, about 150 nM to about 200 nM, about 200 nM to about 1000 nM, about 200 nM to about 950 nM, about 200 nM to about 900 nM, about 200 nM to about 850 nM, about 200 nM to about 800 nM, about 200 nM to about 750 nM, about 200 nM to about 700 nM, about 200 nM to about 650 nM, about 200 nM to about 600 nM, about 200 nM to about 550 nM, about 200 nM to about 500 nM, about 200 nM to about 450 nM, about 200 nM to about 400 nM, about 200 nM to about 350 nM, about 200 nM to about 300 nM, about 200 nM to about 250 nM, about 250 nM to about 1000 nM, about 250 nM to about 950 nM, about 250 nM to about 900 nM, about 250 nM to about 850 nM, about 250 nM to about 800 nM, about 250 nM to about 750 nM, about 250 nM to about 700 nM, about 250 nM to about 650 nM, about 250 nM to about 600 nM, about 250 nM to about 550 nM, about 250 nM to about 500 nM, about 250 nM to about 450 nM, about 250 nM to about 400 nM, about 250 nM to about 350 nM, about 250 nM to about 300 nM, about 300 nM to about 1000 nM, about 300 nM to about 950 nM, about 300 nM to about 900 nM, about 300 nM to about 850 nM, about 300 nM to about 800 nM, about 300 nM to about 750 nM, about 300 nM to about 700 nM, about 300 nM to about 650 nM, about 300 nM to about 600 nM, about 300 nM to about 550 nM, about 300 nM to about 500 nM, about 300 nM to about 450 nM, about 300 nM to about 400 nM, about 300 nM to about 350 nM, about 350 nM to about 1000 nM, about 350 nM to about 950 nM, about 350 nM to about 900 nM, about 350 nM to about 850 nM, about 350 nM to about 800 nM, about 350 nM to about 750 nM, about 350 nM to about 700 nM, about 350 nM to about 650 nM, about 350 nM to about 600 nM, about 350 nM to about 550 nM, about 350 nM to about 500 nM, about 350 nM to about 450 nM, about 350 nM to about 400 nM, about 400 nM to about 1000 nM, about 400 nM to about 950 nM, about 400 nM to about 900 nM, about 400 nM to about 850 nM, about 400 nM to about 800 nM, about 400 nM to about 750 nM, about 400 nM to about 700 nM, about 400 nM to about 650 nM, about 400 nM to about 600 nM, about 400 nM to about 550 nM, about 400 nM to about 500 nM, about 400 nM to about 450 nM, about 450 nM to about 1000 nM, about 450 nM to about 950 nM, about 450 nM to about 900 nM, about 450 nM to about 850 nM, about 450 nM to about 800 nM, about 450 nM to about 750 nM, about 450 nM to about 700 nM, about 450 nM to about 650 nM, about 450 nM to about 600 nM, about 450 nM to about 550 nM, about 450 nM to about 500 nM, about 500 nM to about 1000 nM, about 500 nM to about 950 nM, about 500 nM to about 900 nM, about 500 nM to about 850 nM, about 500 nM to about 800 nM, about 500 nM to about 750 nM, about 500 nM to about 700 nM, about 500 nM to about 650 nM, about 500 nM to about 600 nM, about 500 nM to about 550 nM, about 550 nM to about 1000 nM, about 550 nM to about 950 nM, about 550 nM to about 900 nM, about 550 nM to about 850 nM, about 550 nM to about 800 nM, about 550 nM to about 750 nM, about 550 nM to about 700 nM, about 550 nM to about 650 nM, about 550 nM to about 600 nM, about 600 nM to about 1000 nM, about 600 nM to about 950 nM, about 600 nM to about 900 nM, about 600 nM to about 850 nM, about 600 nM to about 800 nM, about 600 nM to about 750 nM, about 600 nM to about 700 nM, about 600 nM to about 650 nM, about 650 nM to about 1000 nM, about 650 nM to about 950 nM, about 650 nM to about 900 nM, about 650 nM to about 850 nM, about 650 nM to about 800 nM, about 650 nM to about 750 nM, about 650 nM to about 700 nM, about 700 nM to about 1000 nM, about 700 nM to about 950 nM, about 700 nM to about 900 nM, about 700 nM to about 850 nM, about 700 nM to about 800 nM, about 700 nM to about 750 nM, about 750 nM to about 1000 nM, about 750 nM to about 950 nM, about 750 nM to about 900 nM, about 750 nM to about 850 nM, about 750 nM to about 800 nM, about 800 nM to about 1000 nM, about 800 nM to about 950 nM, about 800 nM to about 900 nM, about 800 nM to about 850 nM, about 850 nM to about 1000 nM, about 850 nM to about 950 nM, about 850 nM to about 900 nM, or about 900 to about 950 nM) (e.g., as measured by SPR).

In some embodiments, an anti-MADCAM-1 antibody or antigen-binding domain or antigen-binding fragment thereof exhibits a binding affinity ($K_D$) to MADCAM-1 that is between about 0.1 nM to about 10 nM (e.g., about 0.1 nM to about 9 nM, about 0.1 nM to about 8 nM, about 0.1 nM to about 7 nM, about 0.1 nM to about 6 nM, about 0.1 nM to about 5 nM, about 0.1 nM to about 4 nM, about 0.1 nM to about 3 nM, about 0.1 nM to about 2 nM, about 0.1 nM to about 1 nM, about 0.1 nM to about 0.9 nM, about 0.1 nM to about 0.8 nM, about 0.1 nM to about 0.7 nM, about 0.1 nM to about 0.6 nM, about 0.1 nM to about 0.5 nM, about 0.1 nM to about 0.4 nM, about 0.1 nM to about 0.3 nM, about 0.1 nM to about 0.2 nM, about 0.2 nM to about 10 nM, about 0.2 nM to about 9 nM, about 0.2 nM to about 8 nM, about 0.2 nM to about 7 nM, about 0.2 nM to about 6 nM, about 0.2 nM to about 5 nM, about 0.2 nM to about 4 nM, about 0.2 nM to about 3 nM, about 0.2 nM to about 2 nM, about 0.2 nM to about 1 nM, about 0.2 nM to about 0.9 nM, about 0.2 nM to about 0.8 nM, about 0.2 nM to about 0.7 nM, about 0.2 nM to about 0.6 nM, about 0.2 nM to about 0.5 nM, about 0.2 nM to about 0.4 nM, about 0.2 nM to about 0.3 nM, about 0.3 nM to about 10 nM, about 0.3 nM to about 9 nM, about 0.3 nM to about 8 nM, about 0.3 nM to about 7 nM, about 0.3 nM to about 6 nM, about 0.3 nM to about 5 nM, about 0.3 nM to about 4 nM, about 0.3 nM to about 3 nM, about 0.3 nM to about 2 nM, about 0.3 nM to about 1 nM, about 0.3 nM to about 0.9 nM, about 0.3 nM to about 0.8 nM, about 0.3 nM to about 0.7 nM, about 0.3 nM to about 0.6 nM, about 0.3 nM to about 0.5 nM, about 0.3 nM to about 0.4 nM, about 0.4 nM to about 10 nM, about 0.4 nM to about 9 nM, about 0.4 nM to about 8 nM, about 0.4 nM to about 7 nM, about 0.4 nM to about 6 nM, about 0.4 nM to about 5 nM, about 0.4 nM to about 4 nM, about 0.4 nM to about 3 nM, about 0.4 nM to about 2 nM, about 0.4 nM to about 1 nM, about 0.4 nM to about 0.9 nM, about 0.4 nM to about 0.8 nM, about 0.4 nM to about 0.7 nM, about 0.4 nM to about 0.6 nM, about 0.4 nM to about 0.5 nM, about 0.5 nM to about 10 nM, about 0.5 nM to about 9 nM, about 0.5 nM to about 8 nM, about 0.5 nM to about 7 nM, about 0.5 nM to about 6 nM, about 0.5 nM to about 5 nM, about 0.5 nM to about 4 nM, about 0.5 nM to about 3 nM, about 0.5 nM to about 2 nM, about 0.5 nM to about 1 nM, about 0.5 nM to about 0.9 nM, about 0.5 nM to about 0.8 nM, about 0.5 nM to about 0.7 nM, about 0.5 nM to about 0.6 nM, about 0.6 nM to about 10 nM, about 0.6 nM to about 9 nM, about 0.6 nM to about 8 nM, about 0.6 nM to about 7 nM, about 0.6 nM to about 6 nM, about 0.6 nM to about 5 nM, about 0.6 nM to about 4 nM, about 0.6 nM to about 3 nM, about 0.6 nM to about 2 nM, about 0.6 nM to about 1 nM, about 0.6 nM to about 0.9 nM, about 0.6 nM to about 0.8 nM, about 0.6 nM to about 0.7 nM, about 0.7 nM to about 10 nM, about 0.7 nM to about 9 nM, about 0.7 nM to about 8 nM, about 0.7 nM to about 7 nM, about 0.7 nM to about 6 nM, about 0.7 nM to about 5 nM, about 0.7 nM to about 4 nM, about 0.7 nM to about 3 nM, about 0.7 nM to about 2 nM, about 0.7 nM to about 1 nM, about 0.7 nM to about 0.9 nM, about 0.7 nM to about 0.8 nM, about 0.8 nM to about 10 nM, about 0.8 nM to about 9 nM, about 0.8 nM to about 8 nM, about 0.8 nM to about 7 nM, about 0.8 nM to about 6 nM, about 0.8 nM to about 5 nM, about 0.8 nM to about 4 nM, about 0.8 nM to about 3 nM, about 0.8 nM to about 2 nM, about 0.8 nM to about 1 nM, about 0.8 nM to about 0.9 nM, about 0.9 nM to about 10 nM, about 0.9 nM to about 9 nM, about 0.9 nM to about 8 nM, about 0.9 nM to about 7 nM, about 0.9 nM to about 6 nM, about 0.9 nM to about 5 nM, about 0.9 nM to about 4 nM, about 0.9 nM to about 3 nM, about 0.9 nM to about 2 nM, about 0.9 nM to about 1 nM, about 1 nM to about 10 nM, about 1 nM to about 9 nM, about 1 nM to about 8 nM, about 1 nM to about 7 nM, about 1 nM to about 6 nM, about 1 nM to about 5 nM, about 1 nM to about 4 nM, about 1 nM to about 3 nM, about 1 nM to about 2 nM, about 2 nM to about 10 nM, about 2 nM to about 9 nM, about 2 nM to about 8 nM, about 2 nM to about 7 nM, about 2 nM to about 6 nM, about 2 nM to about 5 nM, about 2 nM to about 4 nM, about 2 nM to about 3 nM, about 3 nM to about 10 nM, about 3 nM to about 9 nM, about 3 nM to about 8 nM, about 3 nM to about 7 nM, about 3 nM to about 6 nM, about 3 nM to about 5 nM, about 3 nM to about 4 nM, about 4 nM to about 10 nM, about 4 nM to about 9 nM, about 4 nM to about 8 nM, about 4 nM to about 7 nM, about 4 nM to about 6 nM, about 4 nM to about 5 nM, about 5 nM to about 10 nM, about 5 nM to about 9 nM, about 5 nM to about 8 nM, about 5 nM to about 7 nM, about 5 nM to about 6 nM, about 6 nM to about 10 nM, about 6 nM to about 9 nM, about 6 nM to about 8 nM, about 6 nM to about 7 nM, about 7 nM to about 10 nM, about 7 nM to about 9 nM, about 7 nM to about 8 nM, about 8 nM to about 10 nM, about 8 nM to about 9 nM, or about 9 nM to about 10 nM) (e.g., as measured by SPR).

In some embodiments, an anti-MADCAM-1 antibody or antigen-binding domain or antigen-binding fragment thereof exhibits a binding affinity ($K_D$) to MADCAM-1 that is between about 1000 nM to about 2000 nM (e.g., about 1000 nM to about 1900 nM, about 1000 nM to about 1800 nM, about 1000 nM to about 1700 nM, about 1000 nM to about 1600 nM, about 1000 nM to about 1500 nM, about 1000 nM to about 1400 nM, about 1000 nM to about 1300 nM, about 1000 nM to about 1200 nM, about 1000 nM to about 1100 nM, about 1100 nM to about 2000 nM, about 1100 nM to about 1900 nM, about 1100 nM to about 1800 nM, about 1100 nM to about 1700 nM, about 1100 nM to about 1600 nM, about 1100 nM to about 1500 nM, about 1100 nM to about 1400 nM, about 1100 nM to about 1300 nM, about 1100 nM to about 1200 nM, about 1200 nM to about 2000 nM, about 1200 nM to about 1900 nM, about 1200 nM to about 1800 nM, about 1200 nM to about 1700 nM, about 1200 nM to about 1600 nM, about 1200 nM to about 1500 nM, about 1200 nM to about 1400 nM, about 1200 nM to about 1300 nM, about 1300 nM to about 2000 nM, about 1300 nM to about 1900 nM, about 1300 nM to about 1800 nM, about 1300 nM to about 1700 nM, about 1300 nM to about 1600 nM, about 1300 nM to about 1500 nM, about 1300 nM to about 1400 nM, about 1400 nM to about 2000 nM, about 1400 nM to about 1900 nM, about 1400 nM to about 1800 nM, about 1400 nM to about 1700 nM, about 1400 nM to about 1600 nM, about 1400 nM to about 1500 nM, about 1500 nM to about 2000 nM, about 1500 nM to about 1900 nM, about 1500 nM to about 1800 nM, about 1500 nM to about 1700 nM, about 1500 nM to about 1600 nM, about 1600 nM to about 2000 nM, 1600 nM to about 1900 nM, about 1600 nM to about 1800 nM, about 1600 nM to about 1700 nM, about 1700 nM to about 2000 nM, about 1700 nM to about 1900 nM, about 1700 nM to about 1800 nM, about 1800 nM to about 2000 nM, about 1800 nM to about 1900 nM, or about 1900 nM to about 2000 nM) (e.g., as measured by SPR).

In some embodiments, preferred binding affinities to MADCAM-1 include those with a dissociation constant or $K_D$ of no greater than 1 µM, 2 µM, 3 µM, 4 µM, 5 µM, 6 µM, 7 µM, 8 µM, 9 µM, 10 µM, 15 µM, 20 µM, 25 µM, 30 µM, 40 µM, 50 µM, 60 µM, 70 µM, 80 µM, 90 µM, 100 µM, 110 µM, 120 µM, 130 µM, 140 µM, 150 µM, 200 µM, 250 µM, 300 µM, 400 µM, 500 µM, 600 µM, 700 µM, 800 µM, 900 µM, or 1000 µM.

In some embodiments, an anti-MADCAM-1 antibody or antigen-binding domain or antigen-binding fragment thereof exhibits a binding affinity ($K_D$) to MADCAM-1 that is between about 1 TM to about 100 TM (e.g., about 1 µM to about 90 µM, about 1 µM to about 80 µM, about 1 µM to about 70 µM, about 1 µM to about 60 µM, about 1 µM to about 50 µM, about 1 µM to about 40 µM, about 1 µM to about 30 µM, about 1 µM to about 20 µM, about 1 µM to about 10 µM, about 10 µM to about 100 µM, about 10 µM to about 90 µM, about 10 µM to about 80 µM, about 10 µM to about 70 µM, about 10 µM to about 60 µM, about 10 µM to about 50 µM, about 10 µM to about 40 µM, about 10 µM to about 30 µM, about 10 µM to about 20 µM, about 20 µM to about 100 µM, about 20 µM to about 90 µM, about 20 µM to about 80 µM, about 20 µM to about 70 µM, about 20 µM to about 60 µM, about 20 µM to about 50 µM, about 20 µM to about 40 µM, about 20 µM to about 30 µM, about 30 µM to about 100 µM, about 30 µM to about 90 µM, about 30 µM to about 80 µM, about 30 µM to about 70 µM, about 30 µM to about 60 µM, about 30 µM to about 50 µM, about 30 µM to about 40 µM, about 40 µM to about 100 µM, about 40 µM to about 90 µM, about 40 µM to about 80 µM, about 40 µM to about 70 µM, about 40 µM to about 60 µM, about 40 µM to about 50 µM, about 50 µM to about 100 µM, about 50 µM to about 90 µM, about 50 µM to about 80 µM, about 50 µM to about 70 µM, about 50 µM to about 60 µM, about 60 µM to about 100 µM, about 60 µM to about 90 µM, about 60 µM to about 80 µM, about 60 µM to about 70 µM, about 70 µM to about 100 µM, about 70 µM to about 90 µM, about 70 µM to about 80 µM, about 80 µM to about 100 µM, about 80 µM to about 90 µM, or about 90 µM to about 100 µM (e.g., as measured by SPR).

Receptor Polypeptides

This document provides methods and materials for introducing into a T-cell (e.g., CD4+ T-cell, $CD4^+CD45RA^+$ T-cell, $CD4^+$ $CD62L^+$ T-cell, or central memory T-cell) a nucleic acid sequence encoding a receptor or a "homing receptor" polypeptide (e.g., any of the exemplary receptor polypeptides described herein). In some embodiments, upon administering a T-cell that includes a receptor polypeptide to a subject, the receptor polypeptide increases the ability of the T-cell to home to a particular location or tissue in the subject as compared to a T-cell that does not include the receptor polypeptide (i.e., a T-cell where the receptor polypeptide was not introduced into the cell). For example, a receptor polypeptide can direct a $CD4^+/CD45RA^+$ T-cell to a particular tissue or area within a human where cells responsible for causing symptoms of an autoimmune disease are located. In some embodiments, the receptor polypeptide can be a chemokine receptor polypeptide, and a cell expressing the chemokine receptor can be chemotactically directed to a particular location (e.g., lymphoid tissue) within a mammal (e.g., a human).

In some embodiments, the T-cell that includes the receptor polypeptide has increased (e.g., at least a 5% increase, at least a 10% increase, at least a 20% increase, at least a 30% increase, at least a 40% increase, at least a 50% increase, at least a 60% increase, at least a 70% increase, at least a 80% increase, at least a 90% increase, at least a 100% increase, at least a 120% increase, at least a 140% increase, at least a 160% increase, at least a 180% increase, or at least a 200% increase) homing to a particular location or tissue in the subject as compared to a T-cell that does not include the receptor polypeptide.

Examples of chemokine receptors that can be transduced into a cell along with a FOXP3 polypeptide (e.g., any of the exemplary FOXP3 polypeptides described herein) include, without limitation, CCR6, CCR9, and GPR15. In some embodiments, a ligand for a chemokine receptor polypeptide can be present on the surface of a cell residing in a lymphoid organ (e.g., spleen, lymph nodes, bone marrow, and/or tonsils). In some embodiments, a ligand for a chemokine receptor polypeptide can be present on the surface of a cell residing in an inflamed peripheral tissue (e.g., lung) in a mammal (e.g., a human). For example, a T-cell (e.g., a $CD4^+$ T-cell, a $CD4^+CD45RA^+$ T-cell, a $CD4^+$ $CD62L^+$ T-cell, or central memory T-cell) transduced with a FOXP3 polypeptide (e.g., any of the exemplary FOXP3 polypeptides described herein) and a CXCR4 chemokine receptor polypeptide can be chemotactically directed to a CXCL12 ligand associated with inflammation in the bone marrow of a mammal. In another example, a T-cell (e.g., a $CD4^+$ T-cell, a $CD4^+CD45RA^+$ T-cell, a $CD4^+$ $CD62L^+$ T-cell, or central memory T-cell) transduced with a FOXP3 polypeptide (e.g., any of the exemplary FOXP3 polypeptides described herein) and a CCR6 chemokine receptor polypeptide can be directed to a particular tissue or area within a mammal where a CCL20 polypeptide is located (e.g., a ligand for the CCR6 chemokine receptor polypeptide). A CCL20 polypeptide can be associated with chronic inflammatory conditions (e.g., inflammatory bowel disease). In yet another example, a T-cell (e.g., a $CD4^+$ T-cell, a $CD4^+CD45RA^+$ T-cell, a $CD4^+$ $CD62L^+$ T-cell, or central memory T-cell) transduced with a FOXP3 polypeptide (e.g., any of the exemplary FOXP3 polypeptides described herein) and a CCR7 chemokine receptor polypeptide can be directed to a particular tissue or area within a mammal where a CCL19 and/or a CCL21 polypeptide are located, as CCL19 and CCL21 are ligands for the CCR7 chemokine receptor polypeptide. CCL19 and CCL20 polypeptides can be associated with chronic inflammatory conditions in the thymus and lymph nodes.

In some embodiments, a receptor polypeptide includes, without limitation, CCR6 polypeptide or a functional fragment thereof, a CCR9 polypeptide or a functional fragment thereof, and a GPR15 polypeptide or a functional fragment thereof.

As used herein, CCR6 refers to C—C motif chemokine receptor 6 polypeptide. When preparing the T-cell or treating a mammal with the T-cell, CCR6 refers to human CCR6. Non-limiting examples of a human CCR6 polypeptide include, without limitation, NCBI reference sequence: NP_004358.2 or a functional fragment thereof or NCBI reference sequence: NP_113597.2 or a functional fragment thereof.

As used herein, CCR9 refers to C—C motif chemokine receptor 9 polypeptide. When preparing the T-cell or treating a mammal with the T-cell, CCR9 refers to human CCR9. Non-limiting examples of a human CCR9 polypeptide include, without limitation, NCBI reference sequence: NP_001243298.1 or a functional fragment thereof; NCBI reference sequence: NP_001373376.1 or a functional fragment thereof; NCBI reference sequence: NP_001373377.1 or a functional fragment thereof; NCBI reference sequence: NP_006632.2 or a functional fragment thereof; or NCBI reference sequence: NP_112477.1 or a functional fragment thereof.

As used herein, GPR15 refers to G protein-coupled receptor 15 polypeptide. When preparing the T-cell or treating a mammal with the T-cell, GPR15 refers to human GPR15. An example of a human GPR15 polypeptide includes, without limitation, NCBI reference sequence: NP_005281.1 or a functional fragment thereof.

In some embodiments, the receptor polypeptide can be a GPR15 receptor polypeptide (e.g., a G protein-coupled receptor 15). For example, a cell (e.g., a CD4$^+$ T-cells, a CD4$^+$CD45RA$^+$ T-cell, a CD4$^+$ CD62L$^+$ T-cell, or central memory T-cell) transduced with a FOXP3 polypeptide (e.g., any of the exemplary FOXP3 polypeptides described herein) and a GPR15 receptor polypeptide can be directed to a particular tissues or area within a mammal where a GPR15L polypeptide is located (e.g., the colon).

Therapeutic Gene Products

This document provides methods and materials for introducing into a T-cell (e.g., CD4+ T-cell, CD4$^+$CD45RA$^+$ T-cell, CD4$^+$ CD62L$^+$ T-cell, or central memory T-cell) a nucleic acid sequence encoding a therapeutic gene product (e.g., a nucleic acid sequence encoding a therapeutic gene product). Any appropriate therapeutic gene product that enhances the immunosuppressive effects of a T-cell (e.g., a CD4$^+$ T-cell, a CD4$^+$CD45RA$^+$ T-cell, a CD4+CD62L$^+$ T-cell, or central memory T-cell) can be used.

Tissue Targeting

Also described herein are T-cells that include a first nucleic acid sequence encoding a FOXP3 polypeptide and a second nucleic acid sequence encoding a binding agent (e.g., any of the exemplary binding agents described herein), and optionally, a nucleic acid encoding a receptor polypeptide (e.g., any of the exemplary receptor polypeptides described herein), where the T-cell homes to a specific location or specific tissue when administered to a subject. As used herein, the term "homing" refers the ability of a T-cell to locate and enter an environmental niche (e.g., a particular location, organ, or tissue). The migration can result from, without limitation, receptor-ligand interactions, cytokine release, tissue damage, inflammatory signals, or other chemotactic signals. The terms "home," "homes" or "homed" can be used interchangeably with "homing."

In some embodiments, a T-cell that includes a combination of binding agent (e.g., any of the exemplary binding agents described herein) and optionally, a further a receptor polypeptide (e.g., any of the exemplary receptor polypeptides described herein) that determines, at least in part, the specific location in the body of the subject to which the T-cell is homed after being administered to the subject. Non-limiting examples of combinations of receptor polypeptides and binding agents are listed in Table 1. Table 1 also lists non-limiting "homing" locations for the various combinations of receptor polypeptides and binding agents.

TABLE 1

Combinations of receptor polypeptides, binding agents, and homing locations.

| Receptor polypeptide | Binding agent (scFv) | Homing location |
|---|---|---|
| CCR6 | MADCAM-1 | Intestine |
| CCR9 | MADCAM-1 | Intestine |
| GPR15 | MADCAM-1 | Colon |

In some embodiments, a T-cell includes a first nucleic acid sequence encoding a FOXP3 polypeptide, a second nucleic acid sequence encoding a CXCR6 polypeptide, and a third nucleic acid encoding an anti-MADCAM-1 scFv, where the T-cell homes to any inflammatory site or inflamed tissue when administered to a subject.

In some embodiments, a T-cell includes a first nucleic acid sequence encoding a FOXP3 polypeptide, a second nucleic acid sequence encoding a CCR6 polypeptide, and a third nucleic acid encoding an anti-MADCAM-1 scFv, where the T-cell homes to the intestine when administered to a subject.

In some embodiments, a T-cell includes a first nucleic acid sequence encoding a FOXP3 polypeptide, a second nucleic acid sequence encoding a CCR9 polypeptide, and a third nucleic acid encoding an anti-MADCAM-1 scFv, where the T-cell homes to the intestine when administered to a subject.

In some embodiments, a T-cell includes a first nucleic acid sequence encoding a FOXP3 polypeptide, a second nucleic acid sequence encoding a GPR15 polypeptide, and a third nucleic acid encoding an anti-MADCAM-1 scFv, where the T-cell homes to the colon when administered to a subject.

In some embodiments, a T-cell includes a first nucleic acid sequence encoding a FOXP3 polypeptide, a second nucleic acid sequence encoding a CXCR5 polypeptide, and a third nucleic acid encoding an anti-MADCAM-1 scFv, where the T-cell homes to the germinal center when administered to a subject.

In some embodiments, a T-cell that includes a FOXP3 polypeptide and a receptor polypeptide (e.g., any of the exemplary receptor polypeptides described herein), where the receptor polypeptide determines, at least in part, the specific location in the body of the subject to which the T-cell is homed after being administered to the subject. In some embodiments, a T-cell that includes a FOXP3 polypeptide and a binding agent (e.g., any of the exemplary binding agents described herein), where the binding agent determines, at least in part, the specific location in the body of the subject to which the T-cell is homed after being administered to the subject.

Methods of Producing T-Cells

As described herein, any appropriate method of producing cells (e.g., T-cells) comprising a FOXP3 polypeptide and a binding agent can be used to generate the T-cells as described herein. In some embodiments, a cell (e.g., a T-cell) that is transduced with the nucleic acid sequences described herein is isolated from a mammal (e.g., a human) using any appropriate method (e.g., magnetic activated sorting or flow cytometry-mediated sorting). In some cases, nucleic acid sequences encoding a FOXP3 polypeptide and a binding agent can be transformed into a cell (e.g., a T-cell) along with nucleic acid sequences encoding a receptor polypeptide and/or a therapeutic gene product. For example, a T-cell can be made by transducing nucleic acid sequences encoding a FOXP3 polypeptide and a binding agent into a cell (e.g., a T-cell) using a lentivirus.

In another example, a T-cell can be made by transducing nucleic acid sequences encoding a FOXP3 polypeptide, a binding agent, and a receptor polypeptide into a cell (e.g., a T-cell) using a lentivirus. In yet another example, a T-cell can be made by co-transducing nucleic acid sequences encoding a FOXP3 polypeptide, a binding agent, a receptor polypeptide, and a therapeutic gene product into a cell (e.g., a T-cell) using a lentivirus. In all cases described herein, the nucleic acid sequences are operably linked to a promoter or are operably linked to other nucleic acid sequences using a self-cleaving 2A polypeptide or IRES sequence.

Methods of introducing nucleic acids and expression vectors into a cell (e.g., an eukaryotic cell) are known in the art. Non-limiting examples of methods that can be used to introduce a nucleic acid into a cell include lipofection, transfection, electroporation, microinjection, calcium phosphate transfection, dendrimer-based transfection, cationic polymer transfection, cell squeezing, sonoporation, optical transfection, impalefection, hydrodynamic delivery, magnetofection, viral transduction (e.g., adenoviral and lentiviral transduction), and nanoparticle transfection. As used herein, "transformed" and "transduced" are used interchangeably.

In some embodiments, the transformed cell can be an immune cell, an epithelial cell, an endothelial cell, or a stem cell. In some examples, an immune cell is a T-cell, and the detection of memory T-cells can include, e.g., the detection of the level of expression of one or more of CD45RO, CCR7, L-selectin (CD62L), CD44, CD45RA, integrin αeϑ7, CD43, CD4, CD8, CD27, CD28, IL-7Rα, CD95, IL-2124, and LFA-1. Additional examples of T-cells that can be transduced are described herein.

Nucleic Acids/Vectors

Also provided herein are nucleic acids sequences that encode any of the polypeptides described herein. For example, nucleic acid sequences are included that encode for a FOXP3 polypeptide, a binding agent, a receptor polypeptide, and a therapeutic gene product. Also provided herein are vectors that include any of the nucleic acids encoding any of the polypeptides described herein (e.g., the polypeptides include, without limitation, a FOXP3 polypeptide, a binding agent, a receptor polypeptide, and a therapeutic gene product). Also provided herein is a set of vectors that include any of the nucleic acid sequences encoding any of the polypeptides described herein. For example, the set of vectors includes two vectors, three vectors, or four vectors where each vector includes one or more nucleic acids encoding any of the polypeptides described herein.

In some embodiments, the vector includes: a first nucleic acid sequence encoding a FOXP3 polypeptide; and a second nucleic acid sequence encoding a binding agent. In some embodiments, the vector includes: a first nucleic acid sequence encoding a FOXP3 polypeptide, a second nucleic acid sequence encoding a binding agent, and a nucleic acid sequence encoding a receptor polypeptide, where each nucleic acid sequence is operably linked to a promoter or operably linked to one of the other nucleic acid sequences in the vector.

In some embodiments, the vector includes: a first nucleic acid sequence encoding a FOXP3 polypeptide, a second nucleic acid sequence encoding a binding agent, a nucleic acid sequence encoding a receptor polypeptide, and a nucleic acid encoding a therapeutic gene product, where each nucleic acid sequence is operably linked to a promoter or operably linked to one of the other nucleic acid sequences in the vector.

Any of the vectors described herein can be an expression vector. For example, an expression vector can include a promoter sequence operably linked to the sequence encoding any of the polypeptides as described herein. Non-limiting examples of vectors include plasmids, transposons, cosmids, and viral vectors (e.g., any adenoviral vectors (e.g., pSV or pCMV vectors), adeno-associated virus (AAV) vectors, lentivirus vectors, and retroviral vectors), and any Gateway® vectors. In some cases, a vector can include sufficient cis-acting elements that supplement expression where the remaining elements needed for expression can be supplied by the host mammalian cell or in an in vitro expression system. Skilled practitioners will be capable of selecting suitable vectors and mammalian cells for making any of the T-cells as described herein. Any appropriate promoter (e.g., EF1 alpha) can be operably linked to any of the nucleic acid sequences described herein. Non-limiting examples of promoters to be used in any of the vectors or constructs described herein include EF1a, SFFV, PGK, CMV, CAG, UbC, MSCV, MND, EF1a hybrid, and/or CAG hybrid. As used herein, the term "operably linked" is well known in the art and refers to genetic components that are combined such that they carry out their normal functions. For example, a nucleic acid sequence is operably linked to a promoter when its transcription is under the control of the promoter. In another example, a nucleic acid sequence can be operably linked to other nucleic acid sequence by a self-cleaving 2A polypeptide or an internal ribosome entry site (IRES). In such cases, the self-cleaving 2A polypeptide allows the second nucleic acid sequence to be under the control of the promoter operably linked to the first nucleic acid sequence. The nucleic acid sequences described herein can be operably linked to a promoter. In some cases, the nucleic acid sequences described herein can be operably linked to any other nucleic acid sequence described herein using a self-cleaving 2A polypeptide or IRES. In some cases, the nucleic acid sequences are all included on one vector and operably linked either to a promoter upstream of the nucleic acid sequences or operably linked to the other nucleic acid sequences through a self-cleaving 2A polypeptide or an IRES.

Polypeptides

Also provided are polypeptides that include an antigen-binding domain comprising: an amino acid sequence at least 80% identical (e.g., at least 85% identical, at least 90% identical, at least 95% identical, at least 99% identical, or 100% identical) to a sequence selected from the group of SEQ ID NOs: 6-29. In some embodiments, the polypeptide includes an antigen-binding domain that includes a heavy chain variable domain including an amino acid sequence at least 80% (e.g., at least 85%, at least 90%, at least 95%, at least 99%, or 100%) identical to SEQ ID NOs: 30, 32, 34, 36, 38, 40, 42, 44, 46, 48, 50, 52, 54, 56, 58, 60, 62, 64, 66, 68, 70, 72, 74, or 76. In some embodiments, the polypeptide includes an antigen-binding domain that includes a light chain variable domain including an amino acid sequence at least 80% (e.g., at least 85%, at least 90%, at least 95%, at least 99%, or 100%) identical to SEQ ID NOs: 31, 33, 35, 37, 39, 41, 43, 45, 47, 49, 51, 53, 55, 57, 59, 61, 63, 65, 67, 69, 71, 73, 75, or 77.

Also provided are polypeptides that include an antigen-binding domain comprising: (i) the three heavy chain CDR sequences present in SEQ ID NO: 30 and the three light chain CDR sequences present in SEQ ID NO: 31; (ii) the three heavy chain CDR sequences present in SEQ ID NO: 32 and the three light chain CDR sequences present in SEQ ID NO: 33; (iii) the three heavy chain CDR sequences present in SEQ ID NO: 34 and the three light chain CDR sequences present in SEQ ID NO: 35; (iv) the three heavy chain CDR sequences present in SEQ ID NO: 36 and the three light chain CDR sequences present in SEQ ID NO: 37; (v) the three heavy chain CDR sequences present in SEQ ID NO: 38 and the three light chain CDR sequences present in SEQ ID NO: 39; (vi) the three heavy chain CDR sequences present in SEQ ID NO: 40 and the three light chain CDR sequences present in SEQ ID NO: 41; (vii) the three heavy chain CDR sequences present in SEQ ID NO: 42 and the three light chain CDR sequences present in SEQ ID NO: 43; (viii) the three heavy chain CDR sequences present in SEQ ID NO: 44 and the three light chain CDR sequences present in SEQ ID NO: 45; (ix) the three heavy chain CDR sequences present in SEQ ID NO: 46 and the three light chain CDR sequences present in SEQ ID NO: 47; (x) the three heavy chain CDR sequences present in SEQ ID NO: 48 and the three light chain CDR sequences present in SEQ ID NO: 49; (xi) the three heavy chain CDR sequences present in SEQ ID NO: 50 and the three light chain CDR sequences present in SEQ ID NO: 51; (xii) the three heavy chain CDR sequences present in SEQ ID NO: 52 and the three light chain CDR sequences present in SEQ ID NO: 53; (xiii) the three heavy chain CDR sequences present in SEQ ID NO: 54 and the three light chain CDR sequences present in SEQ ID NO: 55; (xiv) the three heavy chain CDR sequences present in SEQ ID NO: 56 and the three light chain CDR sequences present in SEQ ID NO: 57; (xv) the three heavy chain CDR sequences present in SEQ ID NO: 58 and the three light chain CDR sequences present in SEQ ID NO: 59; (xvi) the three heavy chain CDR sequences present in SEQ ID NO: 60 and the three light chain CDR sequences present in SEQ ID NO: 61; (xvii) the three heavy chain CDR sequences present in SEQ ID NO: 62 and the three light chain CDR sequences present in SEQ ID NO: 63; (xviii) the three heavy chain CDR sequences present in SEQ ID NO: 64 and the three light chain CDR sequences present in SEQ ID NO: 65; (xix) the three heavy chain CDR sequences present in SEQ ID NO: 66 and the three light chain CDR sequences present in SEQ ID NO: 67; (xx) the three heavy chain CDR sequences present in SEQ ID NO: 68 and the three light chain CDR sequences present in SEQ ID NO: 69; (xxi) the three heavy chain CDR sequences present in SEQ ID NO: 70 and the three light chain CDR sequences present in SEQ ID NO: 71; (xxii) the three heavy chain CDR sequences present in SEQ ID NO: 72 and the three light chain CDR sequences present in SEQ ID NO: 73; (xxiii) the three heavy chain CDR sequences present in SEQ ID NO: 74 and the three light chain CDR sequences present in SEQ ID NO: 75; or (xxiv) the three heavy chain CDR sequences present in SEQ ID NO: 76 and the three light chain CDR sequences present in SEQ ID NO: 77.

In some embodiments, a polypeptide described herein can be an antibody (e.g., a human or humanized antibody). In some embodiments, the antibody can be a human or humanized IgG1, IgG2, IgG3, or IgG4 antibody. In some embodiments, a polypeptide described herein can be an antigen-binding antibody fragment (e.g., an scFv).

Compositions and Kits

Also provided herein are compositions (e.g., pharmaceutical compositions) that include any of the T-cells described herein, a population of any of the T-cells described herein, any of the antibodies or antigen-binding fragments described herein, or any of the nucleic acids or vectors described herein. In some embodiments, the compositions include any of the T-cells (e.g., any of the T-cells described herein, including any of the T-cells produced using any of the methods described herein). In some embodiments, the compositions are pharmaceutical compositions (e.g., pharmaceutical compositions formulated for different routes of administration (e.g., intravenous or subcutaneous)). In some embodiments, the pharmaceutical compositions can include a pharmaceutically acceptable carrier (e.g., phosphate buffered saline).

Also provided herein are compositions that include a binding agent comprising an antigen-binding domain or antigen-binding fragment comprising an amino acid sequence at least 80% (e.g., at least 85%, 90%, 95%, 99% and 100%) identical to a sequence selected from SEQ ID NOs: 6-29.

Also provided are kits that include any of the compositions (e.g., pharmaceutical compositions) described herein that include any of the nucleic acids, any of the T-cells, or any of the vectors described herein. In some embodiments, a kit can include a solid composition (e.g., a lyophilized composition including any of the vectors or nucleic acids described herein) and a liquid for solubilizing the lyophilized composition.

Cells

Also provided herein are cells (e.g., any of the exemplary cells described herein or known in the art) comprising one or more of any of the nucleic acids described herein (e.g., a first nucleic acid encoding a FOXP3 polypeptide, a second nucleic acid encoding a binding agent, and optionally, one or both of a nucleic acid encoding a receptor polypeptide and a nucleic acid that encodes a therapeutic gene product). Also provided herein are cells (e.g., any of the exemplary cells described herein or known in the art) that include one or more of any of the vectors described herein. In some embodiments, the cells are any of the exemplary types of T-cells described herein or known in the art. In some embodiments, a T-cell includes, without limitation, a CD4$^+$ T-cell, a CD4$^+$CD45RA$^+$ T-cell, a CD4$^+$ CD62L$^+$ T-cell, or a central memory T-cell).

In some embodiments of any of the methods described herein, the cell can be a eukaryotic cell. As used herein, the term "eukaryotic cell" refers to a cell having a distinct, membrane-bound nucleus. Such cells may include, for example, mammalian (e.g., rodent, non-human primate, or human) cells. Non-limiting examples of mammalian cells include Chinese hamster ovary cells and human embryonic kidney cells (e.g., HEK293 cells).

Methods of Treatment

Also provided herein are methods of treating a mammal (e.g., a human) having an autoimmune disease that includes administering to the mammal (e.g., human) a therapeutically effective amount of a cell (e.g., any of the exemplary T-cells described herein) or any of the compositions (e.g., pharmaceutical compositions) described herein.

In some embodiments, these methods can result in a reduction in the number, severity, or frequency of one or more symptoms of the autoimmune diseases in the mammal (e.g., as compared to the number, severity, or frequency of the one or more symptoms of the autoimmune disease in the mammal prior to treatment). For example, a mammal having an autoimmune disease having been administered a T-cell as described here can experience a reduction in inflammation or autoantibody production.

Also provided herein are methods of treating a mammal (e.g., a human) having an autoimmune disease that includes administering to the mammal (e.g., a human) a therapeutically effective amount of a T-cell that includes a first nucleic acid sequence encoding a FOXP3 polypeptide, a second nucleic acid sequence encoding a CXCR3 polypeptide, and a third nucleic acid encoding an anti-MADCAM-1 scFv, where the T-cell homes to any inflammatory site or inflamed tissue when administered to the mammal (e.g., a human).

Also provided herein are methods of treating a mammal (e.g., a human) having an autoimmune disease that includes administering to the mammal (e.g., a human) a therapeutically effective amount of a T-cell that includes a first nucleic acid sequence encoding a FOXP3 polypeptide, a second nucleic acid sequence encoding a CCR6 polypeptide, and a third nucleic acid encoding an anti-MADCAM-1 scFv, where the T-cell homes to the intestine when administered to the mammal (e.g., a human).

Also provided herein are methods of treating a mammal (e.g., a human) having an autoimmune disease that includes administering to the mammal (e.g., a human) a therapeutically effective amount of a T-cell that includes a first nucleic acid sequence encoding a FOXP3 polypeptide, a second nucleic acid sequence encoding a CCR9 polypeptide, and a third nucleic acid encoding an anti-MADCAM-1 scFv, where the T-cell homes to the intestine when administered to the mammal (e.g., a human).

Also provided herein are methods of treating a mammal (e.g., a human) having an autoimmune disease that includes administering to the mammal (e.g., a human) a therapeutically effective amount of a T-cell that includes a first nucleic acid sequence encoding a FOXP3 polypeptide, a second nucleic acid sequence encoding a GPR15 polypeptide, and a third nucleic acid encoding an anti-MADCAM-1 scFv, where the T-cell homes to the colon when administered to the mammal (e.g., a human).

Also provided herein are methods of treating a mammal (e.g., a human) having an autoimmune disease that includes administering to the mammal (e.g., a human) a therapeutically effective amount of a T-cell that includes a first nucleic acid sequence encoding a FOXP3 polypeptide, a second nucleic acid sequence encoding a CXCR5 polypeptide, and a third nucleic acid encoding an anti-MADCAM-1 scFv, where the T-cell homes to the germinal center when administered to the mammal (e.g., a human).

Any appropriate method of administration can be used to administer the T-cells to a mammal (e.g. a human) having an autoimmune disease. Examples of methods of administration include, without limitation, parenteral administration and intravenous injection.

A pharmaceutical composition containing the T-cells and a pharmaceutically acceptable carrier or buffer can be administered to a mammal (e.g., a human) having an autoimmune disease. For example, a pharmaceutical composition (e.g., a T-cell along with a pharmaceutically acceptable carrier) to be administered to a mammal having an autoimmune disease can be formulated in an injectable form (e.g., emulsion, solution and/or suspension). In some embodiments, a pharmaceutical composition containing the T-cells can include phosphate buffered saline.

Pharmaceutically acceptable carriers, fillers, and vehicles that can be used in a pharmaceutical composition described herein can include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

Effective dosage can vary depending on the severity of the autoimmune disease, the route of administration, the age and general health condition of the subject, excipient usage, the possibility of co-usage with other therapeutic treatments, and the judgment of the treating physician. An effective amount of a T-cell can be any amount that reduces inflammation and autoantibody production within a mammal having an autoimmune disease without producing significant toxicity to the mammal. For example, an effective amount of T-cells administered to a mammal having an autoimmune disease can be from about $1 \times 10^6$ cells to about $1 \times 10^{10}$ (e.g., from about $1 \times 10^6$ to about $1 \times 10^9$, from about $1 \times 10^6$ to about $1 \times 10^8$, from about $1 \times 10^6$ to about $1 \times 10^7$, from about $1 \times 10^7$ to about $1 \times 10^{10}$, from about $1 \times 10^7$ to about $1 \times 10^9$, from about $1 \times 10^7$ to about $1 \times 10^8$, from about $1 \times 10^8$ to about $1 \times 10^{10}$, from about $1 \times 10^8$ to about $1 \times 10^9$, or form about $1 \times 10^9$ to about $1 \times 10^{10}$ cells. In some cases, the T-cells can be a purified population of immune cells generated as described herein. In some cases, the purity of the population of T-cells can be assessed using any appropriate method, including, without limitation, flow cytometry. In some cases, the population of T-cells to be administered can include a range of purities from about 70% to about 100%, from about 70% to about 90%, from about 70% to about 80%, from about 80% to about 90%, from about 90% to about 100%, from about 80% to about 100%, from about 80% to about 90%, or from about 90% to about 100%. In some cases, the dosage (e.g., number of T-cells to be administered) can adjusted based on the level of purity of the T-cells.

The frequency of administration of a T-cell can be any frequency that reduces inflammation or autoantibody production within a mammal having an autoimmune disease without producing toxicity to the mammal. In some cases, the actual frequency of administration can vary depending on various factors including, without limitation, the effective amount, duration of treatment, use of multiple treatment agents, route of administration, and severity of the condition may require an increase or decrease in frequency of administration.

An effective duration for administering a composition containing a T-cell can be any duration that reduces inflammation or autoantibody production within a mammal having an autoimmune disease without producing toxicity to the mammal. In some cases, the effective duration can vary from several days to several months. In general, the effective treatment duration for administering a composition containing a T-cell to treat an autoimmune disease can range in duration from about one month to about five years (e.g., from about two months to about five years, from about three months to about five years, from about six months to about five years, from about eight months to about five years, from about one year to about five years, from about one month to about four years, from about one month to about three years, from about one month to about two years, from about six months to about four years, from about six months to about three years, or from about six months to about two years). In some cases, the effective treatment duration for administering a composition containing a T-cell can be for the remainder of the life of the mammal.

In some cases, a course of treatment and/or the severity of one or more symptoms related to autoimmune disease can be monitored. Any appropriate method can be used to determine whether the autoimmune disease is being treated. For example, immunological techniques (e.g., ELISA) can be performed to determine if the level of autoantibodies present within a mammal being treated as described herein is reduced following the administration of the T-cells. Remission and relapse of the disease can be monitored by testing for one or more markers of autoimmune disease.

Any appropriate autoimmune disease can be treated with a T-cell as described herein. In some cases, an autoimmune disease caused by the accumulation of autoantibodies can be treated with a T-cell as described herein. Examples of autoimmune diseases include, without limitation, lupus, rheumatoid arthritis, multiple sclerosis, insulin dependent diabetes mellitis, myasthenia gravis, Grave's disease, autoimmune hemolytic anemia, autoimmune thrombocytopenia purpura, Goodpasture's syndrome, pemphigus vulgaris, acute rheumatic fever, post-streptococcal glomerulonephritis, Crohn's disease, Celiac disease, and polyarteritis nodosa.

The invention will be further described in the following examples, which do not limit the scope of the invention described in the claims.

EXAMPLES

Example 1. Enforced Expression of FOXP3 in CD4+ T-Cells

A nucleic acid sequence encoding a FOXP3 polypeptide is transformed into CD4+/CD45RA+ T-cells to generate enforced expression of FOXP3 (eFOXP3) (FIG. 1). The nucleotide sequence encoding the FOXP3 polypeptide (e.g., a wild-type FOXP3 polypeptide or a FOXP3 polypeptide and is operably linked to an SSFV promoter. The nucleic acid sequence encoding the FOXP3 polypeptide is transformed into primary CD4+/CD45RA+ T-cells along with a nucleic acid sequence encoding a chimeric antigen receptor polypeptide comprising an intracellular domain made up of a CD3zeta domain and a CD28 domain. Following transformation, the cells are expanded in the presence of rIL-2 and optionally purified, e.g., based on low expression of CD127 (IL7 receptor). Markers of the suppressive phenotype of the transduced cells (e.g., CD4+/CD45RA+ transformed with an exogenous FOXP3 polypeptide) is determined by expression of Treg-associated molecules (e.g., CD25, CTLA-4, and GITR) and/or a cytokine profile upon re-stimulation of the transduced cell (e.g., low production of IL-2, IFNgamma, and IL-17).

Example 2. Expression of Therapeutic Outputs

Figure 2:
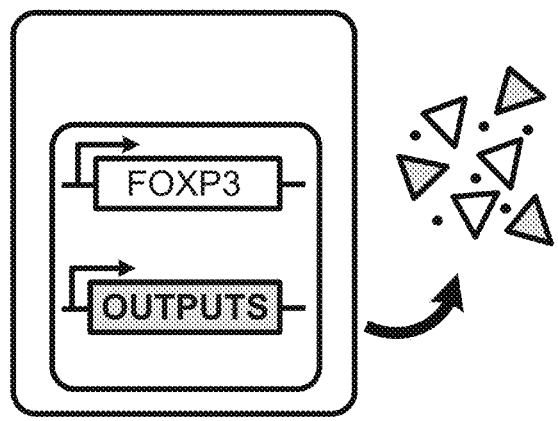
FIG. 2 is a diagram showing an exemplary T-cell with enforced expression of a FOXP3 polypeptide and a therapeutic gene product. Expression of a therapeutic gene product in addition to a FOXP3 polypeptide can result in enhancement of a core Treg program. Examples of suitable therapeutic gene products include, without limitation, IL6R scFv, IFNαR scFv, IL-10, IL-4, IL-13, and any anti-fibrotic protein.

CD4+/CD45RA+ T-cells are transduced with a lentivirus having nucleic acid sequences encoding a FOXP3 polypeptide having mutations as described herein, a receptor polypeptide, and a therapeutic gene product (FIG. 2). Here, a CD4+/CD45RA+ T-cell is transformed with a nucleic acid sequence encoding a FOXP3 polypeptide, a nucleic acid sequence encoding a CXCR3 chemokine receptor polypeptide, and is also transformed with a nucleic acid sequence encoding a scFv antigen-binding fragment that is capable of binding to an IL-6R antigen expressed on a cell associated with an autoimmune disease. The binding of the scFV to an epitope of IL-6R blocks the binding of IL-6R to IL-6. An antibody used in this example includes Tocilizumab, which is a humanized anti-IL-6R antibody. The variable light and heavy chain domains of Tocilizumab (See, U.S. Pat. No. 5,795,965) are provided to the cells using nucleic acid sequence encoding a scFv linked to a secretion signal and operably linked by a constitutive promoter such as EF-1α. Mutations are introduced into the amino acid sequence of Tocilizumab that render the heavy and light chains more favorable binding properties to the IL-6R (See, U.S. Pat. No. 8,562,991). Tregs are not known to naturally produce IL-6 blocking mediators (e.g., antibody or antigen-binding fragments to IL-6R). Therefore, expression of such blockers transformed into a CD4+/CD45RA+ T-cell along with an a nucleic acid sequence encoding a FOXP3 polypeptide will render the T-cells more effective in inflammatory environments than T-cells not transformed with the nucleic acid sequences described herein. The binding of the scFv to IL-6R+ is confirmed by flow cytometry. Secretion of the scFv is verified by ELISA, and the biological activity is confirmed by inhibition of IL-6 signaling in a reporter cell assay (e.g., IL-6 Luciferase stable reporter cell line from Novus Biologicals).

Figure 3:
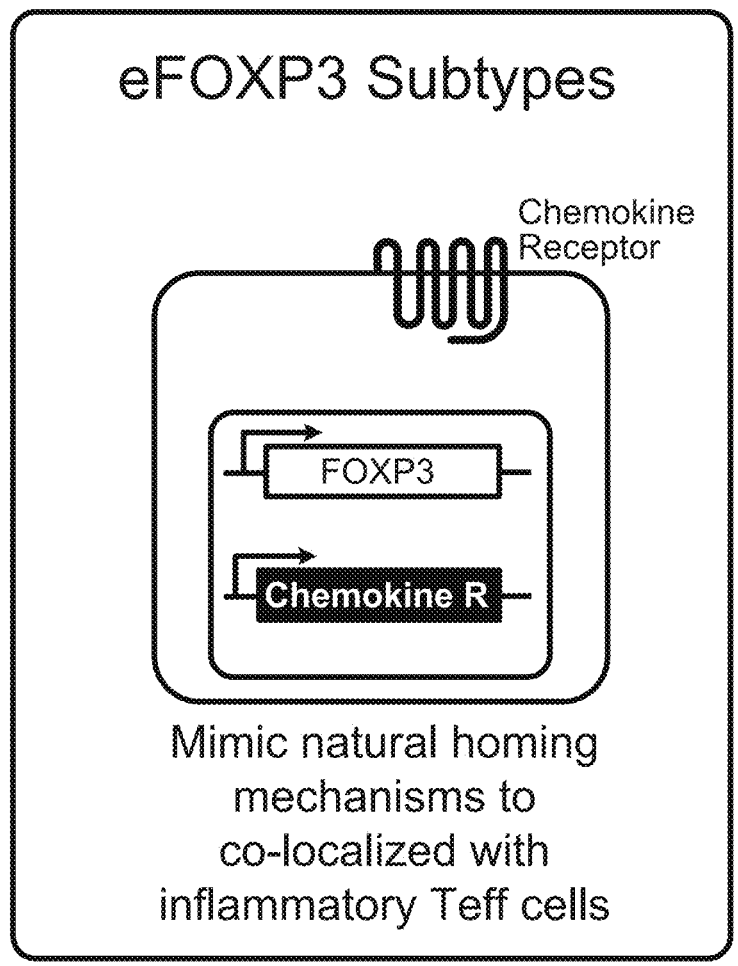
FIG. 3 is a diagram showing an exemplary T-cell with enforced expression of a FOXP3 polypeptide and a receptor polypeptide (e.g., a chemokine receptor polypeptide).

Example 3. Enforced Expression of Chemokine Receptors and Tissue Targeting of CD4+FOXP3+ T-Cells CD4+CD45RA+ T-cells are transduced with a lentivirus having nucleic acid sequences encoding a CXCR3 polypeptide and a nucleic acid sequence encoding a FOXP3 polypeptide (FIG. 3). Following transformation, the cells are expanded in the presence of high dose rIL-2 and purified based on low expression of CD127 (IL7 receptor). Other means of purifying the cells as described herein or known in the art can also be used to purify the T-cell. CXCR3 expression is confirmed by flow cytometric analysis using an antibody against the CXCR3 polypeptide (e.g., anti-human CD183 (CXCR3) Biolegend Cat. No. RU0353707). CXCR3 function is also confirmed by an in vitro chemotaxis assay (e.g., transwell migration assay). Briefly, transduced cells are placed in a transwell system with a CXCR3 ligand (e.g., 50-300 ng/mL CXCL10 (human rCXCL10 from R&D Systems Cat No. 266-IP-010)) or a control chemokine present on the side of the membrane opposite the transduced cells. Migration of cells across the membrane is evaluated by flow cytometry using an antibody against CXCR3. Specificity is further confirmed by blocking migration with anti-CXCR3 blocking antibody.

Example 4. Attachment with Cell Surface Binding Agent

Figure 4:
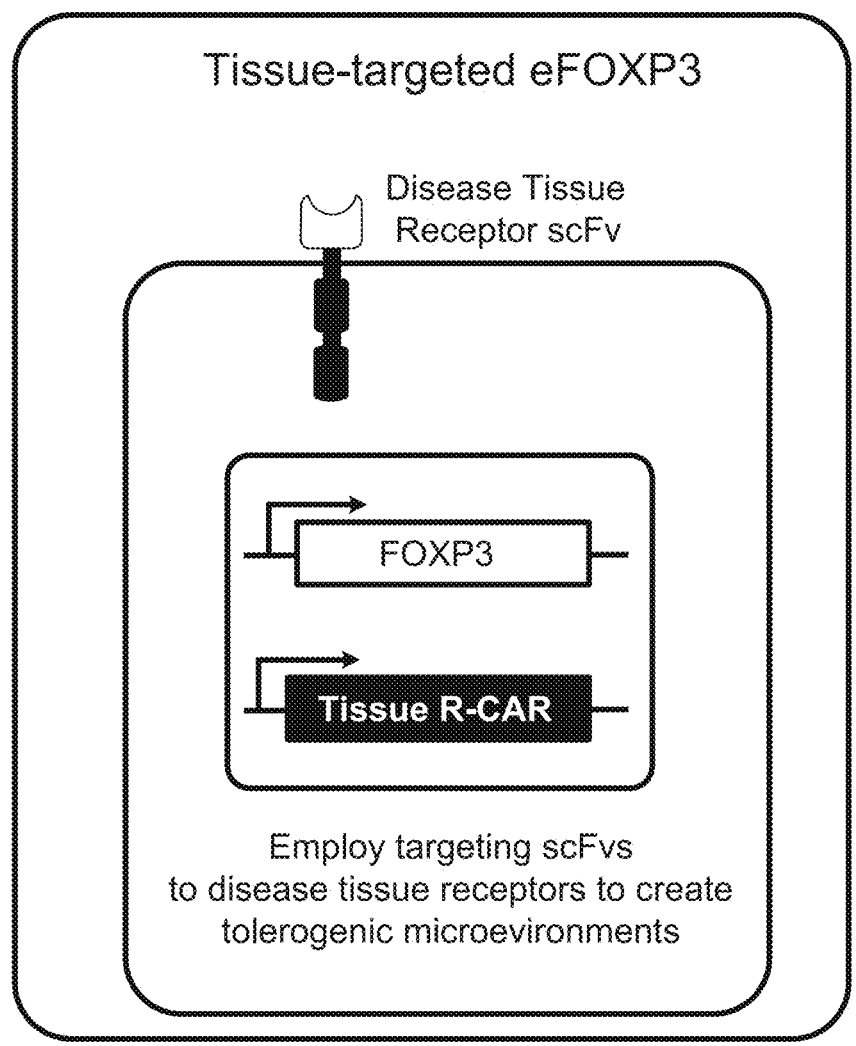
FIG. 4 is a diagram showing an exemplary T-cell with enforced expression of a FOXP3 polypeptide and a receptor polypeptide (e.g., a chimeric antigen receptor polypeptide).

CD4+/CD45RA+ T-cells are transduced with a lentivirus having nucleic acid sequences encoding a FOXP3 polypeptide and a chimeric antigen receptor polypeptide including an scFv capable of binding to an intercellular adhesion molecule-1 (MADCAM-1) (FIG. 4). MADCAM-1 is expressed on endothelial cells and is responsive to numerous inflammatory mediators (see, e.g., Xu et al., *Immunol. Cell Biol.* 85(8):633-639, 2008).

The chimeric antigen receptor includes an extracellular domain having a scFv domain directed to MADCAM-1, a transmembrane domain and an intracellular signaling domain. The affinity of the scFv is tuned to bind at high antigen density that exists in diseased tissues but avoid targeting healthy tissues with basal MADCAM-1 expression. The scFv is coupled to a transmembrane domain which spans the membrane and is derived from a CD8 transmembrane domain (e.g., CD8a stalk and CD8a hinge). The intracellular signaling domain is comprised of the CD3zeta domain and an additional co-stimulatory domain such as CD28, 4-1BB, ICOS, OX-40 and/or CD27 to transmit a proliferative/survival signal upon antigen recognition.

Figure 5:
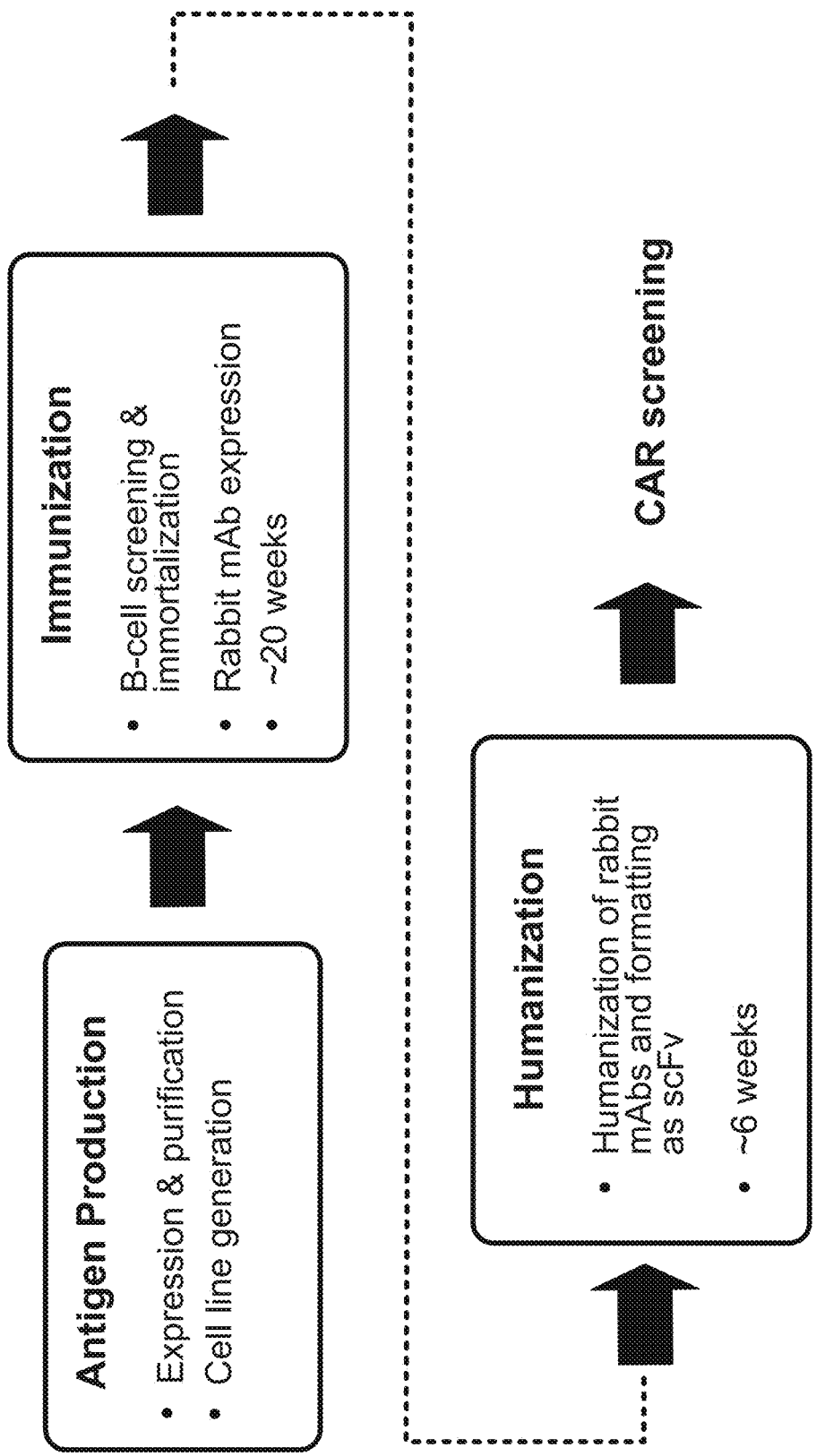
FIG. 5 is a schematic showing an exemplary workflow for identifying anti-MADCAM-1 scFvs.

Example 5. Antibody Generation—Humanization and Binding Affinity for MADCAM-1 scFv FIG. 5 shows the exemplary workflow used to identify candidate anti-MADCAM-1 scFVs. Humanized MADCAM-1 single-chain variable fragment (scFv) antibodies originated from rabbit immunoglobulin G antibodies with kappa light chains from K1 or K2 subclasses, and were generated by grafting of rabbit complementarity-determining region (CDR) onto human antibody framework regions.

Monoclonal antibodies were first generated by immunization of *O. cuniculus* with recombinantly expressed human MADCAM-1 extracellular domains. Clones were selected by antigen ELISA and binding to an antigen expressing cell line. CDRs for sequenced antibodies were defined as the union (Zhang et al., *MAbs* 9(3):419-429, 2017) of sequences identified by Kabat (Kabat et al., Sequences of Proteins of Immunological Interest, Diane Publishing Company, 1992) and IMGT (Lefranc et al., *Dev. Comp. Immunol.* 27:55-77, 2003) methods. Antibodies were humanized by CDR grafting onto human framework candidates identified by sequence similarity and critical framework amino acids back mutated as experimentally determined. Given the unique disulfide bonding patterns in rabbit IgG antibodies both in the framework and CDR regions; consideration was taken to ensure proper pairing of disulfide bonds. scFvs were subsequently generated by fusing humanized variable heavy (VH) and variable light (VL) regions in the VH-VL orientation with a standard $(G_4S)_3$ linker. Mutations (e.g., amino acid substitutions) were introduced into CDR regions to modulate (e.g., increase) KD.

Figure 6:
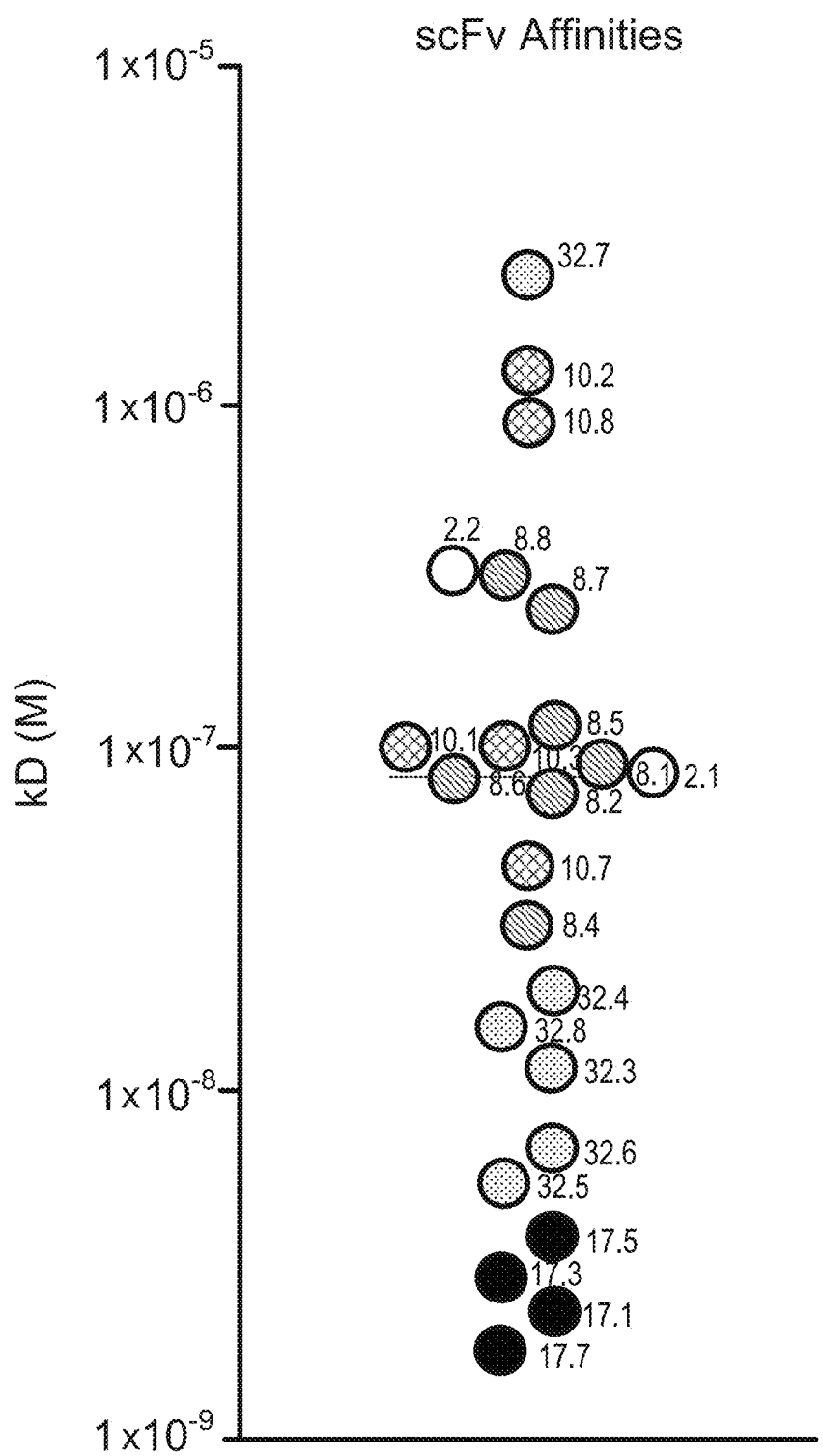
FIG. 6 is a plot showing the binding affinities ($K_D$)(M) for a set of anti-MADCAM-1 scFvs. Each circle represents a different anti-MADCAM-1 scFv.

Binding affinity (KD) of MADCAM-1 scFv antibodies from Table 2 was measured using biolayer interferometry (See also FIG. 6). Streptavidin biosensors were loaded for 5 seconds with 10 Tg/mL biotinylated-MADCAM-1 antigen followed by acquisition of the baseline signal in phosphate buffer saline supplemented with bovine serum albumin and sodium azide. For the association step loaded probes were incubated for 250 seconds with a titration of anti-MAD-CAM-1 scFv antibodies at concentrations generally between 0 nM and 2 TM. This was followed by a dissociation step in buffer lacking anti-MADCAM-1 scFv for 250 seconds. Experimental data was normalized to a reference probe and high-frequency noise was removed by Savitzky-Golay filtering. On and off-rate constants were determined using a globally fitted 1:1 binding model.

TABLE 2

$K_D$ for MADCAM-1 scFv Clones

| Clone | kon (1/Ms) | koff (1/s) | Kd (nm) |
|---|---|---|---|
| MAdCAM1 scFv 32.3 | 4.07E+05 | 4.91E-03 | 12.1 |
| MAdCAM1 scFv 32.4 | 5.77E+05 | 1.08E-02 | 18.7 |
| MAdCAM1 scFv 32.5 | 2.72E+05 | 1.46E-03 | 5.4 |
| MAdCAM1 scFv 32.6 | 3.27E+05 | 2.19E-03 | 6.7 |
| MAdCAM1 scFv 32.7 | 4.16E+05 | 9.91E-03 | 23.8 |
| MAdCAM1 scFv 32.8 | 5.34E+05 | 8.30E-03 | 15.5 |
| MAdCAM1 scFv 8.1 | 2.07E+04 | 1.86E-03 | 89.9 |
| MAdCAM1 scFv 8.2 | 3.78E+04 | 2.95E-03 | 78 |
| MAdCAM1 scFv 8.4 | 1.27E+04 | 3.93E-04 | 30.9 |
| MAdCAM1 scFv 8.5 | 1.38E+04 | 1.58E-03 | 114.5 |
| MAdCAM1 scFv 8.6 | 2.57E+04 | 2.18E-03 | 84.8 |
| MAdCAM1 scFv 8.7 | 1.66E+04 | 4.28E-03 | 257.8 |
| MAdCAM1 scFv 8.8 | 2.24E+04 | 6.96E-03 | 310.7 |
| MAdCAM1 scFv 17.1 | 2.47E+05 | 5.68E-04 | 2.3 |
| MAdCAM1 scFv 17.3 | 3.04E+05 | 8.68E-04 | 2.9 |
| MAdCAM1 scFv 17.5 | 2.58E+05 | 9.67E-04 | 3.7 |
| MAdCAM1 scFv 17.7 | 3.00E+05 | 5.37E-04 | 1.8 |
| MAdCAM1 scFv 2.1 | 7.08E+04 | 6.02E-03 | 85 |
| MAdCAM1 scFv 2.2 | 5.08E+04 | 1.67E-02 | 328.7 |
| MAdCAM1 scFv 10.1 | 1.22E+04 | 1.25E-03 | 102.5 |
| MAdCAM1 scFv 10.2 | 5.13E+03 | 6.46E-03 | 1259.3 |
| MAdCAM1 scFv 10.3 | 1.16E+04 | 1.14E-03 | 98.3 |
| MAdCAM1 scFv 10.7 | 2.38E+04 | 1.08E-03 | 45.4 |
| MAdCAM1 scFv 10.8 | 2.79E+03 | 2.59E-03 | 928.3 |

Example 6. Transmigration of T-Cells

Engineered T-cells as described in Example 4 (e.g., CD4+ T-cells having nucleic acid sequences encoding a FOXP3 polypeptide and a chimeric antigen receptor polypeptide including an scFv capable of binding to MADCAM-1) require selective binding to endothelial cells present in inflamed tissues which have high levels of MADCAM-1 expression. In order to enter the inflamed tissue and mediate their therapeutic effect, the engineered T-cells undergo transendothelial migration (TEM) or diapedesis. Here, T-cells including a FOXP3 polypeptide and a chimeric antigen receptor (CAR) having an anti-MADCAM-1 scFv extracellular domain were guided to locations within the subject (e.g., inflamed tissue, intestine, or colon) by the MADCAM-1 scFv. The engineered T-cell's ability to transmigrate once reaching the location in the subject depends on, but not limited to, binding affinity ($K_D$) of the scFv.

Engineered T-cells expressing a particular MADCAM-1-scFv-CAR can be screened for their ability to bind to endothelial cells using binding assays conducted under flow conditions similar to that of the hemodynamic shear stress of blood flow. An exemplary assay is described in Brown et al., *BMC Immunol.* 2:9, 2001, which is herein incorporated by reference in its entirety. Briefly, engineered T-cells are exposed to human endothelial cells under conditions of physiological shear stress, and the number of T-cells bound are measured under flow forces in the range of 0.5-8 dynes/cm$^2$. Optimally, the engineered T-cell will bind minimally to normal endothelial cells in their basal state and will bind to a greater extent to inflammatory cytokine-activated endothelial cells. Examples of inflammatory cytokines are IL-1, TNFα, and IFNγ. Endothelial cells treated with such cytokines dramatically upregulate MADCAM-1 and other cell adhesion molecules, thus mimicking the vasculature in inflamed tissues, as described in Dustin et al., *J. Cell Biol.* 107(1):321-331, 1988, which is herein incorporated by reference in its entirety.

To measure TEM, an in vitro two chamber migration assay was developed to screen engineered T-cells (e.g., CD4+ T-cells having nucleic acid sequences encoding a FOXP3 polypeptide and a chimeric antigen receptor polypeptide including an scFV capable of binding to MAD-CAM-1). Non-limiting examples of assays of measuring TEM are as described in Muller and Luscinskas, *Methods Enzymol.* 443:155-176, 2009, which is herein incorporated by reference in its entirety. Human umbilical endothelial cells, human microvascular endothelial cells, or intestinal endothelial cells were grown in an inner chamber as a monolayer on extracellular matrix (ECM) based hydrogels. The ECM support was pre-coated with fibronectin or human serum without growth factors to enhance plating efficiency. Established monolayers were then treated with TNFα to mimic the inflamed state and to increase the levels of MADCAM-1. TNFα was titrated to determine concentrations necessary to recapitulate MADCAM-1 expression in diseased tissues. Engineered T-cells (e.g., CD4+ T-cells having nucleic acid sequences encoding a FOXP3 polypeptide and a chimeric antigen receptor polypeptide including a scFv capable of binding to MADCAM-1) were then added to the inner chamber and actively monitored by live-cell fluorescence microscopy for activation and diapedesis. Through the course of monolayer establishment and transmigration assays, the outer chamber was supplemented with media in the presence or absence of chemoattractants, such as selected chemokines that are present in disease tissue and ligands of chemokine receptors expressed on the T-cells. Only engineered T-cells that included an scFv capable of binding MADCAM-1 with a particular binding affinity enable transmigration from the inner chamber to the outer chamber, as measured by fluorescence microscopy.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

Sequence Appendix

| SEQ ID NO: | Name | Sequence |
|---|---|---|
| SEQ ID NO: 1 | FOXP3 polypeptide | MPNPRPGKPSAPSLALGPSPGASPSWRAAPKASDLLGARGPGG TFQGRDLRGGAHASSSSLNPMPPSQLQLPTLPLVMVAPSGARL GPLPHLQALLQDRPHFMHQLSTVDAHARTPVLQVHPLESPAMI SLTPPTTATGVFSLKARPGLPPGINVASLEWVSREPALLCTFPNP SAPRKDSTLSAVPQSSYPLLANGVCKWPGCEKVFEEPEDFLKH CQADHLLDEKGRAQCLLQREMVQSLEQQLVLEKEKLSAMQAH LAGKMALTKASSVASSDKGSCCIVAAGSQGPVVPAWSGPREAP DSLFAVRRHLWGSHGNSTFPEFLHNMDYFKFHNMRPPFTYATL IRWAILEAPEKQRTLNEIYHWFTRMFAFFRNHPATWKNAIRHN LSLHKCFVRVESEKGAVWTVDELEFRKKRSQRPSRCSNPTPGP |
| SEQ ID NO: 2 | FOXP3 full length nucleic acid | atgcctaaccccgccctggaaaaccatctgcccc ttcactggccctgggaccttcacccggagcctcac catcttggagagccgcccccaaggccagcgacctg ctgggagccagaggccccggcggcaccttccaggg cagggatctgcgcggcggcgcccacgccagctcct ctagcctgaaccccatgcccccttctcagctccag ctgcccacactgcccctggtcatggtggcacctag cggagcaaggctgggaccactgccacacctccagg ccctgctccaggacagacctcactttatgcaccag ctgtccaccgtggatgcacacgcaaggacacccgt gctccaggtgcaccctctggagtctccagccatga tcagcctgaccccaccaaccacagcaacaggcgtg ttctccctgaaggccagacctggcctgcctccagg catcaacgtggcctccctggagtgggtgtctaggg agccagccctgctgtgcaccttcctaatccatct gccccccgcaaggactccacactgtctgccgtgcc acagtcctcttacccctgctggccaacggcgtgt gcaagtggcctggctgtgagaaggtgttcgaggag ccagaggattttctgaagcactgccaggccgacca cctgctggatgagaagggaagggcacagtgtctgc tccagagggagatggtgcagagcctggagcagcag ctggtgctggagaaggagaagctgtccgccatgca ggcacacctggcaggcaagatggcactgaccaagg ccagctccgtggcctctagcgacaagggcagctgc tgtatcgtggccgccggctcccagggaccagtggt gcccgcctggtctggacccagggaggcacctgaca gcctgttcgccgtgcggagacacctgtgggcagc cacggcaattccaccttccccgagtttctgcacaa catggattacttcaagtttcacaatatgcggcccc cttttacctatgccacactgatcagatgggccatc ctggaggcccagagaagcagcgcaccctgaacga aatctaccactggttcacacggatgtttgccttct ttagaaatcacccgccacctggaagaacgccatc aggcacaatctgtccctgcacaagtgtttcgtgcg cgtggagtctgagaagggcgccgtgtggacagtgg atgagctggagttcagaaagaagagaagccagaga ccatccaggtgttcaaaccctaccccaggaccc |
| SEQ ID NO: 3 | FOXP3 exon 2 | CCTGCCCTTGGACAAGGACCCGATGCCCAACCCCAGGCCTG GCAAGCCCTCGGCCCCTTCCTTGGCCCTTGGCCCATCCCCAG GAGCCTCGCCCAGCTGGAGGGCTGCACCCAAAGCCTCAGAC CTGCTGGGGGCCCGGGGCCCAGGGGGAACCTTCCAGGGCCG AGATCTTCGAGGCGGGCCCATGCCTCCTCTTCTTCCTTGAA CCCCATGCCACCATCGCAGCTGCAG |
| SEQ ID NO: 4 | CD3 zeta cytoplasmic signaling domain | mkwkalftaailqaqlpiteaqsfglldpklcylldgilfiy gviltalflrvkfsrsadapayqqgqnqlynelnlgrreeyd vldkrrgrdpemggkpqrrknpqeglynelqkdkmaeaysei gmkgerrrgkghdglyqglstatkdtydalhmqalppr |
| SEQ ID NO: 5 | CD28 co-stimulatory domain | IEVMYPPPYLDNEKSNGTIIHVKGKHLCPSPLFPGPSKPFWVLV VVGGVLACYSLLVTVAFIIFWVRSKRSRLLHSDYMNMTPRRPG PTRKHYQPYAPPRDFAAY |

Sequence Appendix

| SEQ ID NO: | Name | Sequence |
|---|---|---|
| SEQ ID NO: 6 | MAdCA M1 scFv 32.3 | EVQLLESGGGLVQPGGSLRLSCAASGFSFSSSYWICWVRQAPG KGLEWVSCIYGGSSGATYYANWAKGRFTISRDNSKNTLYLQM NSLRAEDTAVYYCARSGSTTSGGVYRWYFNLWGQGTLVTVSS GGGGSGGGGSGGGGSDIQMTQSPSSLSASVGDRVTITCQASENI YNLLAWYQQKPGKVPKLLIYDASTLQSGVPSRFSGSGSGTDFT LTISSLQPEDVATYYCQFTYYGGTYESAFGGGTKVEIK |
| SEQ ID NO: 7 | MAdCA M1 scFv 32.4 | EVQLLESGGGLVQPGGSLRLSCAASGFSFSSSYWICWVRQAPG KGLEWVSCIYGGSSGATYYANWAKGRFTISRDNSKNTLYLQM NSLRAEDTAVYYCARSGSTTSGGVYRWYFNLWGQGTLVTVSS GGGGSGGGGSGGGGSDIQMTQSPSSLSASVGDRVTITCQASENI YNLLAWYQQKPGKAPKLLIYDASNLETGVPSRFSGSGSGTDFT FTISSLQPEDIATYYCQFTYYGGTYESAFGGGTKVEIK |
| SEQ ID NO: 8 | MAdCA M1 scFv 32.5 | QVQLVESGGGVVQPGRSLRLSCAASGFSFSSSYWICWVRQAPG KGLEWVACIYGGSSGATYYANWAKGRFTISRDNSTNTLFLQM NSLRAEDTAVYYCARSGSTTSGGVYRWYFNLWGQGTLVTVSS GGGGSGGGGSGGGGSDIQMTQSPSSLSASVGDRVTITCQASENI YNLLAWYQQKPGKVPKLLIYDASTLQSGVPSRFSGSGSGTDFT LTISSLQPEDVATYYCQFTYYGGTYESAFGGGTKVEIK |
| SEQ ID NO: 9 | MAdCA M1 scFv 32.6 | QVQLVESGGGVVQPGRSLRLSCAASGFSFSSSYWICWVRQAPG KGLEWVACIYGGSSGATYYANWAKGRFTISRDNSTNTLFLQM NSLRAEDTAVYYCARSGSTTSGGVYRWYFNLWGQGTLVTVSS GGGGSGGGGSGGGGSDIQMTQSPSSLSASVGDRVTITCQASENI YNLLAWYQQKPGKAPKLLIYDASNLETGVPSRFSGSGSGTDFT FTISSLQPEDIATYYCQFTYYGGTYESAFGGGTKVEIK |
| SEQ ID NO: 10 | MAdCA M1 scFv 32.7 | EVQLVESGGGLVQPGGSLRLSCAASGFSFSSSYWICWVRQAPG KGLEWVSCIYGGSSGATYYANWAKGRFTISRHNSKNTLYLQM NSLRAEDTAVYYCARSGSTTSGGVYRWYFNLWGQGTLVTVSS GGGGSGGGGSGGGGSDIQMTQSPSSLSASVGDRVTITCQASENI YNLLAWYQQKPGKVPKLLIYDASTLQSGVPSRFSGSGSGTDFT LTISSLQPEDVATYYCQFTYYGGTYESAFGGGTKVEIK |
| SEQ ID NO: 11 | MAdCA M1 scFv 32.8 | EVQLVESGGGLVQPGGSLRLSCAASGFSFSSSYWICWVRQAPG KGLEWVSCIYGGSSGATYYANWAKGRFTISRHNSKNTLYLQM NSLRAEDTAVYYCARSGSTTSGGVYRWYFNLWGQGTLVTVSS GGGGSGGGGSGGGGSDIQMTQSPSSLSASVGDRVTITCQASENI YNLLAWYQQKPGKAPKLLIYDASNLETGVPSRFSGSGSGTDFT FTISSLQPEDIATYYCQFTYYGGTYESAFGGGTKVEIK |
| SEQ ID NO: 12 | MAdCA M1 scFv 8.1 | EVQLVESGGGLVQPGGSLRLSCAASGFTLSSSYYMYWVRQAP GKGLEWVSVIYAGDGNTYYASWAKGRFTISRDNSKNTLYLQM NSLRAEDTAVYYCARGYVGYGYAIDLWGQGTLVTVSSGGGGS GGGGSGGGGSDIQMTQSPSTLSASVGDRVTITCQASQSIYSSLA WYQQKPGKAPKLLIYYASILPSGVPSRFSGSGSGTEFTLTISSLQ PDDFATYYCQATTYDSTYPNAFGGGTKVEIK |
| SEQ ID NO: 13 | MAdCA M1 scFv 8.2 | EVQLVESGGGLVQPGGSLRLSCAASGFTLSSSYYMYWVRQAP GKGLEWVSVIYAGDGNTYYASWAKGRFTISRDNSKNTLYLQM NSLRAEDTAVYYCARGYVGYGYAIDLWGQGTLVTVSSGGGGS GGGGSGGGGSAIQLTQSPSSLSASVGDRVTITCQASQSIYSSLA WYQQKPGKAPKLLIYYASILPSGVPSRFSGSGSGTDFTLTISSLQ PEDFATYYCQATTYDSTYPNAFGGGTKVEIK |
| SEQ ID NO: 14 | MAdCA M1 scFv 8.4 | EVQLLESGGGLVQPGGSLRLSCAASGFTLSSSYYMYWVRQAPG KGLEWVSAIYAGDGNTYYASWAKGRFTISRDNSKNTLYLQMN SLRAEDTAVYYCARGYVGYGYAIDLWGQGTLVTVSSGGGGSG GGGSGGGGSAIQLTQSPSSLSASVGDRVTITCQASQSIYSSLAW YQQKPGKAPKLLIYYASILPSGVPSRFSGSGSGTDFTLTISSLQ PEDFATYYCQATTYDSTYPNAFGGGTKVEIK |
| SEQ ID NO: 15 | MAdCA M1 scFv 8.5 | QVQLVESGGGVVQPGRSLRLSCAASGFTLSSSYYMYWVRQAP GKGLEWVAVIYAGDGNTYYASWAKGRFTISRDNSKNTLYLQM NSLRAEDTAVYYCARGYVGYGYAIDLWGQGTLVTVSSGGGGS GGGGSGGGGSDIQMTQSPSTLSASVGDRVTITCQASQSIYSSLA WYQQKPGKAPKLLIYYASILPSGVPSRFSGSGSGTEFTLTISSLQ PDDFATYYCQATTYDSTYPNAFGGGTKVEIK |

Sequence Appendix

| SEQ ID NO: | Name | Sequence |
|---|---|---|
| SEQ ID NO: 16 | MAdCA M1 scFv 8.6 | QVQLVESGGGVVQPGRSLRLSCAASGFTLSSSYYMYWVRQAP GKGLEWVAVIYAGDGNTYYASWAKGRFTISRDNSKNTLYLQM NSLRAEDTAVYYCARGYVGYGYAIDLWGQGTLVTVSSGGGGS GGGGSGGGGSAIQLTQSPSSLSASVGDRVTITCQASQSIYSSLA WYQQKPGKAPKLLIYYASILPSGVPSRFSGSGSGTDFTLTISSLQ PEDFATYYCQATTYDSTYPNAFGGGTKVEIK |
| SEQ ID NO: 17 | MAdCA M1 scFv 8.7 | EVQLVETGGGLIQPGGSLRLSCAASGFTLSSSYYMYWVRQAPG KGLEWVSVIYAGDGNTYYASWAKGRFTISRDNSKNTLYLQMN SLRAEDTAVYYCARGYVGYGYAIDLWGQGTLVTVSSGGGGSG GGGSGGGGSDIQMTQSPSTLSASVGDRVTITCQASQSIYSSLAW YQQKPGKAPKLLIYYASILPSGVPSRFSGSGSGTEFTLTISSLQ PDDFATYYCQATTYDSTYPNAFGGGTKVEIK |
| SEQ ID NO: 18 | MAdCA M1 scFv 8.8 | EVQLVETGGGLIQPGGSLRLSCAASGFTLSSSYYMYWVRQAPG KGLEWVSVIYAGDGNTYYASWAKGRFTISRDNSKNTLYLQMN SLRAEDTAVYYCARGYVGYGYAIDLWGQGTLVTVSSGGGGSG GGGSGGGGSAIQLTQSPSSLSASVGDRVTITCQASQSIYSSLAW YQQKPGKAPKLLIYYASILPSGVPSRFSGSGSGTDFTLTISSLQ PEDFATYYCQATTYDSTYPNAFGGGTKVEIK |
| SEQ ID NO: 19 | MAdCA M1 scFv 17.1 | EVQLVESGGGLVQPGGSLRLSCAASGFSFSSTYYMCWVRQAPG KGLEWVSCIYTGSGNTDYASWAKGRFTISRHNSKNTLYLQMNS LRAEDTAVYYCARGGIVDSYFTYFDLWGQGTLVTVSSGGGGS GGGGSGGGGSDIQMTQSPSTLSASVGDRVTITCQASESIFSNLA WYQQKPGKAPKLLIYWASTLASGVPSRFSGSGSGTEFTLTISSL QPDDFATYYCQSYVYSSSSSNDFGGGTKVEIK |
| SEQ ID NO: 20 | MAdCA M1 scFv 17.3 | QVQLLESGGGLVKPGGSLRLSCAASGFSFSSTYYMCWIRQAPG KGLEWVSCIYTGSGNTDYASWAKGRFTISRDNAKNSLYLQMN SLRAEDTAVYYCARGGIVDSYFTYFDLWGQGTLVTVSSGGGGS GGGGSGGGGSDIQMTQSPSTLSASVGDRVTITCQASESIFSNLA WYQQKPGKAPKLLIYWASTLASGVPSRFSGSGSGTEFTLTISSL QPDDFATYYCQSYVYSSSSSNDFGGGTKVEIK |
| SEQ ID NO: 21 | MAdCA M1 scFv 17.5 | QVQLVESGGGVVQPGRSLRLSCAASGFSFSSTYYMCWVRQAP GKGLEWVACIYTGSGNTDYASWAKGRFTISRDNSTNTLFLQM NSLRAEDTAVYYCARGGIVDSYFTYFDLWGQGTLVTVSSGGG GSGGGGSGGGGSDIQMTQSPSTLSASVGDRVTITCQASESIFSNL AWYQQKPGKAPKLLIYWASTLASGVPSRFSGSGSGTEFTLTISS LQPDDFATYYCQSYVYSSSSSNDFGGGTKVEIK |
| SEQ ID NO: 22 | MAdCA M1 scFv 17.7 | EVQLVESGGGLVKPGGSLRLSCAASGFSFSSTYYMCWVRQAPG KGLEWVSCIYTGSGNTDYASWAKGRFTISRDNAKNSLYLQMN SLRAEDTAVYYCARGGIVDSYFTYFDLWGQGTLVTVSSGGGGS GGGGSGGGGSDIQMTQSPSTLSASVGDRVTITCQASESIFSNLA WYQQKPGKAPKLLIYWASTLASGVPSRFSGSGSGTEFTLTISSL QPDDFATYYCQSYVYSSSSSNDFGGGTKVEIK |
| SEQ ID NO: 23 | MAdCA M1 scFv 2.1 | QVQLLESGGGLVKPGGSLRLSCAASGFSFSSGYYMCWIRQAPG KGLEWVSCIYADSSYTYYASWAKGRFTISRDNAKNSLYLQMN SLRAEDTAVYYCARSNGDYFYGMDLWGQGTLVTVSSGGGGS GGGGSGGGGSDIQMTQSPSSLSASVGDRVTITCQASQSINSWLS WYQQKPGKAPKLLIYRASTLASGVPSRFSGSGSGTDFTFTISSLQ PEDIATYYCQSNYYSTSTAFGGGTKVEIK |
| SEQ ID NO: 24 | MAdCA M1 scFv 2.2 | QVQLLESGGGLVKPGGSLRLSCAASGFSFSSGYYMCWIRQAPG KGLEWVSCIYADSSYTYYASWAKGRFTISRDNAKNSLYLQMN SLRAEDTAVYYCARSNGDYFYGMDLWGQGTLVTVSSGGGGS GGGGSGGGGSAIQMTQSPSSLSASVGDRVTITCQASQSINSWLS WYQQKPGKAPKLLIYRASTLASGVPSRFSGSGSGTDFTLTISSLQ PEDFATYYCQSNYYSTSTAFGGGTKVEIK |
| SEQ ID NO: 25 | MAdCA M1 scFv 10.1 | QVQLVESGGGVVQPGRSLRLSCAASGIDFSGYHYICWVRQAPG KGLEWVACIYTVSSGIWYATWAKGRFTISRDNSTNTLFLQMNS LRAEDTAVYYCARDDADVSGYWFDLWGQGTLVTVSSGGGGS GGGGSGGGGSDIQMTQSPSSLSASVGDRVTITCQASQSISNLLA WYQQKPGKAPKLLIYKASTLASGVPSRFSGSGSGTDFTFTISSLQ PEDIATYYCQQGITNNGIDHGFGGGTKVEIK |

Sequence Appendix

| SEQ ID NO: | Name | Sequence |
|---|---|---|
| SEQ ID NO: 26 | MAdCA M1 scFv 10.2 | QVQLVESGGGVVQPGRSLRLSCAASGIDFSGYHYICWVRQAPG KGLEWVACIYTVSSGIWYATWAKGRFTISRDNSTNTLFLQMNS LRAEDTAVYYCARDDADVSGYWFDLWGQGTLVTVSSGGGGS GGGGSGGGGSAIQLTQSPSSLSASVGDRVTITCQASQSISNLLA WYQQKPGKAPKLLIYKASTLASGVPSRFSGSGSGTDFTLTISSL QPEDFATYYCQQGITNNGIDHGFGGGTKVEIK |
| SEQ ID NO: 27 | MAdCA M1 scFv 10.3 | EVQLVESGGGLVKPGGSLRLSCAASGIDFSGYHYICWVRQAPG KGLEWVSCIYTVSSGIWYATWAKGRFTISRDNAKNSLYLQMNS LRAEDTAVYYCARDDADVSGYWFDLWGQGTLVTVSSGGGGS GGGGSGGGGSDIQMTQSPSSLSASVGDRVTITCQASQSISNLLA WYQQKPGKAPKLLIYKASTLASGVPSRFSGSGSGTDFTFTISSLQ PEDIATYYCQQGITNNGIDHGFGGGTKVEIK |
| SEQ ID NO: 28 | MAdCA M1 scFv 10.7 | EVQLLESGGGLVQPGGSLRLSCAASGIDFSGYHYICWVRQAPG KGLEWVSCIYTVSSGIWYATWAKGRFTISRDNSKNTLYLQMNS LRAEDTAVYYCARDDADVSGYWFDLWGQGTLVTVSSGGGGS GGGGSGGGGSDIQMTQSPSSLSASVGDRVTITCQASQSISNLLA WYQQKPGKAPKLLIYKASTLASGVPSRFSGSGSGTDFTFTISSLQ PEDIATYYCQQGITNNGIDHGFGGGTKVEIK |
| SEQ ID NO: 29 | MAdCA M1 scFv 10.8 | EVQLLESGGGLVQPGGSLRLSCAASGIDFSGYHYICWVRQAPG KGLEWVSCIYTVSSGIWYATWAKGRFTISRDNSKNTLYLQMNS LRAEDTAVYYCARDDADVSGYWFDLWGQGTLVTVSSGGGGS GGGGSGGGGSAIQLTQSPSSLSASVGDRVTITCQASQSISNLLA WYQQKPGKAPKLLIYKASTLASGVPSRFSGSGSGTDFTLTISSL QPEDFATYYCQQGITNNGIDHGFGGGTKVEIK |
| SEQ ID NO: 30 | MAdCA M1 scFv 32.3 HC | EVQLLESGGGLVQPGGSLRLSCAASGFSFSSSYWICWVRQAPG KGLEWVSCIYGGSSGATYYANWAKGRFTISRDNSKNTLYLQM NSLRAEDTAVYYCARSGSTTSGGVYRWYFNLWGQGTLVTVSS |
| SEQ ID NO: 31 | MAdCA M1 scFv 32.3 LC | DIQMTQSPSSLSASVGDRVTITCQASENIYNLLAWYQQKPGKVP KLLIYDASTLQSGVPSRFSGSGSGTDFTLTISSLQPEDVATYYCQ FTYYGGTYESAFGGGTKVEIK |
| SEQ ID NO: 32 | MAdCA M1 scFv 32.4 HC | EVQLLESGGGLVQPGGSLRLSCAASGFSFSSSYWICWVRQAPG KGLEWVSCIYGGSSGATYYANWAKGRFTISRDNSKNTLYLQM NSLRAEDTAVYYCARSGSTTSGGVYRWYFNLWGQGTLVTVSS |
| SEQ ID NO: 33 | MAdCA M1 scFv 32.4 LC | DIQMTQSPSSLSASVGDRVTITCQASENIYNLLAWYQQKPGKAP KLLIYDASNLETGVPSRFSGSGSGTDFTFTISSLQPEDIATYYCQF TYYGGTYESAFGGGTKVEIK |
| SEQ ID NO: 34 | MAdCA M1 scFv 32.5 HC | QVQLVESGGGVVQPGRSLRLSCAASGFSFSSSYWICWVRQAPG KGLEWVACIYGGSSGATYYANWAKGRFTISRDNSTNTLFLQM NSLRAEDTAVYYCARSGSTTSGGVYRWYFNLWGQGTLVTVSS |
| SEQ ID NO: 35 | MAdCA M1 scFv 32.5 LC | DIQMTQSPSSLSASVGDRVTITCQASENIYNLLAWYQQKPGKVP KLLIYDASTLQSGVPSRFSGSGSGTDFTLTISSLQPEDVATYYCQ FTYYGGTYESAFGGGTKVEIK |
| SEQ ID NO: 36 | MAdCA M1 scFv 32.6 HC | QVQLVESGGGVVQPGRSLRLSCAASGFSFSSSYWICWVRQAPG KGLEWVACIYGGSSGATYYANWAKGRFTISRDNSTNTLFLQM NSLRAEDTAVYYCARSGSTTSGGVYRWYFNLWGQGTLVTVSS |
| SEQ ID NO: 37 | MAdCA M1 scFv 32.6 LC | DIQMTQSPSSLSASVGDRVTITCQASENIYNLLAWYQQKPGKAP KLLIYDASNLETGVPSRFSGSGSGTDFTFTISSLQPEDIATYYC QFTYYGGTYESAFGGGTKVEIK |
| SEQ ID NO: 38 | MAdCA M1 scFv 32.7 HC | EVQLVESGGGLVQPGGSLRLSCAASGFSFSSSYWICWVRQAPG KGLEWVSCIYGGSSGATYYANWAKGRFTISRHNSKNTLYLQM NSLRAEDTAVYYCARSGSTTSGGVYRWYFNLWGQGTLVTVSS |
| SEQ ID NO: 39 | MAdCA M1 scFv 32.7 LC | DIQMTQSPSSLSASVGDRVTITCQASENIYNLLAWYQQKPGKVP KLLIYDASTLQSGVPSRFSGSGSGTDFTLTISSLQPEDVATYYCQ FTYYGGTYESAFGGGTKVEIK |
| SEQ ID NO: 40 | MAdCA M1 scFv 32.8 HC | EVQLVESGGGLVQPGGSLRLSCAASGFSFSSSYWICWVRQAPG KGLEWVSCIYGGSSGATYYANWAKGRFTISRHNSKNTLYLQM NSLRAEDTAVYYCARSGSTTSGGVYRWYFNLWGQGTLVTVSS |

Sequence Appendix

| SEQ ID NO: | Name | Sequence |
|---|---|---|
| SEQ ID NO: 41 | MAdCA M1 scFv 32.8 LC | DIQMTQSPSSLSASVGDRVTITCQASENIYNLLAWYQQKPGKAPKLLIYDASNLETGVPSRFSGSGSGTDFTFTISSLQPEDIATYYCQFTYYGGTYESAFGGGTKVEIK |
| SEQ ID NO: 42 | MAdCA M1 scFv 8.1 HC | EVQLVESGGGLVQPGGSLRLSCAASGFTLSSSYYMYWVRQAPGKGLEWVSVIYAGDGNTYYASWAKGRFTISRDNSKNTLYLQMNSLRAEDTAVYYCARGYVGYGYAIDLWGQGTLVTVSS |
| SEQ ID NO: 43 | MAdCA M1 scFv 8.1 LC | DIQMTQSPSTLSASVGDRVTITCQASQSIYSSLAWYQQKPGKAPKLLIYYASILPSGVPSRFSGSGSGTEFTLTISSLQPDDFATYYCQATTYDSTYPNAFGGGTKVEIK |
| SEQ ID NO: 44 | MAdCA M1 scFv 8.2 HC | EVQLVESGGGLVQPGGSLRLSCAASGFTLSSSYYMYWVRQAPGKGLEWVSVIYAGDGNTYYASWAKGRFTISRDNSKNTLYLQMNSLRAEDTAVYYCARGYVGYGYAIDLWGQGTLVTVSS |
| SEQ ID NO: 45 | MAdCA M1 scFv 8.2 LC | AIQLTQSPSSLSASVGDRVTITCQASQSIYSSLAWYQQKPGKAPKLLIYYASILPSGVPSRFSGSGSGTDFTLTISSLQPEDFATYYCQATTYDSTYPNAFGGGTKVEIK |
| SEQ ID NO: 46 | MAdCA M1 scFv 8.4 HC | EVQLLESGGGLVQPGGSLRLSCAASGFTLSSSYYMYWVRQAPGKGLEWVSAIYAGDGNTYYASWAKGRFTISRDNSKNTLYLQMNSLRAEDTAVYYCARGYVGYGYAIDLWGQGTLVTVSS |
| SEQ ID NO: 47 | MAdCA M1 scFv 8.4 LC | AIQLTQSPSSLSASVGDRVTITCQASQSIYSSLAWYQQKPGKAPKLLIYYASILPSGVPSRFSGSGSGTDFTLTISSLQPEDFATYYCQATTYDSTYPNAFGGGTKVEIK |
| SEQ ID NO: 48 | MAdCA M1 scFv 8.5 HC | QVQLVESGGGVVQPGRSLRLSCAASGFTLSSSYYMYWVRQAPGKGLEWVAVIYAGDGNTYYASWAKGRFTISRDNSKNTLYLQMNSLRAEDTAVYYCARGYVGYGYAIDLWGQGTLVTVSS |
| SEQ ID NO: 49 | MAdCA M1 scFv 8.5 LC | DIQMTQSPSTLSASVGDRVTITCQASQSIYSSLAWYQQKPGKAPKLLIYYASILPSGVPSRFSGSGSGTEFTLTISSLQPDDFATYYCQATTYDSTYPNAFGGGTKVEIK |
| SEQ ID NO: 50 | MAdCA M1 scFv 8.6 HC | QVQLVESGGGVVQPGRSLRLSCAASGFTLSSSYYMYWVRQAPGKGLEWVAVIYAGDGNTYYASWAKGRFTISRDNSKNTLYLQMNSLRAEDTAVYYCARGYVGYGYAIDLWGQGTLVTVSS |
| SEQ ID NO: 51 | MAdCA M1 scFv 8.6 LC | AIQLTQSPSSLSASVGDRVTITCQASQSIYSSLAWYQQKPGKAPKLLIYYASILPSGVPSRFSGSGSGTDFTLTISSLQPEDFATYYCQATTYDSTYPNAFGGGTKVEIK |
| SEQ ID NO: 52 | MAdCA M1 scFv 8.7 HC | EVQLVETGGGLIQPGGSLRLSCAASGFTLSSSYYMYWVRQAPGKGLEWVSVIYAGDGNTYYASWAKGRFTISRDNSKNTLYLQMNSLRAEDTAVYYCARGYVGYGYAIDLWGQGTLVTVSS |
| SEQ ID NO: 53 | MAdCA M1 scFv 8.7 LC | DIQMTQSPSTLSASVGDRVTITCQASQSIYSSLAWYQQKPGKAPKLLIYYASILPSGVPSRFSGSGSGTEFTLTISSLQPDDFATYYCQATTYDSTYPNAFGGGTKVEIK |
| SEQ ID NO: 54 | MAdCA M1 scFv 8.8 HC | EVQLVETGGGLIQPGGSLRLSCAASGFTLSSSYYMYWVRQAPGKGLEWVSVIYAGDGNTYYASWAKGRFTISRDNSKNTLYLQMNSLRAEDTAVYYCARGYVGYGYAIDLWGQGTLVTVSS |
| SEQ ID NO: 55 | MAdCA M1 scFv 8.8 LC | AIQLTQSPSSLSASVGDRVTITCQASQSIYSSLAWYQQKPGKAPKLLIYYASILPSGVPSRFSGSGSGTDFTLTISSLQPEDFATYYCQATTYDSTYPNAFGGGTKVEIK |
| SEQ ID NO: 56 | MAdCA M1 scFv 17.1 HC | EVQLVESGGGLVQPGGSLRLSCAASGFSFSSTYYMCWVRQAPGKGLEWVSCIYTGSGNTDYASWAKGRFTISRHNSKNTLYLQMNSLRAEDTAVYYCARGGIVDSYFTYFDLWGQGTLVTVSS |
| SEQ ID NO: 57 | MAdCA M1 scFv 17.1 LC | DIQMTQSPSTLSASVGDRVTITCQASESIFSNLAWYQQKPGKAPKLLIYWASTLASGVPSRFSGSGSGTEFTLTISSLQPDDFATYYCQSYVYSSSSSNDFGGGTKVEIK |
| SEQ ID NO: 58 | MAdCA M1 scFv 17.3 HC | QVQLLESGGGLVKPGGSLRLSCAASGFSFSSTYYMCWIRQAPGKGLEWVSCIYTGSGNTDYASWAKGRFTISRDNAKNSLYLQMNSLRAEDTAVYYCARGGIVDSYFTYFDLWGQGTLVTVSS |

| SEQ ID NO: | Name | Sequence |
|---|---|---|
| SEQ ID NO: 59 | MAdCA M1 scFv 17.3 LC | DIQMTQSPSTLSASVGDRVTITCQASESIFSNLAWYQQKPGKAP KLLIYWASTLASGVPSRFSGSGSGTEFTLTISSLQPDDFATYYCQ SYVYSSSSSNDFGGGTKVEIK |
| SEQ ID NO: 60 | MAdCA M1 scFv 17.5 HC | QVQLVESGGGVVQPGRSLRLSCAASGFSFSSTYYMCWVRQAP GKGLEWVACIYTGSGNTDYASWAKGRFTISRDNSTNTLFLQM NSLRAEDTAVYYCARGGIVDSYFTYFDLWGQGTLVTVSS |
| SEQ ID NO: 61 | MAdCA M1 scFv 17.5 LC | DIQMTQSPSTLSASVGDRVTITCQASESIFSNLAWYQQKPGKAP KLLIYWASTLASGVPSRFSGSGSGTEFTLTISSLQPDDFATYYCQ SYVYSSSSSNDFGGGTKVEIK |
| SEQ ID NO: 62 | MAdCA M1 scFv 17.7 HC | EVQLVESGGGLVKPGGSLRLSCAASGFSFSSTYYMCWVRQAPG KGLEWVSCIYTGSGNTDYASWAKGRFTISRDNAKNSLYLQMN SLRAEDTAVYYCARGGIVDSYFTYFDLWGQGTLVTVSS |
| SEQ ID NO: 63 | MAdCA M1 scFv 17.7 LC | DIQMTQSPSTLSASVGDRVTITCQASESIFSNLAWYQQKPGKAP KLLIYWASTLASGVPSRFSGSGSGTEFTLTISSLQPDDFATYYCQ SYVYSSSSSNDFGGGTKVEIK |
| SEQ ID NO: 64 | MAdCA M1 scFv 2.1 HC | QVQLLESGGGLVKPGGSLRLSCAASGFSFSSGYYMCWIRQAPG KGLEWVSCIYADSSYTYYASWAKGRFTISRDNAKNSLYLQMN SLRAEDTAVYYCARSNGDYFYGMDLWGQGTLVTVSS |
| SEQ ID NO: 65 | MAdCA M1 scFv 2.1 LC | DIQMTQSPSSLSASVGDRVTITCQASQSINSWLSWYQQKPGKAP KLLIYRASTLASGVPSRFSGSGSGTDFTFTISSLQPEDIATYYCQS NYYSTSTAFGGGTKVEIK |
| SEQ ID NO: 66 | MAdCA M1 scFv 2.2 HC | QVQLLESGGGLVKPGGSLRLSCAASGFSFSSGYYMCWIRQAPG KGLEWVSCIYADSSYTYYASWAKGRFTISRDNAKNSLYLQMN SLRAEDTAVYYCARSNGDYFYGMDLWGQGTLVTVSS |
| SEQ ID NO: 67 | MAdCA M1 scFv 2.2 LC | AIQMTQSPSSLSASVGDRVTITCQASQSINSWLSWYQQKPGKAP KLLIYRASTLASGVPSRFSGSGSGTDFTLTISSLQPEDFATYYCQ SNYYSTSTAFGGGTKVEIK |
| SEQ ID NO: 68 | MAdCA M1 scFv 10.1 HC | QVQLVESGGGVVQPGRSLRLSCAASGIDFSGYHYICWVRQAPG KGLEWVACIYTVSSGIWYATWAKGRFTISRDNSTNTLFLQMNS LRAEDTAVYYCARDDADVSGYWFDLWGQGTLVTVSS |
| SEQ ID NO: 69 | MAdCA M1 scFv 10.1 LC | DIQMTQSPSSLSASVGDRVTITCQASQSISNLLAWYQQKPGKAP KLLIYKASTLASGVPSRFSGSGSGTDFTFTISSLQPEDIATYYCQQ GITNNGIDHGFGGGTKVEIK |
| SEQ ID NO: 70 | MAdCA M1 scFv 10.2 HC | QVQLVESGGGVVQPGRSLRLSCAASGIDFSGYHYICWVRQAPG KGLEWVACIYTVSSGIWYATWAKGRFTISRDNSTNTLFLQMNS LRAEDTAVYYCARDDADVSGYWFDLWGQGTLVTVSS |
| SEQ ID NO: 71 | MAdCA M1 scFv 10.2 LC | AIQLTQSPSSLSASVGDRVTITCQASQSISNLLAWYQQKPGKAP KLLIYKASTLASGVPSRFSGSGSGTDFTLTISSLQPEDFATYYCQ QGITNNGIDHGFGGGTKVEIK |
| SEQ ID NO: 72 | MAdCA M1 scFv 10.3 HC | EVQLVESGGGLVKPGGSLRLSCAASGIDFSGYHYICWVRQAPG KGLEWVSCIYTVSSGIWYATWAKGRFTISRDNAKNSLYLQMNS LRAEDTAVYYCARDDADVSGYWFDLWGQGTLVTVSS |
| SEQ ID NO: 73 | MAdCA M1 scFv 10.3 LC | DIQMTQSPSSLSASVGDRVTITCQASQSISNLLAWYQQKPGKAP KLLIYKASTLASGVPSRFSGSGSGTDFTFTISSLQPEDIATYYCQQ GITNNGIDHGFGGGTKVEIK |
| SEQ ID NO: 74 | MAdCA M1 scFv 10.7 HC | EVQLLESGGGLVQPGGSLRLSCAASGIDFSGYHYICWVRQAPG KGLEWVSCIYTVSSGIWYATWAKGRFTISRDNSKNTLYLQMNS LRAEDTAVYYCARDDADVSGYWFDLWGQGTLVTVSS |
| SEQ ID NO: 75 | MAdCA M1 scFv 10.7 LC | DIQMTQSPSSLSASVGDRVTITCQASQSISNLLAWYQQKPGKAP KLLIYKASTLASGVPSRFSGSGSGTDFTFTISSLQPEDIATYYCQQ GITNNGIDHGFGGGTKVEIK |
| SEQ ID NO: 76 | MAdCA M1 scFv 10.8 HC | EVQLLESGGGLVQPGGSLRLSCAASGIDFSGYHYICWVRQAPG KGLEWVSCIYTVSSGIWYATWAKGRFTISRDNSKNTLYLQMNS LRAEDTAVYYCARDDADVSGYWFDLWGQGTLVTVSS |

Sequence Appendix

| SEQ ID NO: | Name | Sequence |
|---|---|---|
| SEQ ID NO: 77 | MAdCA M1 scFv 10.8 LC | AIQLTQSPSSLSASVGDRVTITCQASQSISNLLAWYQQKPGKAP KLLIYKASTLASGVPSRFSGSGSGTDFTLTISSLQPEDFATYYCQ QGITNNGIDHGFGGGTKVEIK |

What is claimed is:

1. A polypeptide comprising an antigen-binding domain comprising a heavy chain variable domain comprising the three heavy chain CDR sequences present in SEQ ID NO: 34 and a light chain variable domain comprising the three light chain CDR sequences present in SEQ ID NO: 35.

2. The polypeptide of claim 1, wherein the heavy chain variable domain comprises a sequence that is at least 80% identical to SEQ ID NO: 34 and the light chain variable domain comprises a sequence that is at least 80% identical to SEQ ID NO: 35.

3. The polypeptide of claim 1, wherein the heavy chain variable domain comprises a sequence that is at least 85% identical to SEQ ID NO: 34 and the light chain variable domain comprises a sequence that is at least 85% identical to SEQ ID NO: 35.

4. The polypeptide of claim 1, wherein the heavy chain variable domain comprises a sequence that is at least 90% identical to SEQ ID NO: 34 and the light chain variable domain comprises a sequence that is at least 90% identical to SEQ ID NO: 35.

5. The polypeptide of claim 1, wherein the heavy chain variable domain comprises a sequence that is at least 95% identical to SEQ ID NO: 34 and the light chain variable domain comprises a sequence that is at least 95% identical to SEQ ID NO: 35.

6. The polypeptide of claim 1, wherein the heavy chain variable domain comprises SEQ ID NO: 34 and the light chain variable domain comprises SEQ ID NO: 35.

7. The polypeptide of claim 1, wherein the antigen-binding domain comprises a sequence that is at least 80% identical to SEQ ID NO: 8.

8. The polypeptide of claim 1, wherein the antigen-binding domain comprises a sequence that is at least 85% identical to SEQ ID NO: 8.

9. The polypeptide of claim 1, wherein the antigen-binding domain comprises a sequence that is at least 90% identical to SEQ ID NO: 8.

10. The polypeptide of claim 1, wherein the antigen-binding domain comprises a sequence that is at least 95% identical to SEQ ID NO: 8.

11. The polypeptide of claim 1, wherein the antigen-binding domain comprises SEQ ID NO: 8.

12. The polypeptide of claim 1, wherein the polypeptide is an antibody.

13. The polypeptide of claim 12, wherein the antibody is a humanized antibody.

14. The polypeptide of claim 1, wherein the polypeptide is an antigen-binding fragment of an antibody.

15. The polypeptide of claim 14, wherein the antigen-binding fragment is a Fab, a F(ab')$_2$ fragment, a scFv, or a scAb.

16. The polypeptide of claim 14, wherein the antigen-binding fragment is a humanized antigen-binding fragment.

17. The polypeptide of claim 1, wherein the polypeptide is a chimeric antigen receptor comprising an extracellular domain comprising the antigen-binding domain.

18. The polypeptide of claim 17, wherein the antigen-binding domain is humanized.

19. A nucleic acid comprising a sequence encoding the polypeptide of claim 1.

20. A nucleic acid comprising a sequence encoding the polypeptide of claim 17.

21. A cell comprising the nucleic acid of claim 19, wherein the cell expresses the polypeptide.

22. A cell comprising the nucleic acid of claim 20, wherein the cell expresses the chimeric antigen receptor.

23. The cell of claim 21, wherein the cell is a T cell.

24. The cell of claim 22, wherein the cell is a T cell.

* * * * *

SEQUENCE LISTING

```
Sequence total quantity: 77
SEQ ID NO: 1           moltype = AA   length = 431
FEATURE                Location/Qualifiers
source                 1..431
                       mol_type = protein
                       organism = Homo sapiens
SEQUENCE: 1
MPNPRPGKPS APSLALGPSP GASPSWRAAP KASDLLGARG PGGTFQGRDL RGGAHASSSS   60
LNPMPPSQLQ LPTLPLVMVA PSGARLGPLP HLQALLQDRP HFMHQLSTVD AHARTPVLQV  120
HPLESPAMIS LTPPTTATGV FSLKARPGLP PGINVASLEW VSREPALLCT FPNPSAPRKD  180
STLSAVPQSS YPLLANGVCK WPGCEKVFEE PEDFLKHCQA DHLLDEKGRA QCLLQREMVQ  240
SLEQQLVLEK EKLSAMQAHL AGKMALTKAS SVASSDKGSC CIVAAGSQGP VVPAWSGPRE  300
APDSLFAVRR HLWGSHGNST FPEFLHNMDY FKFHNMRPPF TYATLIRWAI LEAPEKQRTL  360
NEIYHWFTRM FAFFRNHPAT WKNAIRHNLS LHKCFVRVES EKGAVWTVDE LEFRKKRSQR  420
PSRCSNPTPG P                                                      431

SEQ ID NO: 2           moltype = DNA   length = 1293
FEATURE                Location/Qualifiers
source                 1..1293
                       mol_type = genomic DNA
                       organism = Homo sapiens
SEQUENCE: 2
atgcctaacc cccgcccctgg aaaaccatct gccccttcac tggccctggg accttcaccc   60
ggagcctcac catcttggag agccgccccc aaggccagcg acctgctggg agccagaggc  120
cccggcggca ccttccaggg cagggatctg cgcggcggcg cccacgccag ctcctctagc  180
ctgaacccca tgcccccttc tcagctccag ctgcccacac tgcccctggt catggtggca  240
cctagcggag caaggctggg accactgcca cacctccagg ccctgctcca ggacagacct  300
cactttatgc accagctgtc caccgtggat gcacacgcaa ggacaccggt gctccaggtg  360
caccctctgg agtctccagc catgatcagc ctgaccccac caaccacagc aacaggcgtg  420
ttctcccctga aggccagacc tggcctgcct ccaggcatca acgtggcctc cctggagtgg  480
gtgtctaggg agccagccct gctgtgcacc tttcctaatc catctgcccc cgcaaggac   540
tccacactgt ctgccgtgcc acagtcctct tacccctgc tggccaacgg cgtgtgcaag   600
tggcctggct gtgagaaggt gttcgaggag ccagaggatt ttctgaagca ctgccaggcc   660
gaccacctgc tggatgagaa gggaagggca cagtgtctgc tccagaggga gatggtgcag   720
agcctggagc agcagctggt gctgagaag gagaagctgt ccgccatgca ggcacacctg   780
gcaggcaaga tggcactgac caaggccagc tccgtggcct ctagcgacaa gggcagctgc  840
tgtatcgtgg ccgccggctc ccagggacca gtggtgcccg cctggtctgg acccaggag  900
gcacctgaca gcctgttcgc cgtgcggaga cacctgtggg gcagccacgg caattccacc  960
ttccccgagt ttctgcacaa catggattac ttcaagtttc acaatatgcg gccccctttt 1020
acctatgcca cactgatcag atgggccatc ctggaggccc cagagaagca gcgcacccta 1080
aacgaaatct accactggtt cacacggatg tttgccttct ttagaaatca ccccgccacc 1140
tggaagaacg ccatcaggca caatctgtcc ctgcacaagt gtttcgtgcg cgtggagtct 1200
gagaagggcg ccgtgtggac agtggatgag ctggacttca gaaagaagag aagccagaga 1260
ccatccaggt gttcaaaccc taccccagga ccc                                1293

SEQ ID NO: 3           moltype = DNA   length = 232
FEATURE                Location/Qualifiers
source                 1..232
                       mol_type = genomic DNA
                       organism = Homo sapiens
SEQUENCE: 3
cctgccctttg gacaaggacc cgatgccaa cccaggcct ggcaagccct cggccccttc   60
cttgccctt ggcccatccc caggagcctc gccagctgg agggctgcac ccaaagcctc  120
agacctgctg ggggcccggg gcccaggggg aaccttccag gccgagatc ttcgaggcgg  180
gcccatgcc tcctcttctt ccttgaaccc catgccacca tcgcagctgc ag          232
```

```
SEQ ID NO: 4            moltype = AA   length = 164
FEATURE                 Location/Qualifiers
source                  1..164
                        mol_type = protein
                        organism = Homo sapiens
SEQUENCE: 4
MKWKALFTAA ILQAQLPITE AQSFGLLDPK LCYLLDGILF IYGVILTALF LRVKFSRSAD    60
APAYQQGQNQ LYNELNLGRR EEYDVLDKRR GRDPEMGGKP QRRKNPQEGL YNELQKDKMA   120
EAYSEIGMKG ERRRGKGHDG LYQGLSTATK DTYDALHMQA LPPR                    164

SEQ ID NO: 5            moltype = AA   length = 105
FEATURE                 Location/Qualifiers
source                  1..105
                        mol_type = protein
                        organism = Homo sapiens
SEQUENCE: 5
IEVMYPPPYL DNEKSNGTII HVKGKHLCPS PLFPGPSKPF WVLVVVGGVL ACYSLLVTVA    60
FIIFWVRSKR SRLLHSDYMN MTPRRPGPTR KHYQPYAPPR DFAAY                   105

SEQ ID NO: 6            moltype = AA   length = 252
FEATURE                 Location/Qualifiers
REGION                  1..252
                        note = MAdCAM1 scFv 32.3
source                  1..252
                        mol_type = protein
                        organism = synthetic construct
SEQUENCE: 6
EVQLLESGGG LVQPGGSLRL SCAASGFSFS SSYWICWVRQ APGKGLEWVS CIYGGSSGAT    60
YYANWAKGRF TISRDNSKNT LYLQMNSLRA EDTAVYYCAR SGSTTSGGVY RWYFNLWGQG   120
TLVTVSSGGG GSGGGGSGGG GSDIQMTQSP SSLSASVGDR VTITCQASEN IYNLLAWYQQ   180
KPGKVPKLLI YDASTLQSGV PSRFSGSGSG TDFTLTISSL QPEDVATYYC QFTYYGGTYE   240
SAFGGGTKVE IK                                                       252

SEQ ID NO: 7            moltype = AA   length = 252
FEATURE                 Location/Qualifiers
REGION                  1..252
                        note = MAdCAM1 scFv 32.4
source                  1..252
                        mol_type = protein
                        organism = synthetic construct
SEQUENCE: 7
EVQLLESGGG LVQPGGSLRL SCAASGFSFS SSYWICWVRQ APGKGLEWVS CIYGGSSGAT    60
YYANWAKGRF TISRDNSKNT LYLQMNSLRA EDTAVYYCAR SGSTTSGGVY RWYFNLWGQG   120
TLVTVSSGGG GSGGGGSGGG GSDIQMTQSP SSLSASVGDR VTITCQASEN IYNLLAWYQQ   180
KPGKAPKLLI YDASNLETGV PSRFSGSGSG TDFTFTISSL QPEDIATYYC QFTYYGGTYE   240
SAFGGGTKVE IK                                                       252

SEQ ID NO: 8            moltype = AA   length = 252
FEATURE                 Location/Qualifiers
REGION                  1..252
                        note = MAdCAM1 scFv 32.5
source                  1..252
                        mol_type = protein
                        organism = synthetic construct
SEQUENCE: 8
QVQLVESGGG VVQPGRSLRL SCAASGFSFS SSYWICWVRQ APGKGLEWVA CIYGGSSGAT    60
YYANWAKGRF TISRDNSTNT LFLQMNSLRA EDTAVYYCAR SGSTTSGGVY RWYFNLWGQG   120
TLVTVSSGGG GSGGGGSGGG GSDIQMTQSP SSLSASVGDR VTITCQASEN IYNLLAWYQQ   180
KPGKVPKLLI YDASTLQSGV PSRFSGSGSG TDFTLTISSL QPEDVATYYC QFTYYGGTYE   240
SAFGGGTKVE IK                                                       252

SEQ ID NO: 9            moltype = AA   length = 252
FEATURE                 Location/Qualifiers
REGION                  1..252
                        note = MAdCAM1 scFv 32.6
source                  1..252
                        mol_type = protein
                        organism = synthetic construct
SEQUENCE: 9
QVQLVESGGG VVQPGRSLRL SCAASGFSFS SSYWICWVRQ APGKGLEWVA CIYGGSSGAT    60
YYANWAKGRF TISRDNSTNT LFLQMNSLRA EDTAVYYCAR SGSTTSGGVY RWYFNLWGQG   120
TLVTVSSGGG GSGGGGSGGG GSDIQMTQSP SSLSASVGDR VTITCQASEN IYNLLAWYQQ   180
KPGKAPKLLI YDASNLETGV PSRFSGSGSG TDFTFTISSL QPEDIATYYC QFTYYGGTYE   240
SAFGGGTKVE IK                                                       252
```

```
SEQ ID NO: 10            moltype = AA   length = 252
FEATURE                  Location/Qualifiers
REGION                   1..252
                         note = MAdCAM1 scFv 32.7
source                   1..252
                         mol_type = protein
                         organism = synthetic construct
SEQUENCE: 10
EVQLVESGGG LVQPGGSLRL SCAASGFSFS SSYWICWVRQ APGKGLEWVS CIYGGSSGAT   60
YYANWAKGRF TISRHNSKNT LYLQMNSLRA EDTAVYYCAR SGSTTSGGVY RWYFNLWGQG  120
TLVTVSSGGG GSGGGGSGGG GSDIQMTQSP SSLSASVGDR VTITCQASEN IYNLLAWYQQ  180
KPGKVPKLLI YDASTLQSGV PSRFSGSGSG TDFTLTISSL QPEDVATYYC QFTYYGGTYE  240
SAFGGGTKVE IK                                                     252

SEQ ID NO: 11            moltype = AA   length = 252
FEATURE                  Location/Qualifiers
REGION                   1..252
                         note = MAdCAM1 scFv 32.8
source                   1..252
                         mol_type = protein
                         organism = synthetic construct
SEQUENCE: 11
EVQLVESGGG LVQPGGSLRL SCAASGFSFS SSYWICWVRQ APGKGLEWVS CIYGGSSGAT   60
YYANWAKGRF TISRHNSKNT LYLQMNSLRA EDTAVYYCAR SGSTTSGGVY RWYFNLWGQG  120
TLVTVSSGGG GSGGGGSGGG GSDIQMTQSP SSLSASVGDR VTITCQASEN IYNLLAWYQQ  180
KPGKAPKLLI YDASNLETGV PSRFSGSGSG TDFTFTISSL QPEDIATYYC QFTYYGGTYE  240
SAFGGGTKVE IK                                                     252

SEQ ID NO: 12            moltype = AA   length = 246
FEATURE                  Location/Qualifiers
REGION                   1..246
                         note = MAdCAM1 scFv 8.1
source                   1..246
                         mol_type = protein
                         organism = synthetic construct
SEQUENCE: 12
EVQLVESGGG LVQPGGSLRL SCAASGFTLS SSYYMYWVRQ APGKGLEWVS VIYAGDGNTY   60
YASWAKGRFT ISRDNSKNTL YLQMNSLRAE DTAVYYCARG YVGYGYAIDL WGQGTLVTVS  120
SGGGGSGGGG SGGGGSDIQM TQSPSTLSAS VGDRVTITCQ ASQSIYSSLA WYQQKPGKAP  180
KLLIYYASIL PSGVPSRFSG SGSGTEFTLT ISSLQPDDFA TYYCQATTYD STYPNAFGGG  240
TKVEIK                                                            246

SEQ ID NO: 13            moltype = AA   length = 246
FEATURE                  Location/Qualifiers
REGION                   1..246
                         note = MAdCAM1 scFv 8.2
source                   1..246
                         mol_type = protein
                         organism = synthetic construct
SEQUENCE: 13
EVQLVESGGG LVQPGGSLRL SCAASGFTLS SSYYMYWVRQ APGKGLEWVS VIYAGDGNTY   60
YASWAKGRFT ISRDNSKNTL YLQMNSLRAE DTAVYYCARG YVGYGYAIDL WGQGTLVTVS  120
SGGGGSGGGG SGGGGSAIQL TQSPSSLSAS VGDRVTITCQ ASQSIYSSLA WYQQKPGKAP  180
KLLIYYASIL PSGVPSRFSG SGSGTDFTLT ISSLQPEDFA TYYCQATTYD STYPNAFGGG  240
TKVEIK                                                            246

SEQ ID NO: 14            moltype = AA   length = 246
FEATURE                  Location/Qualifiers
REGION                   1..246
                         note = MAdCAM1 scFv 8.4
source                   1..246
                         mol_type = protein
                         organism = synthetic construct
SEQUENCE: 14
EVQLLESGGG LVQPGGSLRL SCAASGFTLS SSYYMYWVRQ APGKGLEWVS AIYAGDGNTY   60
YASWAKGRFT ISRDNSKNTL YLQMNSLRAE DTAVYYCARG YVGYGYAIDL WGQGTLVTVS  120
SGGGGSGGGG SGGGGSAIQL TQSPSSLSAS VGDRVTITCQ ASQSIYSSLA WYQQKPGKAP  180
KLLIYYASIL PSGVPSRFSG SGSGTDFTLT ISSLQPEDFA TYYCQATTYD STYPNAFGGG  240
TKVEIK                                                            246
```

```
SEQ ID NO: 15              moltype = AA  length = 246
FEATURE                    Location/Qualifiers
REGION                     1..246
                           note = MAdCAM1 scFv 8.5
source                     1..246
                           mol_type = protein
                           organism = synthetic construct
SEQUENCE: 15
QVQLVESGGG VVQPGRSLRL SCAASGFTLS SSYYMYWVRQ APGKGLEWVA VIYAGDGNTY   60
YASWAKGRFT ISRDNSKNTL YLQMNSLRAE DTAVYYCARG YVGYGYAIDL WGQGTLVTVS  120
SGGGGSGGGG SGGGGSDIQM TQSPSTLSAS VGDRVTITCQ ASQSIYSSLA WYQQKPGKAP  180
KLLIYYASIL PSGVPSRFSG SGSGTEFTLT ISSLQPDDFA TYYCQATTYD STYPNAFGGG  240
TKVEIK                                                             246

SEQ ID NO: 16              moltype = AA  length = 246
FEATURE                    Location/Qualifiers
REGION                     1..246
                           note = MAdCAM1 scFv 8.6
source                     1..246
                           mol_type = protein
                           organism = synthetic construct
SEQUENCE: 16
QVQLVESGGG VVQPGRSLRL SCAASGFTLS SSYYMYWVRQ APGKGLEWVA VIYAGDGNTY   60
YASWAKGRFT ISRDNSKNTL YLQMNSLRAE DTAVYYCARG YVGYGYAIDL WGQGTLVTVS  120
SGGGGSGGGG SGGGGSAIQL TQSPSSLSAS VGDRVTITCQ ASQSIYSSLA WYQQKPGKAP  180
KLLIYYASIL PSGVPSRFSG SGSGTDFTLT ISSLQPEDFA TYYCQATTYD STYPNAFGGG  240
TKVEIK                                                             246

SEQ ID NO: 17              moltype = AA  length = 246
FEATURE                    Location/Qualifiers
REGION                     1..246
                           note = MAdCAM1 scFv 8.7
source                     1..246
                           mol_type = protein
                           organism = synthetic construct
SEQUENCE: 17
EVQLVETGGG LIQPGGSLRL SCAASGFTLS SSYYMYWVRQ APGKGLEWVS VIYAGDGNTY   60
YASWAKGRFT ISRDNSKNTL YLQMNSLRAE DTAVYYCARG YVGYGYAIDL WGQGTLVTVS  120
SGGGGSGGGG SGGGGSDIQM TQSPSTLSAS VGDRVTITCQ ASQSIYSSLA WYQQKPGKAP  180
KLLIYYASIL PSGVPSRFSG SGSGTEFTLT ISSLQPDDFA TYYCQATTYD STYPNAFGGG  240
TKVEIK                                                             246

SEQ ID NO: 18              moltype = AA  length = 246
FEATURE                    Location/Qualifiers
REGION                     1..246
                           note = MAdCAM1 scFv 8.8
source                     1..246
                           mol_type = protein
                           organism = synthetic construct
SEQUENCE: 18
EVQLVETGGG LIQPGGSLRL SCAASGFTLS SSYYMYWVRQ APGKGLEWVS VIYAGDGNTY   60
YASWAKGRFT ISRDNSKNTL YLQMNSLRAE DTAVYYCARG YVGYGYAIDL WGQGTLVTVS  120
SGGGGSGGGG SGGGGSAIQL TQSPSSLSAS VGDRVTITCQ ASQSIYSSLA WYQQKPGKAP  180
KLLIYYASIL PSGVPSRFSG SGSGTDFTLT ISSLQPEDFA TYYCQATTYD STYPNAFGGG  240
TKVEIK                                                             246

SEQ ID NO: 19              moltype = AA  length = 248
FEATURE                    Location/Qualifiers
REGION                     1..248
                           note = MAdCAM1 scFv 17.1
source                     1..248
                           mol_type = protein
                           organism = synthetic construct
SEQUENCE: 19
EVQLVESGGG LVQPGGSLRL SCAASGFSFS STYYMCWVRQ APGKGLEWVS CIYTGSGNTD   60
YASWAKGRFT ISRHNSKNTL YLQMNSLRAE DTAVYYCARG GIVDSYFTYF DLWGQGTLVT  120
VSSGGGGSGG GGSGGGGSDI QMTQSPSTLS ASVGDRVTIT CQASESIFSN LAWYQQKPGK  180
APKLLIYWAS TLASGVPSRF SGSGSGTEFT LTISSLQPDD FATYYCQSYV YSSSSNDFG  240
GGTKVEIK                                                           248
```

```
SEQ ID NO: 20            moltype = AA   length = 248
FEATURE                  Location/Qualifiers
REGION                   1..248
                         note = MAdCAM1 scFv 17.3
source                   1..248
                         mol_type = protein
                         organism = synthetic construct
SEQUENCE: 20
QVQLLESGGG LVKPGGSLRL SCAASGFSFS STYYMCWIRQ APGKGLEWVS CIYTGSGNTD    60
YASWAKGRFT ISRDNAKNSL YLQMNSLRAE DTAVYYCARG GIVDSYFTYF DLWGQGTLVT   120
VSSGGGGSGG GGSGGGGSDI QMTQSPSTLS ASVGDRVTIT CQASESIFSN LAWYQQKPGK   180
APKLLIYWAS TLASGVPSRF SGSGSGTEFT LTISSLQPDD FATYYCQSYV YSSSSSNDFG   240
GGTKVEIK                                                            248

SEQ ID NO: 21            moltype = AA   length = 248
FEATURE                  Location/Qualifiers
REGION                   1..248
                         note = MAdCAM1 scFv 17.5
source                   1..248
                         mol_type = protein
                         organism = synthetic construct
SEQUENCE: 21
QVQLVESGGG VVQPGRSLRL SCAASGFSFS STYYMCWVRQ APGKGLEWVA CIYTGSGNTD    60
YASWAKGRFT ISRDNSTNTL FLQMNSLRAE DTAVYYCARG GIVDSYFTYF DLWGQGTLVT   120
VSSGGGGSGG GGSGGGGSDI QMTQSPSTLS ASVGDRVTIT CQASESIFSN LAWYQQKPGK   180
APKLLIYWAS TLASGVPSRF SGSGSGTEFT LTISSLQPDD FATYYCQSYV YSSSSSNDFG   240
GGTKVEIK                                                            248

SEQ ID NO: 22            moltype = AA   length = 248
FEATURE                  Location/Qualifiers
REGION                   1..248
                         note = MAdCAM1 scFv 17.7
source                   1..248
                         mol_type = protein
                         organism = synthetic construct
SEQUENCE: 22
EVQLVESGGG LVKPGGSLRL SCAASGFSFS STYYMCWVRQ APGKGLEWVS CIYTGSGNTD    60
YASWAKGRFT ISRDNAKNSL YLQMNSLRAE DTAVYYCARG GIVDSYFTYF DLWGQGTLVT   120
VSSGGGGSGG GGSGGGGSDI QMTQSPSTLS ASVGDRVTIT CQASESIFSN LAWYQQKPGK   180
APKLLIYWAS TLASGVPSRF SGSGSGTEFT LTISSLQPDD FATYYCQSYV YSSSSSNDFG   240
GGTKVEIK                                                            248

SEQ ID NO: 23            moltype = AA   length = 244
FEATURE                  Location/Qualifiers
REGION                   1..244
                         note = MAdCAM1 scFv 2.1
source                   1..244
                         mol_type = protein
                         organism = synthetic construct
SEQUENCE: 23
QVQLLESGGG LVKPGGSLRL SCAASGFSFS SGYYMCWIRQ APGKGLEWVS CIYADSSYTY    60
YASWAKGRFT ISRDNAKNSL YLQMNSLRAE DTAVYYCARS NGDYFYGMDL WGQGTLVTVS   120
SGGGGSGGGG SGGGGSDIQM TQSPSSLSAS VGDRVTITCQ ASQSINSWLS WYQQKPGKAP   180
KLLIYRASTL ASGVPSRFSG SGSGTDFTFT ISSLQPEDIA TYYCQSNYYS TSTAFGGGTK   240
VEIK                                                                244

SEQ ID NO: 24            moltype = AA   length = 244
FEATURE                  Location/Qualifiers
REGION                   1..244
                         note = MAdCAM1 scFv 2.2
source                   1..244
                         mol_type = protein
                         organism = synthetic construct
SEQUENCE: 24
QVQLLESGGG LVKPGGSLRL SCAASGFSFS SGYYMCWIRQ APGKGLEWVS CIYADSSYTY    60
YASWAKGRFT ISRDNAKNSL YLQMNSLRAE DTAVYYCARS NGDYFYGMDL WGQGTLVTVS   120
SGGGGSGGGG SGGGGSAIQM TQSPSSLSAS VGDRVTITCQ ASQSINSWLS WYQQKPGKAP   180
KLLIYRASTL ASGVPSRFSG SGSGTDFTLT ISSLQPEDFA TYYCQSNYYS TSTAFGGGTK   240
VEIK                                                                244
```

```
SEQ ID NO: 25          moltype = AA   length = 247
FEATURE                Location/Qualifiers
REGION                 1..247
                       note = MAdCAM1 scFv 10.1
source                 1..247
                       mol_type = protein
                       organism = synthetic construct
SEQUENCE: 25
QVQLVESGGG VVQPGRSLRL SCAASGIDFS GYHYICWVRQ APGKGLEWVA CIYTVSSGIW    60
YATWAKGRFT ISRDNSTNTL FLQMNSLRAE DTAVYYCARD DADVSGYWFD LWGQGTLVTV   120
SSGGGGSGGG GSGGGGSDIQ MTQSPSSLSA SVGDRVTITC QASQSISNLL AWYQQKPGKA   180
PKLLIYKAST LASGVPSRFS GSGSGTDFTF TISSLQPEDI ATYYCQQGIT NNGIDHGFGG   240
GTKVEIK                                                            247

SEQ ID NO: 26          moltype = AA   length = 247
FEATURE                Location/Qualifiers
REGION                 1..247
                       note = MAdCAM1 scFv 10.2
source                 1..247
                       mol_type = protein
                       organism = synthetic construct
SEQUENCE: 26
QVQLVESGGG VVQPGRSLRL SCAASGIDFS GYHYICWVRQ APGKGLEWVA CIYTVSSGIW    60
YATWAKGRFT ISRDNSTNTL FLQMNSLRAE DTAVYYCARD DADVSGYWFD LWGQGTLVTV   120
SSGGGGSGGG GSGGGGSAIQ LTQSPSSLSA SVGDRVTITC QASQSISNLL AWYQQKPGKA   180
PKLLIYKAST LASGVPSRFS GSGSGTDFTL TISSLQPEDF ATYYCQQGIT NNGIDHGFGG   240
GTKVEIK                                                            247

SEQ ID NO: 27          moltype = AA   length = 247
FEATURE                Location/Qualifiers
REGION                 1..247
                       note = MAdCAM1 scFv 10.3
source                 1..247
                       mol_type = protein
                       organism = synthetic construct
SEQUENCE: 27
EVQLVESGGG LVKPGGSLRL SCAASGIDFS GYHYICWVRQ APGKGLEWVS CIYTVSSGIW    60
YATWAKGRFT ISRDNAKNSL YLQMNSLRAE DTAVYYCARD DADVSGYWFD LWGQGTLVTV   120
SSGGGGSGGG GSGGGGSDIQ MTQSPSSLSA SVGDRVTITC QASQSISNLL AWYQQKPGKA   180
PKLLIYKAST LASGVPSRFS GSGSGTDFTF TISSLQPEDI ATYYCQQGIT NNGIDHGFGG   240
GTKVEIK                                                            247

SEQ ID NO: 28          moltype = AA   length = 247
FEATURE                Location/Qualifiers
REGION                 1..247
                       note = MAdCAM1 scFv 10.7
source                 1..247
                       mol_type = protein
                       organism = synthetic construct
SEQUENCE: 28
EVQLLESGGG LVQPGGSLRL SCAASGIDFS GYHYICWVRQ APGKGLEWVS CIYTVSSGIW    60
YATWAKGRFT ISRDNSKNTL YLQMNSLRAE DTAVYYCARD DADVSGYWFD LWGQGTLVTV   120
SSGGGGSGGG GSGGGGSDIQ MTQSPSSLSA SVGDRVTITC QASQSISNLL AWYQQKPGKA   180
PKLLIYKAST LASGVPSRFS GSGSGTDFTF TISSLQPEDI ATYYCQQGIT NNGIDHGFGG   240
GTKVEIK                                                            247

SEQ ID NO: 29          moltype = AA   length = 247
FEATURE                Location/Qualifiers
REGION                 1..247
                       note = MAdCAM1 scFv 10.8
source                 1..247
                       mol_type = protein
                       organism = synthetic construct
SEQUENCE: 29
EVQLLESGGG LVQPGGSLRL SCAASGIDFS GYHYICWVRQ APGKGLEWVS CIYTVSSGIW    60
YATWAKGRFT ISRDNSKNTL YLQMNSLRAE DTAVYYCARD DADVSGYWFD LWGQGTLVTV   120
SSGGGGSGGG GSGGGGSAIQ LTQSPSSLSA SVGDRVTITC QASQSISNLL AWYQQKPGKA   180
PKLLIYKAST LASGVPSRFS GSGSGTDFTL TISSLQPEDF ATYYCQQGIT NNGIDHGFGG   240
GTKVEIK                                                            247
```

```
SEQ ID NO: 30           moltype = AA   length = 127
FEATURE                 Location/Qualifiers
REGION                  1..127
                        note = MAdCAM1 scFv 32.3 HC
source                  1..127
                        mol_type = protein
                        organism = synthetic construct
SEQUENCE: 30
EVQLLESGGG LVQPGGSLRL SCAASGFSFS SSYWICWVRQ APGKGLEWVS CIYGGSSGAT    60
YYANWAKGRF TISRDNSKNT LYLQMNSLRA EDTAVYYCAR SGSTTSGGVY RWYFNLWGQG   120
TLVTVSS                                                             127

SEQ ID NO: 31           moltype = AA   length = 110
FEATURE                 Location/Qualifiers
REGION                  1..110
                        note = MAdCAM1 scFv 32.3 LC
source                  1..110
                        mol_type = protein
                        organism = synthetic construct
SEQUENCE: 31
DIQMTQSPSS LSASVGDRVT ITCQASENIY NLLAWYQQKP GKVPKLLIYD ASTLQSGVPS    60
RFSGSGSGTD FTLTISSLQP EDVATYYCQF TYYGGTYESA FGGGTKVEIK              110

SEQ ID NO: 32           moltype = AA   length = 127
FEATURE                 Location/Qualifiers
REGION                  1..127
                        note = MAdCAM1 scFv 32.4 HC
source                  1..127
                        mol_type = protein
                        organism = synthetic construct
SEQUENCE: 32
EVQLLESGGG LVQPGGSLRL SCAASGFSFS SSYWICWVRQ APGKGLEWVS CIYGGSSGAT    60
YYANWAKGRF TISRDNSKNT LYLQMNSLRA EDTAVYYCAR SGSTTSGGVY RWYFNLWGQG   120
TLVTVSS                                                             127

SEQ ID NO: 33           moltype = AA   length = 110
FEATURE                 Location/Qualifiers
REGION                  1..110
                        note = MAdCAM1 scFv 32.4 LC
source                  1..110
                        mol_type = protein
                        organism = synthetic construct
SEQUENCE: 33
DIQMTQSPSS LSASVGDRVT ITCQASENIY NLLAWYQQKP GKAPKLLIYD ASNLETGVPS    60
RFSGSGSGTD FTFTISSLQP EDIATYYCQF TYYGGTYESA FGGGTKVEIK              110

SEQ ID NO: 34           moltype = AA   length = 127
FEATURE                 Location/Qualifiers
REGION                  1..127
                        note = MAdCAM1 scFv 32.5 HC
source                  1..127
                        mol_type = protein
                        organism = synthetic construct
SEQUENCE: 34
QVQLVESGGG VVQPGRSLRL SCAASGFSFS SSYWICWVRQ APGKGLEWVA CIYGGSSGAT    60
YYANWAKGRF TISRDNSTNT LFLQMNSLRA EDTAVYYCAR SGSTTSGGVY RWYFNLWGQG   120
TLVTVSS                                                             127

SEQ ID NO: 35           moltype = AA   length = 110
FEATURE                 Location/Qualifiers
REGION                  1..110
                        note = MAdCAM1 scFv 32.5 LC
source                  1..110
                        mol_type = protein
                        organism = synthetic construct
SEQUENCE: 35
DIQMTQSPSS LSASVGDRVT ITCQASENIY NLLAWYQQKP GKVPKLLIYD ASTLQSGVPS    60
RFSGSGSGTD FTLTISSLQP EDVATYYCQF TYYGGTYESA FGGGTKVEIK              110
```

```
SEQ ID NO: 36              moltype = AA  length = 127
FEATURE                    Location/Qualifiers
REGION                     1..127
                           note = MAdCAM1 scFv 32.6 HC
source                     1..127
                           mol_type = protein
                           organism = synthetic construct
SEQUENCE: 36
QVQLVESGGG VVQPGRSLRL SCAASGFSFS SSYWICWVRQ APGKGLEWVA CIYGGSSGAT   60
YYANWAKGRF TISRDNSTNT LFLQMNSLRA EDTAVYYCAR SGSTTSGGVY RWYFNLWGQG  120
TLVTVSS                                                            127

SEQ ID NO: 37              moltype = AA  length = 110
FEATURE                    Location/Qualifiers
REGION                     1..110
                           note = MAdCAM1 scFv 32.6 LC
source                     1..110
                           mol_type = protein
                           organism = synthetic construct
SEQUENCE: 37
DIQMTQSPSS LSASVGDRVT ITCQASENIY NLLAWYQQKP GKAPKLLIYD ASNLETGVPS   60
RFSGSGSGTD FTFTISSLQP EDIATYYCQF TYYGGTYESA FGGGTKVEIK             110

SEQ ID NO: 38              moltype = AA  length = 127
FEATURE                    Location/Qualifiers
REGION                     1..127
                           note = MAdCAM1 scFv 32.7 HC
source                     1..127
                           mol_type = protein
                           organism = synthetic construct
SEQUENCE: 38
EVQLVESGGG LVQPGGSLRL SCAASGFSFS SSYWICWVRQ APGKGLEWVS CIYGGSSGAT   60
YYANWAKGRF TISRHNSKNT LYLQMNSLRA EDTAVYYCAR SGSTTSGGVY RWYFNLWGQG  120
TLVTVSS                                                            127

SEQ ID NO: 39              moltype = AA  length = 110
FEATURE                    Location/Qualifiers
REGION                     1..110
                           note = MAdCAM1 scFv 32.7 LC
source                     1..110
                           mol_type = protein
                           organism = synthetic construct
SEQUENCE: 39
DIQMTQSPSS LSASVGDRVT ITCQASENIY NLLAWYQQKP GKVPKLLIYD ASTLQSGVPS   60
RFSGSGSGTD FTLTISSLQP EDVATYYCQF TYYGGTYESA FGGGTKVEIK             110

SEQ ID NO: 40              moltype = AA  length = 127
FEATURE                    Location/Qualifiers
REGION                     1..127
                           note = MAdCAM1 scFv 32.8 HC
source                     1..127
                           mol_type = protein
                           organism = synthetic construct
SEQUENCE: 40
EVQLVESGGG LVQPGGSLRL SCAASGFSFS SSYWICWVRQ APGKGLEWVS CIYGGSSGAT   60
YYANWAKGRF TISRHNSKNT LYLQMNSLRA EDTAVYYCAR SGSTTSGGVY RWYFNLWGQG  120
TLVTVSS                                                            127

SEQ ID NO: 41              moltype = AA  length = 110
FEATURE                    Location/Qualifiers
REGION                     1..110
                           note = MAdCAM1 scFv 32.8 LC
source                     1..110
                           mol_type = protein
                           organism = synthetic construct
SEQUENCE: 41
DIQMTQSPSS LSASVGDRVT ITCQASENIY NLLAWYQQKP GKAPKLLIYD ASNLETGVPS   60
RFSGSGSGTD FTFTISSLQP EDIATYYCQF TYYGGTYESA FGGGTKVEIK             110
```

```
SEQ ID NO: 42            moltype = AA   length = 121
FEATURE                  Location/Qualifiers
REGION                   1..121
                         note = MAdCAM1 scFv 8.1 HC
source                   1..121
                         mol_type = protein
                         organism = synthetic construct
SEQUENCE: 42
EVQLVESGGG LVQPGGSLRL SCAASGFTLS SSYYMYWVRQ APGKGLEWVS VIYAGDGNTY    60
YASWAKGRFT ISRDNSKNTL YLQMNSLRAE DTAVYYCARG YVGYGYAIDL WGQGTLVTVS   120
S                                                                  121

SEQ ID NO: 43            moltype = AA   length = 110
FEATURE                  Location/Qualifiers
REGION                   1..110
                         note = MAdCAM1 scFv 8.2 HC
source                   1..110
                         mol_type = protein
                         organism = synthetic construct
SEQUENCE: 43
DIQMTQSPST LSASVGDRVT ITCQASQSIY SSLAWYQQKP GKAPKLLIYY ASILPSGVPS    60
RFSGSGSGTE FTLTISSLQP DDFATYYCQA TTYDSTYPNA FGGGTKVEIK              110

SEQ ID NO: 44            moltype = AA   length = 121
FEATURE                  Location/Qualifiers
REGION                   1..121
                         note = MAdCAM1 scFv 8.2 HC
source                   1..121
                         mol_type = protein
                         organism = synthetic construct
SEQUENCE: 44
EVQLVESGGG LVQPGGSLRL SCAASGFTLS SSYYMYWVRQ APGKGLEWVS VIYAGDGNTY    60
YASWAKGRFT ISRDNSKNTL YLQMNSLRAE DTAVYYCARG YVGYGYAIDL WGQGTLVTVS   120
S                                                                  121

SEQ ID NO: 45            moltype = AA   length = 110
FEATURE                  Location/Qualifiers
REGION                   1..110
                         note = MAdCAM1 scFv 8.2 LC
source                   1..110
                         mol_type = protein
                         organism = synthetic construct
SEQUENCE: 45
AIQLTQSPSS LSASVGDRVT ITCQASQSIY SSLAWYQQKP GKAPKLLIYY ASILPSGVPS    60
RFSGSGSGTD FTLTISSLQP EDFATYYCQA TTYDSTYPNA FGGGTKVEIK              110

SEQ ID NO: 46            moltype = AA   length = 121
FEATURE                  Location/Qualifiers
REGION                   1..121
                         note = MAdCAM1 scFv 8.4 HC
source                   1..121
                         mol_type = protein
                         organism = synthetic construct
SEQUENCE: 46
EVQLLESGGG LVQPGGSLRL SCAASGFTLS SSYYMYWVRQ APGKGLEWVS AIYAGDGNTY    60
YASWAKGRFT ISRDNSKNTL YLQMNSLRAE DTAVYYCARG YVGYGYAIDL WGQGTLVTVS   120
S                                                                  121

SEQ ID NO: 47            moltype = AA   length = 110
FEATURE                  Location/Qualifiers
REGION                   1..110
                         note = MAdCAM1 scFv 8.4 LC
source                   1..110
                         mol_type = protein
                         organism = synthetic construct
SEQUENCE: 47
AIQLTQSPSS LSASVGDRVT ITCQASQSIY SSLAWYQQKP GKAPKLLIYY ASILPSGVPS    60
RFSGSGSGTD FTLTISSLQP EDFATYYCQA TTYDSTYPNA FGGGTKVEIK              110
```

```
SEQ ID NO: 48              moltype = AA   length = 121
FEATURE                    Location/Qualifiers
REGION                     1..121
                           note = MAdCAM1 scFv 8.5 HC
source                     1..121
                           mol_type = protein
                           organism = synthetic construct
SEQUENCE: 48
QVQLVESGGG VVQPGRSLRL SCAASGFTLS SSYYMYWVRQ APGKGLEWVA VIYAGDGNTY   60
YASWAKGRFT ISRDNSKNTL YLQMNSLRAE DTAVYYCARG YVGYGYAIDL WGQGTLVTVS  120
S                                                                 121

SEQ ID NO: 49              moltype = AA   length = 110
FEATURE                    Location/Qualifiers
REGION                     1..110
                           note = MAdCAM1 scFv 8.5 LC
source                     1..110
                           mol_type = protein
                           organism = synthetic construct
SEQUENCE: 49
DIQMTQSPST LSASVGDRVT ITCQASQSIY SSLAWYQQKP GKAPKLLIYY ASILPSGVPS   60
RFSGSGSGTE FTLTISSLQP DDFATYYCQA TTYDSTYPNA FGGGTKVEIK             110

SEQ ID NO: 50              moltype = AA   length = 121
FEATURE                    Location/Qualifiers
REGION                     1..121
                           note = MAdCAM1 scFv 8.6 HC
source                     1..121
                           mol_type = protein
                           organism = synthetic construct
SEQUENCE: 50
QVQLVESGGG VVQPGRSLRL SCAASGFTLS SSYYMYWVRQ APGKGLEWVA VIYAGDGNTY   60
YASWAKGRFT ISRDNSKNTL YLQMNSLRAE DTAVYYCARG YVGYGYAIDL WGQGTLVTVS  120
S                                                                 121

SEQ ID NO: 51              moltype = AA   length = 110
FEATURE                    Location/Qualifiers
REGION                     1..110
                           note = MAdCAM1 scFv 8.6 LC
source                     1..110
                           mol_type = protein
                           organism = synthetic construct
SEQUENCE: 51
AIQLTQSPSS LSASVGDRVT ITCQASQSIY SSLAWYQQKP GKAPKLLIYY ASILPSGVPS   60
RFSGSGSGTD FTLTISSLQP EDFATYYCQA TTYDSTYPNA FGGGTKVEIK             110

SEQ ID NO: 52              moltype = AA   length = 121
FEATURE                    Location/Qualifiers
REGION                     1..121
                           note = MAdCAM1 scFv 8.7 HC
source                     1..121
                           mol_type = protein
                           organism = synthetic construct
SEQUENCE: 52
EVQLVETGGG LIQPGGSLRL SCAASGFTLS SSYYMYWVRQ APGKGLEWVS VIYAGDGNTY   60
YASWAKGRFT ISRDNSKNTL YLQMNSLRAE DTAVYYCARG YVGYGYAIDL WGQGTLVTVS  120
S                                                                 121

SEQ ID NO: 53              moltype = AA   length = 110
FEATURE                    Location/Qualifiers
REGION                     1..110
                           note = MAdCAM1 scFv 8.7 LC
source                     1..110
                           mol_type = protein
                           organism = synthetic construct
SEQUENCE: 53
DIQMTQSPST LSASVGDRVT ITCQASQSIY SSLAWYQQKP GKAPKLLIYY ASILPSGVPS   60
RFSGSGSGTE FTLTISSLQP DDFATYYCQA TTYDSTYPNA FGGGTKVEIK             110
```

```
SEQ ID NO: 54           moltype = AA   length = 121
FEATURE                 Location/Qualifiers
REGION                  1..121
                        note = MAdCAM1 scFv 8.8 HC
source                  1..121
                        mol_type = protein
                        organism = synthetic construct
SEQUENCE: 54
EVQLVETGGG LIQPGGSLRL SCAASGFTLS SSYYMYWVRQ APGKGLEWVS VIYAGDGNTY    60
YASWAKGRFT ISRDNSKNTL YLQMNSLRAE DTAVYYCARG YVGYGYAIDL WGQGTLVTVS   120
S                                                                  121

SEQ ID NO: 55           moltype = AA   length = 110
FEATURE                 Location/Qualifiers
REGION                  1..110
                        note = MAdCAM1 scFv 8.8 LC
source                  1..110
                        mol_type = protein
                        organism = synthetic construct
SEQUENCE: 55
AIQLTQSPSS LSASVGDRVT ITCQASQSIY SSLAWYQQKP GKAPKLLIYY ASILPSGVPS    60
RFSGSGSGTD FTLTISSLQP EDFATYYCQA TTYDSTYPNA FGGGTKVEIK              110

SEQ ID NO: 56           moltype = AA   length = 123
FEATURE                 Location/Qualifiers
REGION                  1..123
                        note = MAdCAM1 scFv 17.1 HC
source                  1..123
                        mol_type = protein
                        organism = synthetic construct
SEQUENCE: 56
EVQLVESGGG LVQPGGSLRL SCAASGFSFS STYYMCWVRQ APGKGLEWVS CIYTGSGNTD    60
YASWAKGRFT ISRHNSKNTL YLQMNSLRAE DTAVYYCARG GIVDSYFTYF DLWGQGTLVT   120
VSS                                                                123

SEQ ID NO: 57           moltype = AA   length = 110
FEATURE                 Location/Qualifiers
REGION                  1..110
                        note = MAdCAM1 scFv 17.1 LC
source                  1..110
                        mol_type = protein
                        organism = synthetic construct
SEQUENCE: 57
DIQMTQSPST LSASVGDRVT ITCQASESIF SNLAWYQQKP GKAPKLLIYW ASTLASGVPS    60
RFSGSGSGTE FTLTISSLQP DDFATYYCQS YVYSSSSSND FGGGTKVEIK              110

SEQ ID NO: 58           moltype = AA   length = 123
FEATURE                 Location/Qualifiers
REGION                  1..123
                        note = MAdCAM1 scFv 17.3 HC
source                  1..123
                        mol_type = protein
                        organism = synthetic construct
SEQUENCE: 58
QVQLLESGGG LVKPGGSLRL SCAASGFSFS STYYMCWIRQ APGKGLEWVS CIYTGSGNTD    60
YASWAKGRFT ISRDNAKNSL YLQMNSLRAE DTAVYYCARG GIVDSYFTYF DLWGQGTLVT   120
VSS                                                                123

SEQ ID NO: 59           moltype = AA   length = 110
FEATURE                 Location/Qualifiers
REGION                  1..110
                        note = MAdCAM1 scFv 17.3 LC
source                  1..110
                        mol_type = protein
                        organism = synthetic construct
SEQUENCE: 59
DIQMTQSPST LSASVGDRVT ITCQASESIF SNLAWYQQKP GKAPKLLIYW ASTLASGVPS    60
RFSGSGSGTE FTLTISSLQP DDFATYYCQS YVYSSSSSND FGGGTKVEIK              110
```

```
SEQ ID NO: 60          moltype = AA  length = 123
FEATURE                Location/Qualifiers
REGION                 1..123
                       note = MAdCAM1 scFv 17.5 HC
source                 1..123
                       mol_type = protein
                       organism = synthetic construct
SEQUENCE: 60
QVQLVESGGG VVQPGRSLRL SCAASGFSFS STYYMCWVRQ APGKGLEWVA CIYTGSGNTD   60
YASWAKGRFT ISRDNSTNTL FLQMNSLRAE DTAVYYCARG GIVDSYFTYF DLWGQGTLVT  120
VSS                                                                123

SEQ ID NO: 61          moltype = AA  length = 110
FEATURE                Location/Qualifiers
REGION                 1..110
                       note = MAdCAM1 scFv 17.5 LC
source                 1..110
                       mol_type = protein
                       organism = synthetic construct
SEQUENCE: 61
DIQMTQSPST LSASVGDRVT ITCQASESIF SNLAWYQQKP GKAPKLLIYW ASTLASGVPS   60
RFSGSGSGTE FTLTISSLQP DDFATYYCQS YVYSSSSSND FGGGTKVEIK             110

SEQ ID NO: 62          moltype = AA  length = 123
FEATURE                Location/Qualifiers
REGION                 1..123
                       note = MAdCAM1 scFv 17.7 HC
source                 1..123
                       mol_type = protein
                       organism = synthetic construct
SEQUENCE: 62
EVQLVESGGG LVKPGGSLRL SCAASGFSFS STYYMCWVRQ APGKGLEWVS CIYTGSGNTD   60
YASWAKGRFT ISRDNAKNSL YLQMNSLRAE DTAVYYCARG GIVDSYFTYF DLWGQGTLVT  120
VSS                                                                123

SEQ ID NO: 63          moltype = AA  length = 110
FEATURE                Location/Qualifiers
REGION                 1..110
                       note = MAdCAM1 scFv 17.7 LC
source                 1..110
                       mol_type = protein
                       organism = synthetic construct
SEQUENCE: 63
DIQMTQSPST LSASVGDRVT ITCQASESIF SNLAWYQQKP GKAPKLLIYW ASTLASGVPS   60
RFSGSGSGTE FTLTISSLQP DDFATYYCQS YVYSSSSSND FGGGTKVEIK             110

SEQ ID NO: 64          moltype = AA  length = 121
FEATURE                Location/Qualifiers
REGION                 1..121
                       note = MAdCAM1 scFv 2.1 HC
source                 1..121
                       mol_type = protein
                       organism = synthetic construct
SEQUENCE: 64
QVQLLESGGG LVKPGGSLRL SCAASGFSFS SGYYMCWIRQ APGKGLEWVS CIYADSSYTY   60
YASWAKGRFT ISRDNAKNSL YLQMNSLRAE DTAVYYCARS NGDYFYGMDL WGQGTLVTVS  120
S                                                                  121

SEQ ID NO: 65          moltype = AA  length = 108
FEATURE                Location/Qualifiers
REGION                 1..108
                       note = MAdCAM1 scFv 2.1 LC
source                 1..108
                       mol_type = protein
                       organism = synthetic construct
SEQUENCE: 65
DIQMTQSPSS LSASVGDRVT ITCQASQSIN SWLSWYQQKP GKAPKLLIYR ASTLASGVPS   60
RFSGSGSGTD FTFTISSLQP EDIATYYCQS NYYSTSTAFG GGTKVEIK               108
```

```
SEQ ID NO: 66            moltype = AA   length = 121
FEATURE                  Location/Qualifiers
REGION                   1..121
                         note = MAdCAM1 scFv 2.2 HC
source                   1..121
                         mol_type = protein
                         organism = synthetic construct
SEQUENCE: 66
QVQLLESGGG LVKPGGSLRL SCAASGFSFS SGYYMCWIRQ APGKGLEWVS CIYADSSYTY    60
YASWAKGRFT ISRDNAKNSL YLQMNSLRAE DTAVYYCARS NGDYFYGMDL WGQGTLVTVS   120
S                                                                  121

SEQ ID NO: 67            moltype = AA   length = 108
FEATURE                  Location/Qualifiers
REGION                   1..108
                         note = MAdCAM1 scFv 2.2 LC
source                   1..108
                         mol_type = protein
                         organism = synthetic construct
SEQUENCE: 67
AIQMTQSPSS LSASVGDRVT ITCQASQSIN SWLSWYQQKP GKAPKLLIYR ASTLASGVPS    60
RFSGSGSGTD FTLTISSLQP EDFATYYCQS NYYSTSTAFG GGTKVEIK                108

SEQ ID NO: 68            moltype = AA   length = 122
FEATURE                  Location/Qualifiers
REGION                   1..122
                         note = MAdCAM1 scFv 10.1 HC
source                   1..122
                         mol_type = protein
                         organism = synthetic construct
SEQUENCE: 68
QVQLVESGGG VVQPGRSLRL SCAASGIDFS GYHYICWVRQ APGKGLEWVA CIYTVSSGIW    60
YATWAKGRFT ISRDNSTNTL FLQMNSLRAE DTAVYYCARD DADVSGYWFD LWGQGTLVTV   120
SS                                                                 122

SEQ ID NO: 69            moltype = AA   length = 110
FEATURE                  Location/Qualifiers
REGION                   1..110
                         note = MAdCAM1 scFv 10.1 LC
source                   1..110
                         mol_type = protein
                         organism = synthetic construct
SEQUENCE: 69
DIQMTQSPSS LSASVGDRVT ITCQASQSIS NLLAWYQQKP GKAPKLLIYK ASTLASGVPS    60
RFSGSGSGTD FTFTISSLQP EDIATYYCQQ GITNNGIDHG FGGGTKVEIK              110

SEQ ID NO: 70            moltype = AA   length = 122
FEATURE                  Location/Qualifiers
REGION                   1..122
                         note = MAdCAM1 scFv 10.2 HC
source                   1..122
                         mol_type = protein
                         organism = synthetic construct
SEQUENCE: 70
QVQLVESGGG VVQPGRSLRL SCAASGIDFS GYHYICWVRQ APGKGLEWVA CIYTVSSGIW    60
YATWAKGRFT ISRDNSTNTL FLQMNSLRAE DTAVYYCARD DADVSGYWFD LWGQGTLVTV   120
SS                                                                 122

SEQ ID NO: 71            moltype = AA   length = 110
FEATURE                  Location/Qualifiers
REGION                   1..110
                         note = MAdCAM1 scFv 10.2 LC
source                   1..110
                         mol_type = protein
                         organism = synthetic construct
SEQUENCE: 71
AIQLTQSPSS LSASVGDRVT ITCQASQSIS NLLAWYQQKP GKAPKLLIYK ASTLASGVPS    60
RFSGSGSGTD FTLTISSLQP EDFATYYCQQ GITNNGIDHG FGGGTKVEIK              110
```

```
SEQ ID NO: 72            moltype = AA  length = 122
FEATURE                  Location/Qualifiers
REGION                   1..122
                         note = MAdCAM1 scFv 10.3 HC
source                   1..122
                         mol_type = protein
                         organism = synthetic construct
SEQUENCE: 72
EVQLVESGGG LVKPGGSLRL SCAASGIDFS GYHYICWVRQ APGKGLEWVS CIYTVSSGIW   60
YATWAKGRFT ISRDNAKNSL YLQMNSLRAE DTAVYYCARD DADVSGYWFD LWGQGTLVTV  120
SS                                                                122

SEQ ID NO: 73            moltype = AA  length = 110
FEATURE                  Location/Qualifiers
REGION                   1..110
                         note = MAdCAM1 scFv 10.3 LC
source                   1..110
                         mol_type = protein
                         organism = synthetic construct
SEQUENCE: 73
DIQMTQSPSS LSASVGDRVT ITCQASQSIS NLLAWYQQKP GKAPKLLIYK ASTLASGVPS   60
RFSGSGSGTD FTFTISSLQP EDIATYYCQQ GITNNGIDHG FGGGTKVEIK            110

SEQ ID NO: 74            moltype = AA  length = 122
FEATURE                  Location/Qualifiers
REGION                   1..122
                         note = MAdCAM1 scFv 10.7 HC
source                   1..122
                         mol_type = protein
                         organism = synthetic construct
SEQUENCE: 74
EVQLLESGGG LVQPGGSLRL SCAASGIDFS GYHYICWVRQ APGKGLEWVS CIYTVSSGIW   60
YATWAKGRFT ISRDNSKNTL YLQMNSLRAE DTAVYYCARD DADVSGYWFD LWGQGTLVTV  120
SS                                                                122

SEQ ID NO: 75            moltype = AA  length = 110
FEATURE                  Location/Qualifiers
REGION                   1..110
                         note = MAdCAM1 scFv 10.7 LC
source                   1..110
                         mol_type = protein
                         organism = synthetic construct
SEQUENCE: 75
DIQMTQSPSS LSASVGDRVT ITCQASQSIS NLLAWYQQKP GKAPKLLIYK ASTLASGVPS   60
RFSGSGSGTD FTFTISSLQP EDIATYYCQQ GITNNGIDHG FGGGTKVEIK            110

SEQ ID NO: 76            moltype = AA  length = 122
FEATURE                  Location/Qualifiers
REGION                   1..122
                         note = MAdCAM1 scFv 10.8 HC
source                   1..122
                         mol_type = protein
                         organism = synthetic construct
SEQUENCE: 76
EVQLLESGGG LVQPGGSLRL SCAASGIDFS GYHYICWVRQ APGKGLEWVS CIYTVSSGIW   60
YATWAKGRFT ISRDNSKNTL YLQMNSLRAE DTAVYYCARD DADVSGYWFD LWGQGTLVTV  120
SS                                                                122

SEQ ID NO: 77            moltype = AA  length = 110
FEATURE                  Location/Qualifiers
REGION                   1..110
                         note = MAdCAM1 scFv 10.8 LC
source                   1..110
                         mol_type = protein
                         organism = synthetic construct
SEQUENCE: 77
AIQLTQSPSS LSASVGDRVT ITCQASQSIS NLLAWYQQKP GKAPKLLIYK ASTLASGVPS   60
RFSGSGSGTD FTLTISSLQP EDFATYYCQQ GITNNGIDHG FGGGTKVEIK            110
```